United States Patent
Nuopponen et al.

(10) Patent No.: US 12,258,547 B2
(45) Date of Patent: Mar. 25, 2025

(54) CELL CULTURE PLATE, METHOD FOR PREPARING THEREOF AND METHOD FOR DETECTING A SUBSTANCE

(71) Applicant: UPM-Kymmene Corporation, Helsinki (FI)

(72) Inventors: Markus Nuopponen, Helsinki (FI); Lauri Paasonen, Järvenpää (FI); Marika Mannerström, Turku (FI); Tuula Heinonen, Espoo (FI); Tarja Toimela, Pirkkala (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 446 days.

(21) Appl. No.: 16/878,044

(22) Filed: May 19, 2020

(65) Prior Publication Data

US 2020/0385660 A1 Dec. 10, 2020

(30) Foreign Application Priority Data

Jun. 10, 2019 (EP) ..................................... 19397521

(51) Int. Cl.
| | |
|---|---|
| C12M 1/32 | (2006.01) |
| C12M 1/00 | (2006.01) |
| C12M 1/12 | (2006.01) |
| C12N 5/00 | (2006.01) |
| C12Q 1/02 | (2006.01) |
| G01N 33/50 | (2006.01) |

(52) U.S. Cl.
CPC ............ *C12M 23/12* (2013.01); *C12M 23/34* (2013.01); *C12M 25/06* (2013.01); *C12N 5/0018* (2013.01); *C12Q 1/025* (2013.01); *G01N 33/502* (2013.01); *C12N 2533/52* (2013.01); *C12N 2533/54* (2013.01); *C12N 2533/78* (2013.01); *G01N 2500/10* (2013.01)

(58) Field of Classification Search
None
See application file for complete search history.

(56) References Cited

U.S. PATENT DOCUMENTS

2018/0024121 A1    1/2018   Yliperttula et al.

FOREIGN PATENT DOCUMENTS

| JP | 2007215472 A | | 8/2007 |
|---|---|---|---|
| WO | 2012056109 A2 | | 5/2012 |
| WO | WO 2012/056109 | * | 5/2012 |
| WO | 2013093198 A1 | | 6/2013 |
| WO | 2016001480 A1 | | 1/2016 |
| WO | 2016103002 A1 | | 6/2016 |
| WO | 2016193548 A1 | | 12/2016 |

OTHER PUBLICATIONS

Berry et al., Lab Chip 17: 4253-4264 (2017).*
(Continued)

*Primary Examiner* — Erin M. Bowers
(74) *Attorney, Agent, or Firm* — CANTOR COLBURN LLP

(57) ABSTRACT

A cell culture plate includes one or more cell culture well(s) including at least one barrier for dividing the well into at least two compartments, wherein the barrier includes nano-fibrillar cellulose hydrogel, and a method for the preparation thereof. A method for detecting a substance is also disclosed.

20 Claims, 20 Drawing Sheets

(56) References Cited

OTHER PUBLICATIONS

Curvello et al., Advances in Colloid and Interface Science 267: 47-61 (2019).*
Berry, S. B. et al., "Upgrading well plates using open microfluidic patterning", Lab on a Chip, vol. 17, 2017; pp. 4253-4264.
Curvello, R. et al., "Engineering nanocellulose hydrogels for biomedical applications", Advances in Colloid and Interface Science, vol. 267, 2019; pp. 47-61.
Lou, Yan-Ru et al., "The Use of Nanofibrillar Cellulose Hydrogel As a Flexible Three-Dimensional Model to Culture Human Pluripotent Stem Cells", Stem Cells and Development, vol. 23, No. 4, 2014; pp. 380-392.
Berry et al., "Electronic Supporting Information—Upgrading well plates using open microfluidic patterning," Lab on a Chip, 2017, vol. 17, 10 pages.

\* cited by examiner 100x magnification 400x magnification

CELL CULTURE PLATE, METHOD FOR PREPARING THEREOF AND METHOD FOR DETECTING A SUBSTANCE

CROSS REFERENCE TO RELATED APPLICATIONS

This application claims priority to European Application No. 19397521.6, filed Jun. 10, 2019, the contents of which are incorporated herein by reference in their entirety.

TECHNICAL FIELD

The present application relates to a cell culture plate comprising a nanofibrillar cellulose barrier diving a cell culture well on the plate into at least two compartments, and to a method for preparing thereof. The present application also relates to a method detecting a substance and to a method for evaluating an effect of a substance to a cell.

BACKGROUND

In certain cell culture methods it may be necessary to divide the cell culture area, such as a petri dish or a well in a multi-well plate, into two or more compartments. A barrier may be provided for dividing the area into the compartments. It may be desired that certain agents can penetrate the barrier, but for example the cells cannot.

Porous plastic inserts may be used as barriers. Such inserts however may not be fully compatible with living cells and the diffusion of agents though the pores may not be optimal. It is desired to obtain such barrier materials which are well suitable for living material, provide desired diffusion properties and are easy to handle.

SUMMARY

In the present invention it was found out that nanofibrillar cellulose is ideal material for providing barrier properties in cell culture applications. Nanofibrillar cellulose prevents cell from passing through the barrier, but allows smaller molecules and even extracellular vesicles to pass. It is also possible to control the barrier properties of the nanofibrillar cellulose by adjusting the concentration and chemical form thereof.

The present application provides a cell culture plate comprising one or more cell culture well(s) comprising at least one barrier for dividing the well into at least two compartments, wherein the barrier comprises nanofibrillar cellulose hydrogel.

The present application also provides a method for preparing a cell culture plate, the method comprising
  providing a cell culture plate comprising one or more cell culture well(s),
  providing an aqueous dispersion comprising nanofibrillar cellulose, preferably 0.8-2.5% (w/w) of nanofibrillar cellulose,
  forming at least one barrier from the nanofibrillar cellulose into at least one cell culture well for dividing the well into at least two compartments. The obtained cell culture plate may be any of the cell culture plate described herein.

The present application also provides a method for detecting a substance, the method comprising
  providing the cell culture plate comprising a first cell in a first compartment, and
  detecting from another compartment at least one substance.

The main embodiments are characterized in the independent claims. Various embodiments are disclosed in the dependent claims. The embodiments and examples recited in the claims and the specification are mutually freely combinable unless otherwise explicitly stated.

The nanofibrillar cellulose, which is present as a hydrogel, provides a hydrophilic matrix, which is non-toxic, biocompatible and also biodegradable. The matrix can be degraded enzymatically, for example by adding cellulase. On the other hand the hydrogel is stable at physiological conditions, and does not need to be crosslinked by using additional agents. The properties, such as permeability, of the nanofibrillar cellulose hydrogel may be controlled by adjusting the chemical and/or physical properties of the nanofibrillar cellulose.

Certain advantageous properties of the hydrogel comprising nanofibrillar cellulose include flexibility, elasticity and remouldability. As the hydrogel contains a lot of water, it also shows good permeability for molecules. The hydrogels of the embodiments also provide high water retention capacity and molecule diffusion property speed.

The nanofibrillar cellulose hydrogels described herein are useful in medical and scientific applications, wherein the materials comprising nanofibrillar cellulose are in contact with living matter. The products containing nanofibrillar cellulose as described herein are highly biocompatible with the living matter and provide several advantageous effects. Without binding to any specific theory, it is believed that a hydrogel comprising very hydrophilic nanofibrillar cellulose having a very high specific surface area, and thus high water retention ability, when applied against cells, provides favourable moist environment between the cells and the hydrogel comprising nanofibrillar cellulose. The high amount of free hydroxyl groups in the nanofibrillar cellulose forms hydrogen bonds between the nanofibrillar cellulose and water molecules and enables gel formation and the high water retention ability of the nanofibrillar cellulose. The nanofibrillar cellulose hydrogel contains a high amount of water, and it also enables migration of fluids and/or agents.

The nanofibrillar cellulose may be used as a matrix for the cells thus providing an environment, which protects the cells and helps them maintain their viability. One advantage of the nanofibrillar cellulose material is that the dimensions of the fibrillar network of cellulose nanofibers is very close to natural ECM network of collagen nanofibers. Furthermore, cellulose nanofiber is non-animal based material, so there is no risk for disease transfer. With the present materials it is possible to obtain a transparent and porous matrix for the cells, and the handling of the material is easy compared to the alternatives. Cellulose nanofibers have negligible fluorescence background. Cellulose nanofiber hydrogel has optimal elasticity, stiffness, shear stress, mechanical adhesion and porosity to be also used as 3D and 2D cell storage or culture matrix.

As the nanofibrillar cellulose hydrogel barrier can prevent the cells from passing the barrier, but allows the migration of smaller substances, it can be used in a variety of methods for investigating cells. One or more of cell types may be isolated in their own compartments and one or more agent(s) secreted by the cells and/or otherwise provided into an compartment can be investigated in the same compartment or in another compartment behind the barrier. In such way the a direct contact with cells can be eliminated. It is for example possible to study an agent or the effect provided by the agent, such as a metabolite, secreted by a first cell to a second cell. When the cells are in different compartments, they are physically isolated from each other and the effect of cells interacting directly, i.e. being in physical contact, can be eliminated. Therefore it is possible to obtain products which can be used in medical and scientific research.

The nanofibrillar cellulose is specific nanoscale material differing from conventional cellulose, so it is possible to prepare materials and products which exhibit different properties than conventional products. Such products can be prepared using devices capable of outputting the hydrogel material into desired form, for example devices utilizing additive manufacturing, i.e. 3D printing.

GrowDex barriers.

Figure 27:
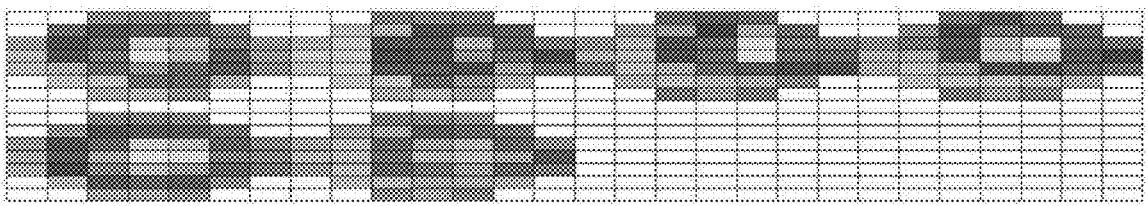

FIG. 27 shows absorbance measurement of the 24-well plate at 450 nm after 24 hrs exposure to chemicals and 2.5 hrs WST-1 incubation.

Figure 28:
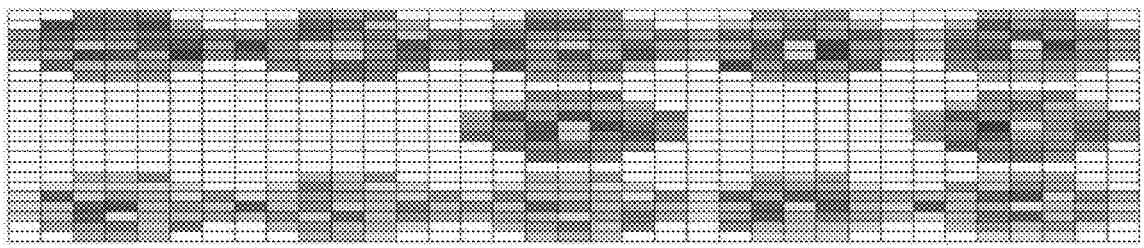

FIG. 28 shows absorbance measurement of the 24-well plate at 450 nm after 24 hrs exposure to chemicals and 2.5 hrs WST-1 incubation.

Figure 29:

FIG. 29 shows 1.5% GrowDex barriers before seeding of BJ cells and exposure (upper image), and after exposure and addition of WST-1 reagent (lower image).

Figure 30:
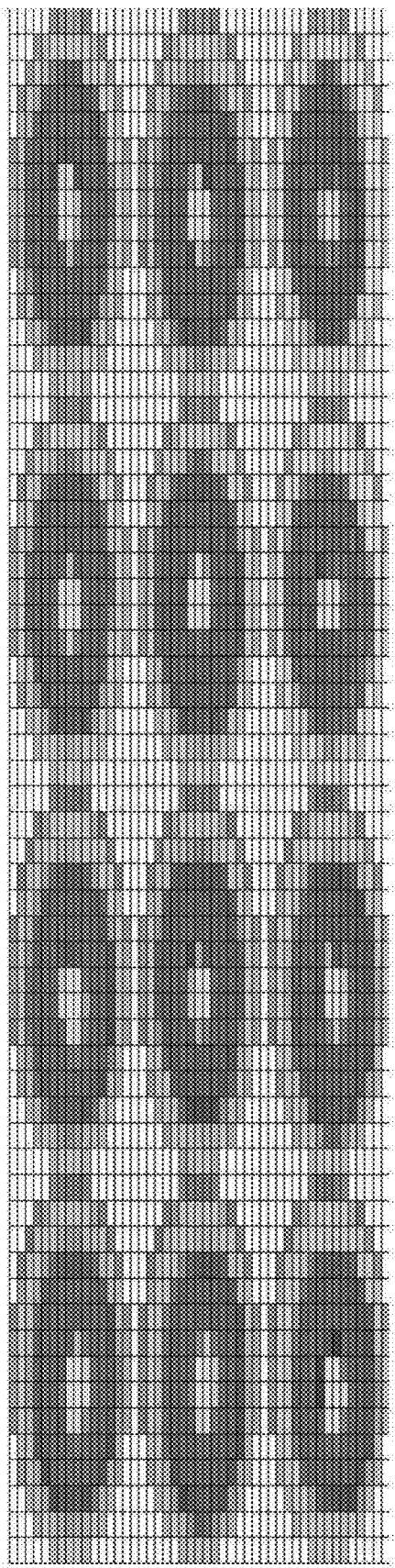

FIG. 30 shows absorbance measurement of the 12-well plate at 450 nm after 24 hrs exposure to chemicals and 2 hrs WST-1 incubation.

Figure 31:
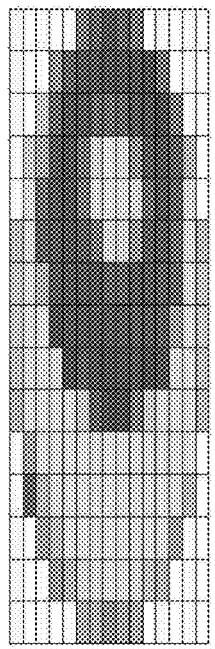
Figure 31:
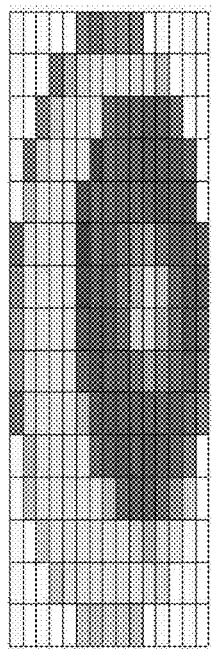

FIG. 31 shows blanks: 1.5% GrowDex barrier in PBS (left), and 1.5% GrowDex barrier in MEM (right), absorbance at 450 nm.

DETAILED DESCRIPTION

In this specification, percentage values, unless specifically indicated otherwise, are based on weight (w/w). If any numerical ranges are provided, the ranges include also the upper and lower values. The open term "comprise" also includes a closed term "consisting of" as one option.

The materials and products described herein may be medical and/or scientific materials and products, such as life science materials and products, and may be used in the methods and the applications involving living cells and/or bioactive material or substances, such as described herein. The materials or products may be or relate to cell culture, cell storage and/or cell study materials or products, and may be used in methods wherein cells are cultured, stored, maintained, transported, provided, modified, tested, and/or used for medical or scientific purposes, or in other related and applicable methods.

The present disclosure provides a cell culture plate comprising one or more cell culture well(s). The cell culture plate may be any suitable cell culture plate or support, which contains at least one specified area for receiving cells, such as a well or a corresponding structure. One example of a cell culture plate is a Petri dish, also called simply as a cell culture dish, which are usually round dishes with a protruding edge surrounding the cell culture area thus forming a well. Another example of a cell culture plate is a multi-well plate, also called as microplate, multiplate, microtiter plate, microwell plate or multiwell, which is a flat plate with multiple wells, such as 6, 12, 24, 48, 96, or 384 sample wells which may be arranged for example in a 2:3 rectangular matrix. One well may hold from tens of nanolitres to several millilitres of liquid and/or other applicable substances. The cell culture plates may be equipped with loose removable covers, for example allowing gas exchange during incubation or cell culture.

The cell culture plates may be manufactured from a variety of materials, such as glass or plastics. The most common is polystyrene, used for most optical detection microplates, but also polypropylene, polycarbonate, cycloolefins and other thermoplastics or thermosetting polymers may be used. The material is preferably transparent to allow visual inspection of the wells by eye or by using specific devices for optically reading the plates, especially multiwell plates.

One or more of the wells comprise at least one barrier for dividing the well into at least two compartments, wherein the barrier comprises nanofibrillar cellulose hydrogel. The compartment(s) is/are preferably designed for receiving cells, liquid, gel, suspension, dispersion and/or the like. At least one compartment is designed to receive cells, which may mean that cells may be applied, incubated and/or cultured in the compartment. The size or volume of a compartment capable of containing cells, cell suspension, liquid or the like, which is defined by the height of the barrier and the area defined by the barrier and optionally other barrier structures, such as well wall, is suitable for carrying out the actions discussed herein, such as incubating, culturing, testing and the like actions.

To control and adjust the barrier properties, for example permeability of certain substances, cell organelles or cells, it may be necessary to provide the nanofibrillar cellulose in certain percentage and/or in certain chemical form. It is also possible to include other substances or additives, or form the barrier structure into a specific form. The nanofibrillar cellulose may be the only organic, polymeric or cellulosic material in the barrier. However, in some examples other reinforcing polymeric or other organic materials or compounds may be included, such as other polysaccharides, for example alginate, starch, glycogen, non-fibrillated cellulose and the like, such as in an amount of 1-50% (w/w) of the dry substances of the barrier, for example 1-20% (w/w) or 1-10% (w/w).

The nanofibrillar cellulose may be chemically modified or it may be chemically unmodified. In one embodiment the nanofibrillar cellulose is selected from unmodified nanofibrillar cellulose, anionically modified nanofibrillar cellulose, and oxidized nanofibrillar cellulose, such as TEMPO oxidized nanofibrillar cellulose. The nanofibrillar cellulose may also be enzymatically modified. Examples of preferable nanofibrillar cellulose forms include anionic and chemically unmodified nanofibrillar cellulose, preferably obtained from wood cellulose.

The concentration of the nanofibrillar cellulose in the barrier may be adjusted, and it may be in the range of 0.8-3.0% (w/w). In one embodiment the nanofibrillar cellulose hydrogel comprises 0.8-2.5% (w/w) of nanofibrillar cellulose. In one embodiment the nanofibrillar cellulose hydrogel comprises 0.8-2.1% (w/w) of nanofibrillar cellulose. In the tests it was found out the a concentration of 1.0-2.1% (w/w) of the nanofibrillar cellulose is preferred for most uses, such as 1.4-2.1% (w/w) or 1.5-2.0% (w/w). Such concentrations ensure that the barrier maintains its shape and form, but also allows flow of the substances of interest through the barrier. The concentration of the nanofibrillar cellulose in the barrier may be the same as the concentration in the starting material, the nanofibrillar hydrogel, but it is also possible that the concentration in the formed barrier, especially in final barrier, which is ready to be used, is higher, for example due drying, handling or other reasons.

The nanofibrillar cellulose may be provided at a suitable fibrillation degree, which may be characterized for example by the rheological properties of the material, and/or the diameter of fibrils or fibril bundles. In one embodiment the nanofibrillar cellulose, when dispersed in water, provides a Brookfield viscosity of at least 2000 mPa·s, such as at least 3000 mPa·s, for example at least 10000 mPa·s, measured at 20° C.±1° C., at a consistency of 0.8% (w/w) and at 10 rpm. In one embodiment the nanofibrillar cellulose, when dispersed in water, provides a zero shear viscosity in the range of 1000-100000 Pa·s, such as in the range of 5000-50000 Pa·s, and a yield stress in the range of 1-50 Pa, such as in the range of 3-15 Pa, determined by rotational rheometer at a consistency of 0.5% (w/w) by weight in aqueous medium at 22° C.±1° C. The nanofibrillar cellulose may have an average fibril diameter of 200 nm or less, such as in the range of 1-200 nm. The "fibril" as used herein may include fibril bundles. Using nanofibrillar cellulose with such high fibrillation degree may facilitate forming of the barrier and also the durability of the barrier. The high fibrillation degree also has an impact to the specific permeability properties and to the interaction of the hydrogel with the cells. Other suitable rheological properties and other features characterizing the fibrillation degree are disclosed in this application.

It is also possible to enhance the attachment of the nanofibrillar cellulose gel into the surface of the cell culture plate by including one or more adhesive agent(s). The surface of the cell culture plate or well may be coated or otherwise treated with such adhesive agent(s), or the adhesive agent(s) may be applied onto the nanofibrillar cellulose or mixed with the nanofibrillar cellulose.

In one embodiment the cell culture plate comprises adhesive agent between the cell culture plate and the nanofibrillar cellulose hydrogel. The adhesive agent may be for example collagen-based adhesive agent, fibrinogen-based adhesive agent, gelatin-based adhesive agent or lysine-based adhesive agent, such as a polymer thereof. In the tests poly-D-lysine and gelatin, or adhesive agents comprising thereof, were found especially effective.

The barrier may be formed as a straight or substantially straight line (FIGS. 11, 12, 15, 16, 17), or a line having one or more bends, which line divides the cell culture well into two or more compartments. In such case the line may begin from one point of the wall of the well and end at another point of the wall of the well. However in such case there may be a risk that the barrier leaks at the points where the barrier meets the wall.

To overcome this risk or problem, the barrier may be formed into a form which defines at least one area on the surface of the cell culture well, i.e. the nanofibrillar cellulose barrier alone forms the barriers of the area and defines the area. The area may form one compartment, and another compartment may be formed outside the defined area. The barrier may be for example in a form of a circle, ellipse, square, triangle, polygon or other form circumscribing at least one area, such as an uneven circle, ellipse, square, triangle, polygon or the like. The term "circle" as used herein may generally refer to any of such forms, which may be called as circle-like forms or closed forms or barriers, or the circle may be replaced by the other forms. Examples of a circle-like barriers are shown in FIGS. 2 and 19-25. In one embodiment the at least one barrier circumscribes at least one area on the cell culture well. Such barrier may be located in the cell culture well in such way that it does not touch the walls of the well, and as the barrier is uniform and does not contain any points of discontinuity, especially it does not join the wall, the leaking problem can be eliminated. In such case, as shown for example in FIG. 2, the barrier forms one compartment inside the barrier circumscribing one area, and another compartment is formed outside the barrier and is circumscribed by the walls of the cell culture well.

The barrier protrudes or ascends from the bottom of the well therefore having a height and a thickness of the barrier wall. The height of the barrier must be high enough to keep the cells, liquids and other materials in the compartment(s) defined by the barrier. The height of the barrier, measured from the surface of bottom of the well, may be at least 50 µm, at least 100 µm, at least 200 µm, at least 500 µm, or preferably at least 1 mm, at least 2 mm or at least 3 mm, for example 0.5-6 mm, 0.5-5 mm, 0.5-3 mm, 1-5 mm, 2-5 mm, 1-4 or 1-3 mm. The height of the barrier and the area defined by the barrier (area of a compartment) usually define the available or useful volume of a compartment. However, if the compartment is filled with gel or the like viscous material or material with high surface tension, it may be possible to apply a little more than the volume of the compartment without overflowing the material from the compartment. The volume of a compartment may be for example in the range of 50-5000 µl, which usually depends on the size of the wells (also amounts of the wells in a plate). For example for 24-well plate the volume of a compartment may be in the range of 50-300 µl, such as 50-200 µl. In the tests a smaller volume was created inside a ring-like barrier, about 50 µl, and a larger volume was obtained outside the barrier, about 200 µl. However, the volumes of the compartments may be also same or substantially same.

The wall thickness of the barrier, i.e. the thickness of a vertical barrier, when applied onto a well, may be for example in the range of 0.5-2 mm, such as 0.5-1.5 mm. Wall thickness below 0.5 may not be durable and may collapse. On the other hand, too high wall thickness may unnecessarily slow down or even prevent the migration of the desired substances though the wall.

Cells and/or other substances, which may be present in liquid, gel, suspension, dispersion or other applicable forms may be applied into the one or more compartment(s). Initially the compartments may be empty, i.e. they do not contain any substances and/or are not filled, or they may be filled with liquid, for example cell culture medium or other medium, either partly or fully. The one or more compartment(s) may be also filled with gel, such as nanofibrillar cellulose hydrogel, agar gel or other suitable gel, which may be hydrogel and which may be arranged to receive cells, which may have a different consistency, concentration and/or composition, for example a lower concentration, compared to the barrier, and which is preferably in contact with the barrier. The concentration of the gel in a compartment may be for example lower than 1.5% (w/w), lower than 1.2% (w/w), lower than 1% (w/w), lower than 0.8% (w/w), lower than 0.7% (w/w), lower than 0.6% (w/w) or lower than 0.5% (w/w). Nanofibrillar cellulose hydrogel can be used as a cell culture material, for example at a consistency of 2% (w/w) or less, preferably 1% (w/w) or less, or 0.8% (w/w) or less, or 0.7% (w/w) or less. The cells may be cultured in the hydrogel having a lower consistency and as the barrier has a higher consistency, the cells cannot enter the barrier. In the cell culturing gel it is possible to provide different conditions, such as conditions supporting the culturing of the cells, which conditions are different from the conditions in the barrier. A cell culture plate containing the barrier and nanofibrillar cellulose hydrogel in one or more of the compartments, can be provided as a product. It is further possible to already include cells in one or more compartments, wherein the products may be called as a cell system.

The cells may be provided in said gel and the cell-containing gel is applied into a compartment. Alternatively a gel without cells is applied into a compartment, and the cells may be later applied into the gel in the compartment. The gel designed to receive the cells may be dilute enough to allow application of the cells for example with a pipette, syringe or the like applicator, and optionally also mixing of the gel to facilitate the distribution of the applied cells into the gel. Therefore different products, either products comprising cells, or products lacking cells, may be prepared and/or provided.

In one embodiment at least one of the compartment(s) comprise(s) nanofibrillar cellulose hydrogel having a lower concentration of nanofibrillar cellulose compared to the barrier, such as a concentration of 0.7% (w/w) or less, for example 0.2-0.7% (w/w) or 0.2-0.5% (w/w). This nanofibrillar cellulose may be chemically modified or it may be chemically unmodified. In one example it is anionically modified nanofibrillar cellulose, such as oxidized nanofibrillar cellulose.

The present disclosure also provides a method for preparing the cell culture plate disclosed herein. A cell culture plate comprising one or more cell culture well(s), as disclosed herein, is provided. The nanofibrillar cellulose is provided, for example as an aqueous dispersion comprising 0.8-2.5% (w/w) of nanofibrillar cellulose and/or in a form of a hydrogel. The method may also include forming the aqueous dispersion from a dried nanofibrillar cellulose or from nanofibrillar cellulose having a different consistency, wherein drying or diluting may be required. Thereafter the method comprises forming the at least one barrier from the nanofibrillar cellulose onto at least one cell culture well for dividing the well into at least two compartments. The nanofibrillar cellulose hydrogel may be applied by using a nozzle, syringe, needle, pipette, or the like means for outputting or providing the hydrogel, and forming the applied hydrogel into a barrier, which preferably has a desired structure and/or form. The barrier may be formed manually or by using one or more manufacturing device(s), apparatus(es), machine(s), mold(s) and the like equipment. The manufacturing device may be computer controlled and provided with computer-readable instructions for forming a desired barrier structure when run in the computer. For example the form or shape of the barrier may be designed by using a computer program such as computer-aided design (CAD) program or the like, and the instructions for preparing the barrier structure are outputted from the program.

In one embodiment the method for preparing the cell culture plate comprises coating or otherwise treating the one or more cell culture well(s), preferably the bottom of the well, with an adhesive agent before providing, such as forming or applying, the at least one barrier. The adhesive may be applied at least between the well and the barrier. This may help attaching the barrier to the cell well, especially to the bottom of the well, but also to the wall of the well if necessary. Without such an adhesive layer the barrier may move in the well or be released, especially if the cell culture plate is moved and for example tilted. When suitable adhesive is applied, a product is obtained which tolerates handling, such as transporting and/or packing.

The adhesive agent may be any suitable and compatible adhesive agent, preferably organic and/or biological agent, usually polymeric agent, such as a collagen-based, fibrinogen-based, gelatin-based or lysine-based adhesive agent. Preferable adhesive agents found in the tests were poly-D-lysine and gelatin.

It was also found out that the homogeneity of the nanofibrillar cellulose plays an important role in forming useful barrier. Even a partial uneven area or layer in the barrier structure may ruin the whole structure. Therefore it may be necessary to prepare the nanofibrillar cellulose material by providing a homogenizing step before providing the material to the final use, such as 3D printing. The homogenizing step may be non-fibrillating homogenization, refining, dispersing or other treatment step, which is preferably carried out after the cellulose has been disintegrated (fibrillated) into nanofibrillar cellulose. Therefor in one embodiment of the method the nanofibrillar cellulose is obtained from such a non-fibrillating homogenizing step.

Suitable liquid, such as storage fluid or medium and/or buffer solution, such as liquid containing salt, such as chloride salt, for example calcium chloride, sodium chloride or other salt, for example 1-2% (w/w) and optionally one or more of buffering agents, preservative(s) and/or other agent(s), may be applied to the well containing the barrier to enhance the storability, such as buffered saline or cell culture medium, for example PDS or MEM. The barrier structures may be stored and provided in said liquids also as separate products. The liquid may be exchanged with a different liquid, such as cell culture medium, prior to use.

Nanofibrillar Cellulose

The starting material for forming the barrier is nanofibrillar cellulose, also called as nanocellulose, which refers to isolated cellulose fibrils or fibril bundles derived from cellulose raw material. Nanofibrillar cellulose is based on a natural polymer that is abundant in nature. Nanofibrillar cellulose has a capability of forming viscous hydrogel in water. Nanofibrillar cellulose production techniques may be based on disintegrating fibrous raw material, such as grinding of aqueous dispersion of pulp fibers to obtain nanofibrillated cellulose. After the grinding or homogenization process, the obtained nanofibrillar cellulose material is a dilute viscoelastic hydrogel.

The obtained material usually exists at a relatively low concentration homogeneously distributed in water due to the disintegration conditions. The starting material may be an aqueous gel at a concentration of 0.2-10% (w/w), for example 0.2-5% (w/w). The nanofibrillar cellulose may be obtained directly from the disintegration of fibrous raw material. An example of commercially available nanofibrillar cellulose hydrogel is GrowDex® by UPM.

Because of its nanoscale structure nanofibrillar cellulose has unique properties which enable functionalities which cannot be provided by conventional cellulose. However, because of the nanoscale structure nanofibrillar cellulose is also a challenging material. For example dewatering or handling of nanofibrillar cellulose may be difficult.

The nanofibrillar cellulose may be prepared from cellulose raw material of plant origin, or it may also be derived from certain bacterial fermentation processes.

The nanofibrillar cellulose is preferably made of plant material. The raw material may be based on any plant material that contains cellulose. In one example the fibrils are obtained from non-parenchymal plant material. In such case the fibrils may be obtained from secondary cell walls. One abundant source of such cellulose fibrils is wood fibres. The nanofibrillar cellulose may be manufactured by homogenizing wood-derived fibrous raw material, which may be chemical pulp. Cellulose fibers are disintegrated to produce fibrils which have an average diameter of only some nanometers, which may be 200 nm or less in most cases, and gives a dispersion of fibrils in water. The fibrils originating from secondary cell walls are essentially crystalline with degree of crystallinity of at least 55%. Such fibrils may have different properties than fibrils originated from primary cell walls, for example the dewatering of fibrils originating from secondary cell walls may be more challenging. In general in the cellulose sources from primary cell walls, such as sugar beet, potato tuber and banana rachis, the microfibrils are easier to liberate from the fibre matrix than fibrils from wood, and the disintegration requires less energy. However, these materials are still somewhat heterogeneous and consist of large fibril bundles.

Non-wood material may be from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. The cellulose raw material could be also derived from the cellulose-producing micro-organism. The micro-organisms can be of the genus *Acetobacter, Agrobacterium, Rhizobium, Pseudomonas or Alcaligenes*, preferably of the genus *Acetobacter* and more preferably of the species *Acetobacter xylinum* or *Acetobacter pasteurianus*.

It was found out that nanofibrillar cellulose obtained from wood cellulose is preferable for medical or scientific products described herein. Wood cellulose is available in large amounts, and the preparation methods developed for wood cellulose enable producing nanofibrillar materials suitable for the products. The nanofibrillar cellulose obtained by fibrillating plant fibers, especially wood fibers, differs structurally from nanofibrillar cellulose obtained from microbes, and it has different properties. For example compared to bacterial cellulose, nanofibrillated wood cellulose is homogenous and more porous and loose material, which is advantageous in applications involving living cells. Bacterial cellulose is usually used as such without similar fibrillation as in plant cellulose, so the material is different also in this respect. Bacterial cellulose is dense material which easily forms small spheroids and therefore the structure of the material is discontinuous, and it is not desired to use such material in the applications relating to living cells, especially when homogeneity of the material is required.

Wood may be from softwood tree such as spruce, pine, fir, larch, douglas-fir or hemlock, or from hardwood tree such as birch, aspen, poplar, alder, eucalyptus, oak, beech or acacia, or from a mixture of softwoods and hardwoods. In one example the nanofibrillar cellulose is obtained from wood pulp. The nanofibrillar cellulose may be obtained from hardwood pulp. In one example the hardwood is birch. The nanofibrillar cellulose may be obtained from softwood pulp.

In one example said wood pulp is chemical pulp. Chemical pulp may be desired for the products disclosed herein. Chemical pulp is pure material and may be used in a wide variety of applications. For example chemical pulp lack the pitch and resin acids present in mechanical pulp, and it is more sterile or easily sterilisable. Further, chemical pulp is more flexible and provides advantageous properties for example in medical and scientific materials. For example very homogenous nanofibrillar cellulose materials may be prepared without excess processing or need for specific equipment or laborious process steps.

Nanofibrillar cellulose, including the cellulose fibrils and/or fibril bundles, is characterized by a high aspect ratio (length/diameter). The average length of nanofibrillar cellulose (the median length of particles such as fibrils or fibril bundles) may exceed 1 μm, and in most cases it is 50 μm or less. If the elementary fibrils are not completely separated from each other, the entangled fibrils may have an average total length for example in the range of 1-100 μm, 1-50 μm, or 1-20 μm. However, if the nanofibrillar material is highly fibrillated, the elementary fibrils may be completely or almost completely separated and the average fibril length is shorter, such as in the range of 1-10 μm or 1-5 μm. This applies especially for native grades of fibrils which are not shortened or digested, for example chemically, enzymatically or mechanically. However, strongly derivatized nanofibrillar cellulose may have a shorter average fibril length, such as in the range of 0.3-50 μm, such as 0.3-20 μm, for example 0.5-10 μm or 1-10 μm. Especially shortened fibrils, such as enzymatically or chemically digested fibrils, or mechanically treated material, may have an average fibril length of less than 1 μm, such as 0.1-1 μm, 0.2-0.8 μm or 0.4-0.6 μm. The fibril length and/or diameter may be estimated microscopically, for example using CRYO-TEM, SEM or AFM images.

The average diameter (width) of nanofibrillar cellulose is less than 1 μm, or 500 nm or less, such as in the range of 1-500 nm, but preferably 200 nm or less, even 100 nm or less or 50 nm or less, such as in the range of 1-200 nm, 2-200 nm, 2-100 nm, or 2-50 nm, even 2-20 for highly fibrillated material. The diameters disclosed herein may refer to fibrils and/or fibril bundles. The smallest fibrils are in the scale of elementary fibrils, the average diameter being typically in the range of 2-12 nm. The dimensions and size distribution of the fibrils depend on the refining method and efficiency. In case of highly refined native nanofibrillar cellulose, the average fibril diameter, including fibril bundles, may be in the range of 2-200 nm or 5-100 nm, for example in the range of 10-50 nm. Nanofibrillar cellulose is characterized by a large specific surface area and a strong ability to form hydrogen bonds. In water dispersion, the nanofibrillar cellulose typically appears as either light or turbid gel-like material. Depending on the fiber raw material, nanofibrillar cellulose obtained from plants, especially wood, may also contain small amounts of other plant components, especially wood components, such as hemicellulose or lignin. The amount is dependent on the plant source.

In general cellulose nanomaterials may be divided into categories according to TAPPI W13021, which provides standard terms for cellulose nanomaterials. Not all of these materials are nanofibrillar cellulose. Two main categories are "Nano objects" and "Nano structured materials". Nanostructured materials include "Cellulose microcrystals" (sometimes called as CMC) having a diameter of 10-12 μm and length:diameter ratio (L/D)<2, and "Cellulose microfibrils" having a diameter of 10-100 nm and a length of 0.5-50 μm. Nano objects include "Cellulose nanofibers", which can be divided into "Cellulose nanocrystals" (CNC) having a diameter of 3-10 nm and L/D>5, and "Cellulose nanofibrils" (CNF or NFC), having a diameter of 5-30 nm and L/D>50.

Different grades of nanofibrillar cellulose may be categorized based on three main properties: (i) size distribution, length and diameter (ii) chemical composition, and (iii) rheological properties. To fully describe a grade, the properties may be used in parallel. Examples of different grades include native (or chemically unmodified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low degree of substitution, low viscosity vs. high viscosity etc. The fibrillation technique and the chemical pre-modification have an influence on the fibril size distribution. Typically, non-ionic grades have wider average fibril diameter (for example in the range of 10-100 nm, or 10-50 nm) while the chemically modified grades are a lot thinner (for example in the range of 2-20 nm). Distribution is also narrower for the modified grades. Certain modifications, especially TEMPO-oxidation, yield shorter fibrils.

Depending on the raw material source, e.g. hardwood vs. softwood pulp, different polysaccharide composition exists in the final nanofibrillar cellulose product. Commonly, the non-ionic grades are prepared from bleached birch pulp, which yields high xylene content (25% by weight). Modified grades are prepared either from hardwood or softwood pulps. In those modified grades, the hemicelluloses are also modified together with the cellulose domain. Most probably, the modification is not homogeneous, i.e. some parts are more modified than others. Thus, detailed chemical analysis is usually not possible as the modified products are complicated mixtures of different polysaccharide structures.

In an aqueous environment, a dispersion of cellulose nanofibers forms a viscoelastic hydrogel network. The gel is formed already at relatively low concentrations of for example 0.05-0.2% (w/w) by dispersed and hydrated entangled fibrils. The viscoelasticity of the NFC hydrogel may be characterized for example with dynamic oscillatory rheological measurements.

The nanofibrillar cellulose hydrogels exhibit characteristic rheological properties. For example they are shear-thinning or pseudoplastic materials, which may be considered as a special case of thixotropic behavior, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent for example on the raw material, the disintegration method and number of disintegration runs. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration treatment is performed at conditions wherein water is sufficiently present to prevent the formation of bonds between the fibers.

In one example the disintegration is carried out by using a disperser having at least one rotor, blade or similar moving mechanical member, such as a rotor-rotor dispergator, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after the other at a high peripheral speed from opposite directions; in other words, it receives a plurality of successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor dispergator the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor dispergator is an Atrex device.

Another example of a device suitable for disintegrating is a pin mill, such as a multi-peripheral pin mill. One example of such device includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one example the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion causes shearing and impact forces on the dispersion, resulting in the removal of fibrils from the fiber material. The fiber fragments are disintegrated into fibrils in the fibrillating step.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The expressions "disintegration" or "disintegration treatment" may be used interchangeably with "fibrillation".

The fiber material dispersion that is subjected to fibrillation is a mixture of fiber material and water, also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

One way to characterize the nanofibrillar cellulose is to use the viscosity of an aqueous solution containing said nanofibrillar cellulose. The viscosity may be for example Brookfield viscosity or zero shear viscosity. The specific viscosity, as described herein, distinguishes nanofibrillar cellulose from non-nanofibrillar cellulose.

In one example the apparent viscosity of the nanofibrillar cellulose is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably RVDV spring (Brookfield RVDV-III) is used in the apparatus. A sample of the nanofibrillar cellulose is diluted to a concentration of 0.8% by weight in water and mixed for 10 min. The diluted sample mass is added to a 250 ml beaker and the temperature is adjusted to 20° C.±1° C., heated if necessary and mixed. A low rotational speed 10 rpm is used. In general Brookfield viscosity may be measured at 20° C.±1° C., at a consistency of 0.8% (w/w) and at 10 rpm.

The nanofibrillar cellulose, for example provided as a starting material in the method, may be characterized by the viscosity it provides in a water solution. The viscosity describes, for example, the fibrillation degree of the nanofibrillar cellulose. In one example the nanofibrillar cellulose when dispersed in water provides a Brookfield viscosity of at least 2000 mPa·s, such as at least 3000 mPa·s, measured at 20° C.±1° C., at a consistency of 0.8% (w/w) and at 10 rpm. In one example the nanofibrillar cellulose, when dispersed in water, provides a Brookfield viscosity of at least 10000 mPa·s measured at 20° C.±1° C., at a consistency of 0.8% (w/w) and at 10 rpm. In one example the nanofibrillar cellulose, when dispersed in water, provides a Brookfield viscosity of at least 15000 mPa·s measured at 20° C.±1° C., at a consistency of 0.8% (w/w) and at 10 rpm. Examples of Brookfield viscosity ranges of said nanofibrillar cellulose when dispersed in water include 2000-20000 mPa·s, 3000-20000 mPa·s, 10000-20000 mPa·s, 15000-20000 mPa·s, 2000-25000 mPa·s, 3000-25000 mPa·s, 10000-25000 mPa·s, 15000-25000 mPa·s, 2000-30000 mPa·s, 3000-30000 mPa·s, 10000-30000 mPa·s, and 15000-30000 mPa·s, measured at 20° C.±1° C., at a consistency of 0.8% (w/w) and at 10 rpm.

The nanofibrillar cellulose may also be characterized by the average diameter (or width), or by the average diameter together with the viscosity, such as Brookfield viscosity or zero shear viscosity. In one example nanofibrillar cellulose suitable for use in the products described herein has an average fibril diameter in the range of 1-200 nm, or 1-100 nm. In one example said nanofibrillar cellulose has an average fibril diameter in the range of 1-50 nm, such as 2-20 nm or 5-30 nm. In one example said nanofibrillar cellulose has an average fibril diameter in the range of 2-15 nm, such as in the case of TEMPO oxidized nanofibrillar cellulose.

The diameter of a fibril may be determined with several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for nanofibrillar cellulose grades with narrow fibril diameter distribution.

A rheometer viscosity of the nanofibrillar cellulose dispersion may be measured at 22° C. with a stress controlled rotational rheometer (AR-G2, TA Instruments, UK) equipped with a narrow gap vane geometry (diameter 28 mm, length 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 $s^{-1}$ is exceeded. This method may be used for determining the zero-shear viscosity.

In one example the nanofibrillar cellulose, for example provided as a starting material in the method, when dispersed in water, provides a zero shear viscosity ("plateau" of constant viscosity at small shearing stresses) in the range of 1000-100000 Pa·s, such as in the range of 5000-50000 Pa·s, and a yield stress (shear stress where the shear thinning begins) in the range of 1-50 Pa, such as in the range of 3-15 Pa, determined by rotational rheometer at a consistency of 0.5% (w/w) by weight in aqueous medium at 22° C.±1° C. Such nanofibrillar cellulose may also have an average fibril diameter of 200 nm or less, such as in the range of 1-200 nm.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

In one turbidity measurement method, a nanofibrillar cellulose sample is diluted in water, to a concentration below the gel point of said nanofibrillar cellulose, and turbidity of the diluted sample is measured. Said concentration where the turbidity of the nanofibrillar cellulose samples is measured is 0.1%. HACH P2100 Turbidometer with a 50 ml measuring vessel is used for turbidity measurements. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units.

One way to characterize nanofibrillar cellulose is to define both the viscosity and the turbidity. Low turbidity refers to small size of the fibrils, such as small diameter, as small fibrils scatter light poorly. In general as the fibrillation degree increases, the viscosity increases and at the same time the turbidity decreases. This happens, however, until a certain point. When the fibrillation is further continued, the fibrils finally begin to break and cannot form a strong network any more. Therefore, after this point, both the turbidity and the viscosity begin to decrease.

In one example the turbidity of anionic nanofibrillar cellulose is lower than 90 NTU, for example from 3 to 90 NTU, such as from 5 to 60, for example 8-40 measured at a consistency of 0.1% (w/w) in aqueous medium, and measured by nephelometry. In one example the turbidity of native nanofibrillar may be even over 200 NTU, for example from 10 to 220 NTU, such as from 20 to 200, for example 50-200 measured at measured at 20° C.±1° C. a consistency of 0.1% (w/w) in aqueous medium, and measured by nephelometry. To characterize the nanofibrillar cellulose these ranges may be combined with the viscosity ranges of the nanofibrillar cellulose, such as nanofibrillar cellulose which, when dispersed in water, provides a Brookfield viscosity of at least 2000 mPa·s, at least 3000 mPa·s, at least 5000 mPa·s, such as at least 10000 mPa·s, for example at least 15000 mPa·s measured at 20° C.±1° C., at a consistency of 0.8% (w/w) and at 10 rpm.

Nanofibrillar cellulose may be or comprise non-modified nanofibrillar cellulose. The drainage of non-modified nanofibrillar cellulose is significantly faster than for example anionic grade. Non-modified nanofibrillar cellulose generally has a Brookfield viscosity in the range of 2000-10000 mPa·s, measured at 20° C.±1° C., at a consistency of 0.8% (w/w) and at 10 rpm. It is preferred that the nanofibrillar cellulose has a suitable carboxylic acid content, such as in the range of 0.6-1.4 mmol COOH/g, for example in the range of 0.7-1.2 mmol COOH/g, or in the range of 0.7-1.0 mmol COOH/g or 0.8-1.2 mmol COOH/g, determined by conductometric titration.

The disintegrated fibrous cellulosic raw material may be modified fibrous raw material. Modified fibrous raw material means raw material where the fibers are affected by the treatment so that cellulose nanofibrils are more easily detachable from the fibers. The modification is usually performed to fibrous cellulosic raw material which exists as a suspension in a liquid, i.e. pulp.

The modification treatment to the fibers may be chemical, enzymatic or physical. In chemical modification the chemical structure of cellulose molecule is changed by chemical reaction ("derivatization" of cellulose), preferably so that the length of the cellulose molecule is not affected but functional groups are added to β-D-glucopyranose units of the polymer. The chemical modification of cellulose takes place at a certain conversion degree, which is dependent on the dosage of reactants and the reaction conditions, and as a rule it is not complete so that the cellulose will stay in solid form as fibrils and does not dissolve in water. In physical modification anionic, cationic, or non-ionic substances or any combination of these are physically adsorbed on cellulose surface.

The cellulose in the fibers may be especially ionically charged after the modification. The ionic charge of the cellulose weakens the internal bonds of the fibers and will later facilitate the disintegration to nanofibrillar cellulose. The ionic charge may be achieved by chemical or physical modification of the cellulose. The fibers may have higher anionic or cationic charge after the modification compared with the starting raw material. Most commonly used chemical modification methods for making an anionic charge are oxidation, where hydroxyl groups are oxidized to aldehydes and carboxyl groups, sulphonization and carboxymethylation. Chemical modifications introducing groups, such as carboxyl groups, which may take part in forming a covalent bond between the nanofibrillar cellulose and the bioactive molecule, may be desired. A cationic charge in turn may be created chemically by cationization by attaching a cationic group to the cellulose, such as quaternary ammonium group.

Nanofibrillar cellulose may comprise chemically modified nanofibrillar cellulose, such as anionically modified nanofibrillar cellulose or cationically modified nanofibrillar cellulose. In one example the nanofibrillar cellulose is anionically modified nanofibrillar cellulose. In one example the anionically modified nanofibrillar cellulose is oxidized nanofibrillar cellulose. In one example the anionically modified nanofibrillar cellulose is sulphonized nanofibrillar cellulose. In one example the anionically modified nanofibrillar cellulose is carboxymethylated nanofibrillar cellulose. The material obtained with the anionical modification of cellulose may be called anionic cellulose, which refers to material wherein the amount or proportion of anionic groups, such as carboxylic groups, is increased by the modification, when compared to a non-modified material. It is also possible to introduce other anionic groups to the cellulose, instead or in addition to carboxylic groups, such as phosphate groups or sulphate groups. The content of these groups may be in the same ranges as is disclosed for carboxylic acid herein.

The cellulose may be oxidized. In the oxidation of cellulose, the primary hydroxyl groups of cellulose may be oxidized catalytically by a heterocyclic nitroxyl compound, such as through N-oxyl mediated catalytic oxidation, for example 2,2,6,6-tetramethylpiperidinyl-1-oxy free radical, generally called "TEMPO". The primary hydroxyl groups (C6-hydroxyl groups) of the cellulosic β-D-glucopyranose units are selectively oxidized to carboxylic groups. Some aldehyde groups are also formed from the primary hydroxyl groups. Regarding the finding that low degree of oxidation does not allow efficient enough fibrillation and higher degree of oxidation inflicts degradation of cellulose after mechanical disruptive treatment, the cellulose may be oxidized to a level having a carboxylic acid content in the oxidized cellulose in the range of 0.5-2.0 mmol COOH/g pulp, 0.6-1.4 mmol COOH/g pulp, or 0.8-1.2 mmol COOH/g pulp, preferably to 1.0-1.2 mmol COOH/g pulp, determined by conductometric titration. When the fibers of oxidized cellulose so obtained are disintegrated in water, they give stable transparent dispersion of individualized cellulose fibrils, which may be, for example, of 3-5 nm in width. With oxidized pulp as the starting medium, it is possible to obtain nanofibrillar cellulose where Brookfield viscosity measured at a consistency of 0.8% (w/w) is at least 10000 mPa·s, for example in the range of 10000-30000 mPa·s.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C6 carbon in cellulose.

The modifications of nanofibrillar cellulose disclosed herein may also be applied to other fibrillar cellulose grades described herein. For example also highly refined cellulose or microfibrillar cellulose may be similarly chemically or enzymatically modified. However, there are differences for example in the final fibrillation degree of the materials.

In one example such chemically modified nanofibrillar cellulose, when dispersed in water, provides a Brookfield viscosity of at least 10000 mPa·s measured at 20° C.±1° C., at a consistency of 0.8% (w/w) and at 10 rpm. In one example such chemically modified nanofibrillar cellulose, when dispersed in water, provides a Brookfield viscosity of at least 15000 mPa·s measured at 20° C.±1° C., at a consistency of 0.8% (w/w) and at 10 rpm. In one example such chemically modified nanofibrillar cellulose, when dispersed in water, provides a Brookfield viscosity of at least 18000 mPa·s measured at 20° C.±1° C., at a consistency of 0.8% (w/w) and at 10 rpm. Examples of anionic nanofibrillar celluloses used have a Brookfield viscosity in the range of 13000-15000 mPa·s or 18000-20000 mPa·s, or even up to 25000 mPa·s, depending on the degree of fibrillation.

In one example the nanofibrillar cellulose is TEMPO oxidized nanofibrillar cellulose. It provides high viscosity at low concentrations, for example a Brookfield viscosity of at least 20000 mPa·s, even at least 25000 mPa·s, measured at 20° C.±1° C., at a consistency of 0.8% (w/w) and at 10 rpm. In one example the Brookfield viscosity of TEMPO oxidized nanofibrillar cellulose is in the range of 20000-30000 mPa·s, such as 25000-30000 mPa·s, measured at 20° C.±1° C., at a consistency of 0.8% (w/w) and at 10 rpm.

In one example the nanofibrillar cellulose comprises chemically unmodified nanofibrillar cellulose. In one example such chemically unmodified nanofibrillar cellulose, when dispersed in water, provides a Brookfield viscosity of at least 2000 mPa·s, or at least 3000 mPa·s, measured at 20° C.±1° C., at a consistency of 0.8% (w/w) and at 10 rpm.

Auxiliary agents for enhancing the manufacturing process or improving or adjusting the properties of the product may be included in the nanofibrillar cellulose dispersion. Such auxiliary agents may be soluble in the liquid phase of the dispersion, they may form an emulsion or they may be solid. Auxiliary agents may be added already during the manufacturing of the nanofibrillar cellulose dispersion to the raw material or they may be added to a formed nanofibrillar cellulose dispersion or gel. The auxiliary agents may be also added to the final product, for example by impregnating, spraying, dipping, soaking or the like method. The auxiliary agents are usually not covalently bound to the nanofibrillar cellulose, so they may be releasable from the nanocellulose matrix. A controlled and/or sustained release of such agents may be obtained when using NFC as matrix. Examples of auxiliary agents include therapeutic (pharmaceutic) agents and other agents affecting to the properties of the product or to the properties of the active agents, such as buffers, surfactants, plasticizers, emulsifiers or the like. In one example the dispersion contains one or more salts, which may be added to enhance the properties of the final product or to facilitate water removal from the product in the manufacturing process. Examples of salts include chloride salts, such as sodium chloride, calcium chloride and potassium chloride. The salt may be included in an amount in the range of 0.01-1.0% (w/w) of the dry matter in the dispersion. The final product may also be dipped or soaked in a solution of sodium chloride, such as in an aqueous solution of about 0.9% sodium chloride. Desired salt content in the final product may be in the range of 0.5-1%, such as about 0.9%, of the volume of the wet product. The salts, buffers and the like agents may be provided to obtain physiological conditions.

Multivalent cations may be included to obtain non-covalent crosslinking of the nanofibrillar cellulose. One example provides a nanofibrillar cellulose product comprising nanofibrillar cellulose, especially comprising anionically modified nanofibrillar cellulose, and multivalent cations, such as multivalent metal cations, for example selected from cations of calcium, magnesium, zinc, aluminum, gold, platinum and titanium, wherein the nanofibrillar cellulose is crosslinked by the multivalent cations. The amount of the multivalent cations may be in the range of 0.1-3% (w/w), for example 0.1-2% (w/w) calculated from the dry content of the hydrogel.

One example provides a method for preparing such a hydrogel, the method comprising providing pulp, disintegrating the pulp until nanofibrillar cellulose is obtained, forming the nanofibrillar cellulose into a hydrogel The nanofibrillar cellulose may be fibrillated into a desired fibrillation degree and adjusted into desired water content, or otherwise modified, so that it forms a gel having desired properties as described herein. In one example the nanofibrillar cellulose in the hydrogel is anionically modified nanofibrillar cellulose.

The hydrogel to be used as a medical or scientific hydrogel needs to be homogenous. Therefore the method for preparing the hydrogel may include homogenizing a hydrogel comprising nanofibrillar cellulose, preferably with a homogenizing device such as ones described herein. With this preferably non-fibrillating homogenizing step it is possible to remove areas of discontinuity from the gel. A homogenous gel having better properties for the applications is obtained. The hydrogel may be further sterilized, for example by using heat and/or radiation, and/or by adding sterilizing agents, such as antimicrobials.

Additive Manufacturing

In one embodiment the forming the at least on barrier comprises preparing the barrier by additive manufacturing. Additive manufacturing, also called as 3D printing, is a process wherein material is joined or solidified under computer control to create a three-dimensional object. This can be carried out without a mold. The material may be added together layer by layer, for example by using one or more nozzles for providing or outputting the material. In one example a ring nozzle is used, which may form a circular or substantially circular barrier in one action, so the nozzle does not have to be moved to form the circle. When using additive manufacturing, it was possible to obtain uniform barriers with good quality, which can be used in tests requiring high quality and uniform materials.

The nanofibrillar cellulose, preferably at the consistency desired in the barrier, is provided to a manufacturing device, such as a 3D printer. The nanofibrillar cellulose may be present as a dispersion or hydrogel having a concentration of 0.8-2.5% (w/w) or 0.8-2.1% (w/w), or the concentration may be lower or higher, and it is provided into a container or in a container, for example a syringe, an ampule, a bottle, a tube, a cassette or the like, which may be designed to be attached to the manufacturing device. However, especially in additive manufacturing it was found that the consistency of the nanofibrillar cellulose hydrogel should be preferably above 1.0% (w/w), such as 1.1-2.5% (w/w), 1.1-2.1% (w/w), 1.4-2.1% (w/w) or 1.5-2.0% (w/w).

When 3D printing nanofibrillar cellulose, the process differs from the convention 3D printing processes. The cellulose does not melt when heated, so the methods and devices used for printing materials such as plastic, metal or the like may not be applicable. A specific manufacturing device may have to be used, such as a syringe-based device, which may utilize one or more syringes. Such a device may handle and print liquid, paste, gel or slurry, so it is suitable for nanofibrillar cellulose hydrogel materials. The manufacturing device may contain software operatively stored in a control unit configured to control the device, or the device may be connected to an external control unit, such as a computer, containing the software.

Nanofibrillar cellulose as shear-thinning or thixotropic material behaves in different way than conventional materials used in additive manufacturing. When shear forces are applied to the material, for example when the material is mixed, pressed and/or forced through a nozzle, the nanofibrillar cellulose gel exhibits thinning behavior which facilitates the flow of the material to the target. However, when the material has been printed or otherwise outputted from the manufacturing device, the viscosity will return back to the previous state of higher viscosity. This may provide challenges when forming the desired barrier structures to a support, but it may also facilitate the 3D printing process and formability of the desired structure. For example the shear thinning or thixotropy of the hydrogel may provide a suitable open time for the material wherein it can be molded and desired structures may be formed. There is usually no need to control the temperature, for example the material does not have to be heated and/or cooled for molding or setting purposes, but the process may be carried out at room or ambient temperatures.

The barrier structures may be manufactured, or printed, onto a support, which may be the cell culture plate or well, or a different or separate support, which may be metal, plastic or other suitable material, or which may be coated with plastic membrane, paper or the like. The manufactured final barrier structure, especially in the form of a structure circumscribing and/or defining an area, such as described herein, for example in ring or circle forms or similar, may be therefore formed directly onto the final location in the well, or the final barrier structure may be picked from the support and applied to the well. The 3D printed final barrier structures may be prepared and stored separately, and they may be provided to be applied to the cell culture wells in the methods disclosed herein.

It may be necessary to dry the outputted material, so the method may contain a drying step. For example vacuum or under pressure, and/or freezing and/or heating may be utilized for forming the structure and/or dewatering it. The drying may be carried out for the final structure only or it may be repeated two or more times. When additive manufacturing is carried out by providing more than one layer, it may be necessary to let the material to dry 10-30 minutes, for example about 15 minutes, before applying a new layer. If the layers are applied manually, for example by using a syringe and injection needle, it may be necessary to let the layer dry for a longer time, such as 30-60 minutes before applying a new layer.

The outputting means, such as nozzle or the like, of the manufacturing device, may also play an important role. One example of the outputting device is a syringe, and it was found out that preferably a new and unused syringe should be used every time. A needle, preferably a metallic needle, may act as the nozzle. The needle may be an injection needle or the like, for example about 16 gauge needle, which has an nominal inner diameter of 1.194 mm or 22 gauge needle, which has an inner diameter of 0.413 mm. In general the nozzle may have an inner diameter in the range of 0.2-3.0 mm, such as 0.2-2.0 mm, for example 0.2-1.5 mm, 0.3-2.0 mm, 0.4-1.5 mm or 0.4-1.3 mm. An injection needle or the like may have a size of for example in the range of 14G-28G, such as 16G-22G.

After the additive manufacturing it may be necessary to let the material, i.e. the barrier, to dry, for example for at least 30 minutes or at least 60 minutes. The barriers may be stored for at least two weeks after manufacture, especially when stored in refrigerator temperature, such as less than 10° C., for example 2-10° C. or 4-8° C.

The method for preparing a cell culture plate by additive manufacturing may comprise
providing a cell culture plate comprising one or more cell culture well(s),
providing an aqueous dispersion of nanofibrillar cellulose,
providing a manufacturing device for additive manufacturing,
forming at least one barrier from the nanofibrillar cellulose into at least one cell culture well for dividing the well into at least two compartments with the manufacturing device. The forming of the at least one barrier may be carried out in one or more steps, such as in two or more steps. Layers or the like partial structures are formed in each step. Between the steps there may be a pause and/or drying step of for example 10-60 minutes, such as 10-30 minutes or 10-20 minutes. The drying step may be carried out in such way and/or for such a time that the desired consistency of the nanofibrillar cellulose is obtained. The obtained cell culture plate may be any of the cell culture plate described herein.

The cell culture plates disclosed herein may be medical products. The term "medical" refers to a product or use wherein the product, i.e. a product comprising the NFC of the embodiments, is used or is suitable for medical purposes or for scientific purposes, for example for research. A medical product may be sterilized, or it is sterilizable, for example by using temperature, pressure, moisture, chemicals, radiation or a combination thereof. The product, preferably the hydrogel with the attached molecule(s), may be for example autoclaved, or other methods using high temperature may be used, in which cases the product should tolerate high temperatures over 100° C., for example at least 121° C. or 134° C. In one example the product is autoclaved at 121° C. for 15 minutes. It is also desired that a medical product is pyrogen free and it does not contain undesired protein residues or the like. A medical product is preferably non-toxic to the target. Also UV sterilization or gamma radiation may be used.

The cell culture plates disclosed herein and/or prepared as disclosed herein may be provided as commercial products, such as packed products, especially a packed medical product. The cell culture plate may be packed in a packing, such as a sterilized packing, or the products may be sterilized in the packing. The cell culture plate may contain a membrane, film or other cover which covers the cell culture well(s). The covered wells are protected from ambient conditions, such as from microbes, humidity, gases, particles and the like during storage, transportation and handling. A cover may be provided or present as a strip, which is attached to the cell culture plate by suitable adhesive. The strip may be removable, for example it may be ripped or peeled off to expose the cell culture well(s), so that the plate is ready to be used. The cell culture plate may contain only the barriers as disclosed herein, for example at the concentration of use, or alternatively as dried. The cell culture plate, or the well(s) may contain protective gas. The cell culture plate may be also provided with storage solution, culture medium and/or gel in the well(s) and/or compartment(s). The cell culture plate may be provided without cells or with cells.

Methods for Studying Cells

The cell culture plates containing the barrier can be used in a variety of scientific and medical methods, such as in methods involving living cells.

In the methods and products for studying cells, certain types of cells are provided. The cells may be prokaryotic cells, such as bacterial cells, or they may be eukaryotic cells. Eukaryotic cells may be plant cells, yeast cells or animal cells. Examples of eukaryotic cells include transplantable cells, such as stem cells. The cells may be animal cells or human cells. The term "cell" as used herein may also include a mixture of more than one types of cells, multicell structures, tissue-like structures and tissues and constructs or materials containing thereof or derived therefrom. The multicell and tissue-like structures, constructs or materials may include cells and other biological and/or biologically compatible material(s), and they may contain cells which are arranged in a desired way. By using such multicell and tissue-like structures or materials it is possible to create and provide a model of a biological system, which can be studied and tested, for example a cardiovascular system, hepatic system, cancer system or the like.

Specific examples of cells include stem cells, undifferentiated cells, precursor cells, as well as fully differentiated cells and combinations thereof. In some examples the cells comprise cell types selected from the group consisting of keratocytes, keratinocytes, fibroblast cells, epithelial cells and combinations thereof. In some examples the cells are selected from the group consisting of stem cells, progenitor cells, precursor cells, connective tissue cells, epithelial cells, muscle cells, neuronal cells, endothelial cells, fibroblasts, keratinocytes, smooth muscle cells, stromal cells, mesenchymal cells, immune system cells, hematopoietic cells, dendritic cells, hair follicle cells and combinations thereof. The cells may be tumor or cancer cells, genetically modified cells, such as transgenic cells, cisgenic cells or knock-out cells, or pathogenic cells. Such cells may be used for example for drug research or in therapy. Especially stem cells may be used in therapeutic applications, for example provided to a patient.

In one example the cells are eukaryotic cells, such as mammalian cells. Further examples of mammalian cells include human cells, mouse cells, rat cells, rabbit cells, monkey cells, pig cells, bovine cells, chicken cells and the like. It is to be noted that even though the advantages of the present methods and products are best demonstrated for studying mammalian cells, the methods and products may be also used for studying other cells, such as non-mammalian eukaryotic cells, yeast cells, or prokaryotic cells.

One or more of the cell culture well(s) may contain the barrier disclosed herein and therefore the well(s) may contain at least two compartments for receiving cells and/or other substances. For example cells of one or more types may be applied to the compartments. In one example the cells applied to two or more compartments in a well are same types of cells. In one example the cells applied to two or more compartments in a well are different types of cells, so that in each compartment there may be different types of cells, or at least in one compartment there are different types of cells than in the other compartment(s). The cell type may refer to the origin of the cell, for example the cells may be from different organism, and/or the cells may represent different tissues. The cells may also be normal or healthy cells or they may be tumor cells, such as cancer cells. Examples of cells which may be applied, incubated, cultured and/or tested in the one or more of the cell culture wells or compartments of the embodiments include liver cells, such as hepatocytes, for example hepatocellular carcinoma cells, endothelial cells, adipose cells, cardiomyocytes, kidney cells, immune cells such as macrophages and monocytes, or nerve cells, such as neuroblastoma cells, stem cells or any other suitable cells.

In one example the cells are stem cells, such as omnipotent, pluripotent, multipotent, oligopotent or unipotent stem cells. Stem cells are cells capable of renewing themselves through cell division and can differentiate into multi-lineage cells. These cells may be categorized as embryonic stem cells (ESCs), induced pluripotent stem cells (iPSCs), and adult stem cells, also called as tissue-specific or somatic stem cells. The stem cells may be human stem cells, which may be of non-embryonic origin, such as adult stem cells. These are undifferentiated cells found throughout the body after differentiation. They are responsible for e.g. organ regeneration and capable of dividing in pluripotent or multipotent state and differentiating into differentiated cell lineages. The stem cells may be human embryonic stem cell lines generated without embryo destruction, such as described for example in Cell Stem Cell. 2008 Feb. 7; 2(2):113-7. The stem cells may be obtained from a source of autologous adult stem cells, such as bone marrow, adipose tissue, or blood.

Examples of stem cells include mesenchymal stem cells (MSC), multipotent adult progenitor cells (MAPCO), induced pluripotent stem cells (iPS), and hematopoietic stem cells.

In case of human stem cells the cells may be non-embryonic cells or cells, such as hESCs, which can be derived without destroying the embryo. In case of human embryonic stem cells the cells may be from a deposited cell line or made from unfertilized eggs, i.e. "parthenote" eggs or from parthenogenetically activated ovum, so that no human embryos are destroyed.

In one example the cells are mesenchymal stem cells (MSC). Mesenchymal stem cells (MSCs) are adult stem cells which can be isolated from human and animal sources, such as from mammals. Mesenchymal stem cells are multipotent stromal cells that can differentiate into a variety of cell types, including osteoblasts, chondrocytes, myocytes and adipocytes. Mesenchyme itself is embryonic connective tissue that is derived from the mesoderm and that differentiates into hematopoietic and connective tissue. However mesenchymal stem cells do not differentiate into hematopoietic cells. The terms mesenchymal stem cell and marrow stromal cell have been used interchangeably for many years, but neither term is sufficiently descriptive. Stromal cells are connective tissue cells that form the supportive structure in which the functional cells of the tissue reside. While this is an accurate description for one function of MSCs, the term fails to convey the relatively recently discovered roles of MSCs in the repair of tissue. The term encompasses multipotent cells derived from other non-marrow tissues, such as placenta, umbilical cord blood, adipose tissue, adult muscle, corneal stroma or the dental pulp of deciduous baby teeth. The cells do not have the capacity to reconstitute an entire organ The International Society for Cellular Therapy has proposed minimum criteria to define MSCs. These cells (a) should exhibits plastic adherence, (b) possess specific set of cell surface markers, i.e. cluster of differentiation (CD)73, D90, CD105 and lack expression of CD14, CD34, CD45 and human leucocyte antigen-DR (HLA-DR) and (c) have the ability to differentiate in vitro into adipocyte, chondrocyte and osteoblast. These characteristics are valid for all MSCs, although few differences exist in MSCs isolated from various tissue origins. MSCs are present not only in fetal tissues but also in many adult tissues with few exceptions. Efficient population of MSCs has been reported from bone marrow. Cells which exhibits characteristics of MSCs have been isolated from adipose tissue, amniotic fluid, amniotic membrane, dental tissues, endometrium, limb bud, menstrual blood, peripheral blood, placenta and fetal membrane, salivary gland, skin and foreskin, sub-amniotic umbilical cord lining membrane, synovial fluid and Wharton's jelly.

Human mesenchymal stem cells (hMSC) display a very high degree of plasticity and are found in virtually all organs with the highest density in bone marrow. hMSCs serve as renewable source for mesenchymal cells and have pluripotent ability of differentiating into several cell lineages, including osteoblasts, chondrocytes, adipocytes, skeletal and cardiac myocytes, endothelial cells, and neurons in vitro upon appropriate stimulation, and in vivo after transplantation.

In one example the cells are multipotent adult progenitor cells (MAPC), which are derived from a primitive cell population that can be harvested from bone marrow, muscle and brain. MAPC are a more primitive cell population than mesenchymal stem cells, whilst they imitate embryonic stem cells characteristics they still retain adult stem cells potential in cell therapy. In vitro, MAPC demonstrated a vast differentiation potential to adipogenic, osteogenic, neurogenic, hepatogenic, hematopoietic, myogenic, chondrogenic, epithelial, and endothelial lineages. A key feature of MAPC is that they show large proliferative potential in vitro without losing their phenotype. MAPC may be used for treating a variety of diseases such as ischaemic stroke, graft versus host disease, acute myocardial infarct, organ transplant, bone repair and myelodysplasia. MAPC also enhance bone formation, promote neovascularisation, and have immunomodulatory effects.

Induced pluripotent stem cells (iPS) are a type of pluripotent stem cell that can be generated directly from adult cells. They can propagate practically indefinitely and may give rise to every other cell type in the body, including neurons, heart, pancreatic and liver cells. Induced pluripotent stem cells can be derived directly from adult tissues and they can be made in a patient-matched manner so they may be provided a transplants without the risk of immune rejection. Human induced pluripotent stem cells are of special interest, and they can be generated from for example human fibroblasts, keratinocytes, peripheral blood cells, renal epithelial cells or other suitable cell types.

Hematopoietic stem cells (HSCs), also called as blood stem cells, are cells that can develop into all types of blood cells, including white blood cells, red blood cells, and platelets. Hematopoietic stem cells are found in the peripheral blood and the bone marrow. HSCs give rise to both the myeloid and lymphoid lineages of blood cells. Myeloid and lymphoid lineages both are involved in dendritic cell formation. Myeloid cells include monocytes, macrophages, neutrophils, basophils, eosinophils, erythrocytes, and megakaryocytes to platelets. Lymphoid cells include T cells, B cells, and natural killer cells. Hematopoietic stem cell transplants can be used in the treatment of cancers and other immune system disorders.

The present application also provides a method for detecting a substance, the method comprising
  providing the cell culture plate disclosed herein comprising a first cell in a first compartment, and
  detecting from another compartment at least one substance.

The method for detecting a substance may also be carried out for evaluating an effect of a substance of interest to a cell. The method for detecting a substance may be a method for detecting a substance secreted by a cell, a method for identifying and/or quantifying a substance capable of causing a reaction in a cell, a method for detecting a substance capable of passing the barrier, or any applicable method disclosed herein wherein the barrier can be used for preventing cells to pass but allowing one or more of other substance(s) to pass. In general detecting may refer to identification, quantifying, qualifying and the like, and it may include also analyzing the detected information, and/or providing a result, which actions may be carried out by using a computerized control unit or the like device.

The present application also provides a method for detecting a substance, such as a method for evaluating an effect of a substance of interest to a cell, the method comprising
   providing the cell culture plate comprising a first cell in a first compartment,
   applying the substance of interest to a compartment, such as to the first compartment,
   incubating the cell for a time sufficient to allow the cell to respond to the substance of interest, and
   detecting from another compartment at least one substance, for example detecting the amount of the at least one substance, such as the substance of interest, a substance secreted by the cell, a reaction product of the substance of interest, or other substance, optionally also detecting the at least substance and/or a reaction of the cell from the first compartment, and
   based on the detected substance(s) and/or the reaction of the cell evaluating the effect of the substance to the cell. If the substance of interest is applied to another compartment than the first compartment, such as to a second compartment, the method may comprise allowing the substance of interest to diffuse to the first compartment through the barrier. The at least one substance may be detected from another compartment than wherein the first cell is located, and/or the at least one substance may be detected from another compartment than wherein the substance of interest was applied. In general one or more substance(s) may be detected from one or more compartment(s). In one example one or more of the detected substances are secreted after a substance has passed at least one barrier in the cell culture plate as a reaction to said passed substance.

In general the "secretion" as used herein may be considered broadly, such as including any release of substance(s) from the cell. Secretion may refer to a regular secretion mechanism of a cell wherein one or more substance(s) are secreted by the cell, for example via porosomes to extracellular space or matrix, for example as a response to a stimulus, which may be chemical, such as the substance of interest disclosed herein, change in the environment or conditions, or mechanical stimulus, electrical stimulus, radiation, light or a combination thereof. Secretion may also include excretion. Examples of secreted substances include proteins, enzymes, hormones, toxins, and cell signalling compounds. Secretion may also include other types of actions wherein one or more substances are obtained from a cell, such as when the cell is disrupted or otherwise weakened or the permeability thereof is adjusted, for example obtained by lysis, mechanical or other disruption, such as by using ultra sound, or the like actions resulting in full or partial disruption of cell and release of substances, cell organelles, cytoplasm and the like. The debris of the cell may not penetrate the barrier but some of the other substances will, so it is possible to separate one or more substances of interest from other material, which may interfere detecting and/or other reactions or cells. In such case the method may include disrupting the cells in one compartment.

One example provides a method for detecting a substance, such as a method for evaluating an effect of a substance of interest to a cell, the method comprising
   providing the cell culture plate comprising a first cell in a first compartment,
   applying the substance of interest to the first compartment,
   incubating the cell for a time sufficient to allow the cell to respond to the substance of interest,
   detecting from another compartment at least one substance, and
   based on the detected substance(s) and/or the reaction of the cell evaluating the effect of the substance to the cell.

Detecting the at least one substance may comprise detecting the amount of the at least one substance, and/or detecting the presence of the at least one substance.

The at least one substance, which is detected, may be the substance of interest, a substance secreted by the cell, preferably as a response to the substance of interest, a reaction product of the substance of interest, for example metabolized by the cell or by an substance secreted by the cell, or other substance. The substance secreted by the cell is preferably secreted as a response to the substance of interest or to a different substance secreted by another cell as a response to the substance of interest.

The substance of interest may be a reagent, a pharmaceutical or a molecule which is tested for its ability to act as a pharmaceutical or other reactive molecule. Therefore the substance of interest may be a suspected substance of interest, pharmaceutical, reagent or the like suspected compound. The substance of interest may also include one or more reagent(s) or other compounds suitable for adjusting pH, nutrition content, salt content and/or other conditions of the cell culture medium, wherein a change in such condition(s) may be used as a stimulus.

The method may also include detecting the at least substance, such as discussed in previous, and/or a reaction of the cell from the first compartment. The reaction of the cell may include one or more substance(s) secreted by the cell, enzyme activity detected from the cell or from the compartment, a change in the appearance, metabolism or other property of the cell, or the like. For example a compartment may be monitored visually, for example by using a camera or other optical device or visual detecting means, to detect one or more changes in visual properties of the cell and/or the compartment. The method may comprise providing an imaging device, such as the camera or other suitable device, arranged to monitor one or more compartment(s) in the cell culture plate and to obtain one or more image(s) from the one or more compartment(s), connected to a control unit arranged to save and/or analyse the one or more image(s) to detect a change in the appearance of the cell and/or compartment. The one or more images may refer to moving images i.e video or a plurality of subsequent still images. The detecting methods and means disclosed herein may be used for detecting cell viability.

A compartment may also be monitored chemically, which includes detecting one or more chemical(s) i.e. substance(s), from the compartment, generally by using one or more detecting means. Detecting the one or more substance(s) from one or more compartment(s) may include taking one or more sample(s) from the one or more compartment(s), such as from the media included in the compartment(s), and analyzing the sample(s), or by using one or more suitable probe(s), tests strips or other detecting means arranged to detect a specific substance, by using one or more suitable indicator(s) arranged to detect a specific substance and/or to cause a detectable reaction corresponding to the specific substance, and detecting the reaction, such as a colour reaction, enzymatic reaction, electrochemical reaction or the like reaction, preferably a reaction which can be detected and/or quantified by using automated means, such as one or more probes, detector(s), imaging device(s) or other suitable electronic means connected to a control unit arranged to analyse the detected reaction and preferably outputting one or more result(s) indicating the presence and/or effect of the substance.

The method may further comprise
providing a second cell in a second compartment,
detecting from the second compartment at least one substance secreted by the second cell and/or the reaction of the second cell, and based on the detected substance(s) secreted by the second cell and/or the reaction of the second cell evaluating the effect of the substance of interest to the first cell and/or to the second cell. The reaction of the second cell may include any response of the second cell to a substance secreted by the first cell.

In one embodiment the well contains one type of cells in one compartment and optionally the same and/or other type(s) of cell(s) in at least one other compartment, such as cells selected from liver cells, such as hepatocytes, for example hepatocellular carcinoma cells, endothelial cells, adipose cells, cardiomyocytes, kidney cells, immune cells such as macrophages and monocytes, or nerve cells, such as neuroblastoma cells, and stem cells. Such arrangement may be used in methods for testing or monitoring metabolites and/or other substances secreted by the cells, which may be further tested with cells and/or other substances located in another compartment. In such way the cells in the first compartment remain in the compartment, as they cannot penetrate or cross the barrier, but only the metabolite or other substance, preferably secreted by the cells, can cross the barrier and enter the second or further compartment(s), where they can contact the cells in the compartment, have an effect to the cell, and/or be detected.

One example provides a method for studying a substance secreted by a first cell, the method comprising
providing the cell culture plate comprising the first cell in a first compartment,
applying to the first compartment a compound causing secretion of a substance, such as a metabolite, from the first cell,
incubating the cells for a time sufficient to allow the substance to be secreted and diffused through the barrier,
studying the substance from the second compartment. A second or a further compartment may contain cells, such as cells of second or further type. Studying the substance may include studying the effect of the substance to the second cell, studying the reaction kinetics of the substance or another substance such as a substance secreted by a second or further cell as a response to the first substance.

One example provides a method for evaluating the effect of a substance secreted by a first cell to a second cell, the method comprising
providing the cell culture plate comprising the first cell in a first compartment and the second cell in a second compartment in a cell culture well,
applying to the first compartment a compound causing secretion of a substance, such as a metabolite, from the first cell,
incubating the cells for a time sufficient to allow the substance to be secreted and diffused through the barrier,
analysing the effect of the substance to the second cell in the second compartment to evaluate the effect of the substance.

The first cell as used herein may refer to a plurality of cells of the first type. Similarly the second cell as used herein may refer to a plurality of cells of the second type. The method may first comprise providing the cell culture plate and providing the first cell(s) and applying the first cell(s) to the first compartment, and/or providing the cell culture plate and providing the second cell(s) and applying the second cell(s) to the second compartment. A cell culture plate containing cells, and optionally any cell culture medium or other material, may be called as a cell system.

It was found out in the experiments that the nanofibrillar cellulose barrier was especially efficient tool to add hepatic metabolism into in vitro test systems. Chemicals may be applied to the hepatocyte compartment, and hepatocytes can metabolize the chemicals before they enter fibroblasts in another compartment through the barrier. Finally cell viability can be analyzed in both sides of the barrier for example by using automated cell culture and analysis system such as Ceii-IQ. For obtaining a commercial product, the construction of the barriers must be standardized as the size of the barrier and the surface area of the distinct compartments should be constant.

The barrier can be also used as a tool in neuronal migration test It was found out that neuronal cells (SH-SY5Y) did not cross the barrier, and the barrier could be removed in a standardized way. Therefore, the barrier system has potency to be used in the neuronal migration test (developmental neurotoxicity). The barriers can be constructed as described herein, and removed for example by tweezers.

Instead of HepaRG cells also (cryopreserved) human primary hepatocytes can be used, whose metabolic activity is best immediately after thawing and does not require several days in culture.

The present disclosure also provides use of the cell culture plate disclosed herein for culturing cells, i.e. in a cell culture method or a method including culturing cells.

The present disclosure also provides use of the cell culture plate disclosed herein in a method for detecting a substance or in a method for evaluating an effect of a substance, such as disclosed herein.

EXAMPLES

Example 1: Nanofibrillar Cellulose as a Biological Barrier Allowing Chemicals but not Cells to Permeate The aim of this study was to investigate whether nanofibrillar cellulose gel could be used to construct barriers, which would prevent passage of cells but would allow passage of chemical compounds through the barrier. Grow-Dex™ was used as nanofibrillar cellulose.

Materials

Test Systems
  Human hepatocellular carcinoma cells HepG2 (ATCC*, #HB-8065™) Final Report CONFIDENTIAL
FICAM CT0065/4 6(16)
  Human neuroblastoma cell line SH-SY5Y (ATCC #CRL-2266™)
  Rat alveolar macrophages NR8383 (ATCC #CRL-2192™)
GrowDex™ Hydrogel for Cell Culture
  GrowDex, 0.65% (UPM, lot 11898) Trials 1-3
  Grow-Dex, 0.65%, anionic, (UPM, lot 11782) Trial 4
  GrowDex (Hydrogel for cell culture), 1.5%, (UPM, lot 11878) Trials 1-3, 5
  GrowDex (Hydrogel for cell culture), 1.5%, (UPM, lot 11911) Trial 4
Reagents
  HepG2 cell culture medium, FICAM's lot HepG2/CT0065-2/MH/1/120217
  SH-SY5Y cell culture medium, FICAM's lot SH-SY5Y/CT0065-4/MH/1/120217
  NR8383 cell culture medium, FICAM's lot NR8383/CT0065/MV/1/240417
  TrypLE Express (Gibco Invitrogen 12604, lot 1664940)
  0.2% trypan blue in isotonic solution, FICAM's lot 0.2% TB/SL/17/310518
  DPBS (Lonza #BE17-513F, lot 5MB178)
  Fluorescein (Sigma #6372, lot 67 43406)
  Fibrinogen (Sigma Aldrich #F3879)
  Sodium Dodecyl Sulfate (SDS) (Sigma #L6026, lot SLBF8724V).
  Cellulase from *Aspergillus niger* (Sigma #C1184, lot SLBP8440V)
Equipment
  Cell culture incubator (37° C., 5.0% $CO_2$) (Esco CLS CeiSafe $CO_2$)
  Positive displacement pipette (Mettler Toledo)
  Inverted microscope (Zeiss Primovert+Axiocam ERe 5s)+digital camera
  96-well plates (Nunc #167008)

Overview of the Study

In the present study, four different GrowDex lots (and two densities) were used to construct barriers of both circular and straight wall shape to divide the cell culture wells into two distinct compartments. Barriers were constructed in 6-well plates (circular barriers), and in 24-well and 48-well plates (straight wall barriers). The properties of the barriers to prevent the passage of cells were tested using three different cell types; hepatoblastoma HepG2 cells, neuroblastoma SH-SY5Y cells and NR8383 macrophages. The properties of the barriers to allow the passage of chemicals were tested using both direct and indirect methods. The trials 1-5 are presented in a chronological order, as the results and experiences obtained in a certain trial were utilized in subsequent trials. In Chapter 7 the most important findings and conclusions are summarized.

Experimental Procedure and Results

Figure 1:
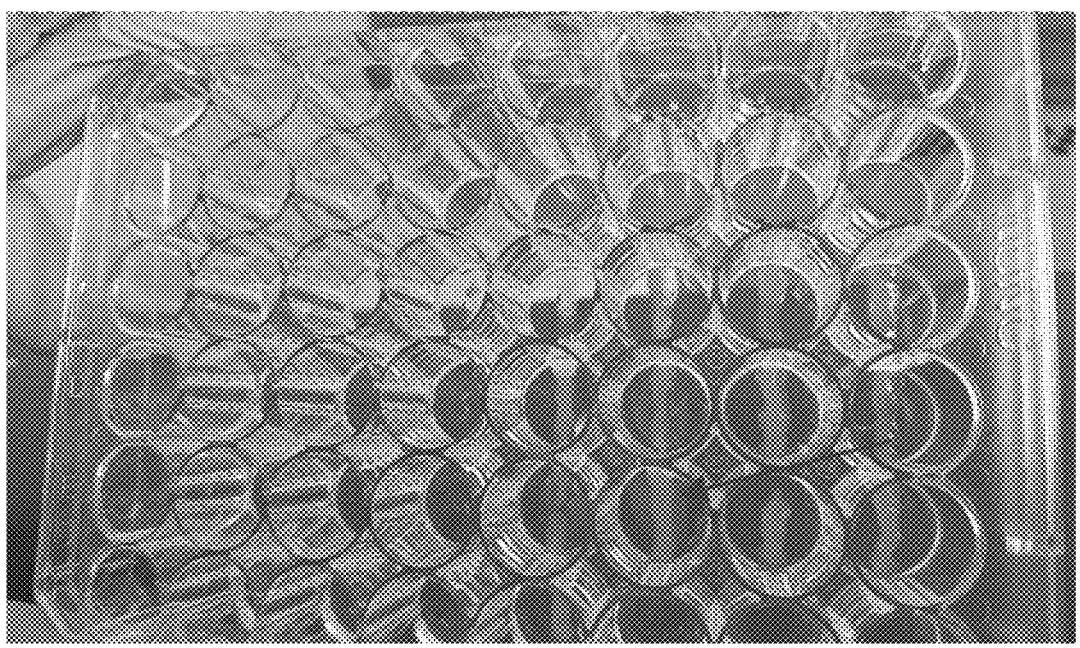
FIG. 1 shows straight wall shaped barriers in a 48-well plate.
Figure 2:
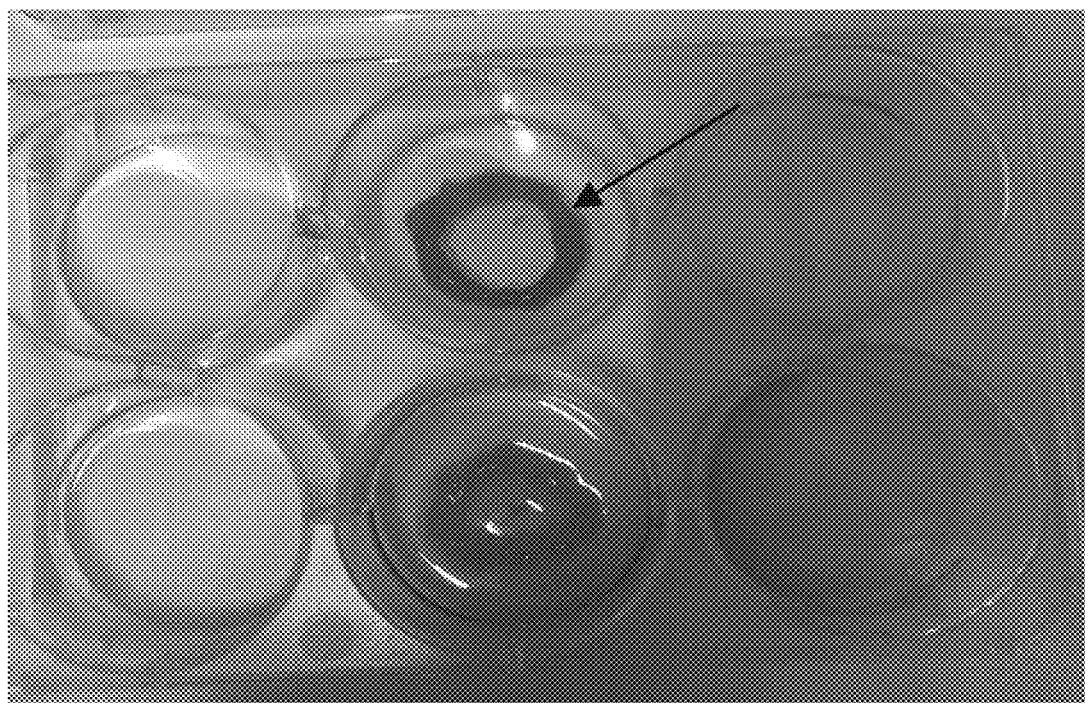
FIG. 2 shows circular shaped barriers in 6-well plate. The upper barrier is constructed of 1.5% GrowDex, lot 11878, the lower barrier is constructed of 0.65% GrowDex, lot 11898. The color comes from the cell culture medium.

Trial No 1: Construction of GrowDex Barriers
  GrowDex: 0.65%, lot 11898, GrowDex 1.5%, lot 11878
Procedure
  Multiple attempts were made to construct barriers in 6-well plates and 24- and 48-well plates. In 24- and 48-well plates the wells were divided into two parts using straight wall barrier structures (FIG. 1). In 6-well plates, circular structures were constructed (FIG. 2). Some barriers were constructed using specific fibrinogen based coating as a glue. To help the construction of the barriers, the shape of barrier was first drawn on the bottom of the multi-well plate.

Results

It appeared that 0.65% GrowDex, lot 11898, was not suitable for constructing barriers. The gel was spread on the bottom of the well, and it was not possible to construct walls that would be high enough to function as barriers. With 1.5% GrowDex instead, it was possible to construct barriers, both circular and straight wall shaped.

Trial No 2: The Passage of SH-SY5Y and HepG2 Cells Through the Barrier
  GrowDex 1.5%, lot 11878
Procedure
  SH-SY5Y cells: Straight wall shaped GrowDex barriers were constructed in 48-well plates as shown in FIG. 1. The barrier constructs were allowed to dry for 1 hour in the laminar hood with the lid open. 325 000 SH-SY5Y cells in 50 µl of cell culture medium were pipetted to the left side of the barrier. Next day cell culture medium was added to both sides of the barrier. Medium was added gradually to prevent the medium flow over the barrier. The cells were grown for up to two weeks. Fresh medium was added twice a week.

HepG2 cells: Circular shaped GrowDex barriers were constructed in 6-well plates as shown in FIG. 2. The barriers were allowed to dry for 1 hour in the laminar hood with the lid open. 1 07 500 HepG2 cells in 50 µl cell culture medium was added inside the barrier. Next day cell culture medium was added to both sides of the barrier. Medium was added gradually to prevent the medium flow over the barrier. The cells were grown for up to two weeks. Fresh medium was added twice a week.

Results
  SH-SY5Y and HepG2 cell populations proliferated and filled their compartment but did not pass the barrier.

Trial No 3: The Passage of Chemicals Through the Barrier
  GrowDex 1.5%, lot 11878
Procedure
  Barriers were prepared in 6-well (circular shaped barriers) and in 24-well (straight wall shaped barriers) plates, and allowed to dry overnight. The barriers were high enough to prevent passage and mixing of the solutions over them. All passage and mixing had to occur through the barriers.

Barrier permeability to chemicals was tested by visual inspection using 0.2% Trypan blue, by quantitative measurement using 1 mg/ml fluorescein solution, and by indirect method using sodium dodecyl sulfate (SDS), which is a toxic compound.

Procedure
0.2% Trypan Blue Permeability
  400 µl Dulbecco's PBS/well was added to the 24-well plates. The plates were incubated for 1 hour at room temperature to moisturize the GrowDex barrier. The DPBS was removed and replaced with 100 µl 0.2% Trypan blue on the left side of the barrier, and with an equal amount of DPBS on the right side of the barrier. It was ensured that the solutions did not go over the barrier.

1 mg/ml Fluorescein Permeability
  The barriers constructed in 24-well plates were first moisturized with DPBS as explained above. Then DPBS was removed and 1 00 µl 1 mg/ml Fluorescein was added to the left side of the barrier, and 1 00 µl DPBS was added to the right side of the barrier. At 1 hour, 3 hours and 3 days after adding the Fluorescein solution, 50 μl samples were collected from both sides of the barrier to 96-well plates, and the absorbance was read at 515 nm. Also a 50 μl sample of the 1 mg/ml Fluorescein was measured. This represented the absorbance in the left side of the barrier at dosing.

SDS Permeability

SDS is a detergent that is known to be toxic to all cell types. The aim of this test was to investigate whether SDS, dosed to one compartment only, is able to cross the Grow-Dex barrier, and hence, kill the cells in both compartments. Circular shaped barriers were prepared in 6-well plates, and straight wall shaped barriers in 24-well plates. SH-SY5Y cells were seeded to the 24-well plate in both sides of the barriers in their normal cell culture medium at the density of 325 000 cells/50 μl. HepG2 cells were seeded to the 6-well plate both inside the barrier circles and outside of them at the density of 107 500 cells/50 μl. Next day 0.4 mg/ml SDS stock was prepared and the cells were exposed to it:

SH-SY5Y cells growing on the 24 well plate: 100 μl of 0.4 mg/ml SDS solution was pipetted to the left side of the barrier. 100 μl medium without SDS was pipetted to the right side of the barrier.

HepG2 cells growing on the 24-well plate: 400 μl of 0.4 mg/ml SDS solution was pipetted inside the circle, and 400 μl of medium without SDS was pi petted outside of the circle.

The cells were incubated for 48 hours in the cell culture incubator. The cell viability was observed microscopically.

Results 0.2% Trypan Blue Permeability

Figure 3:
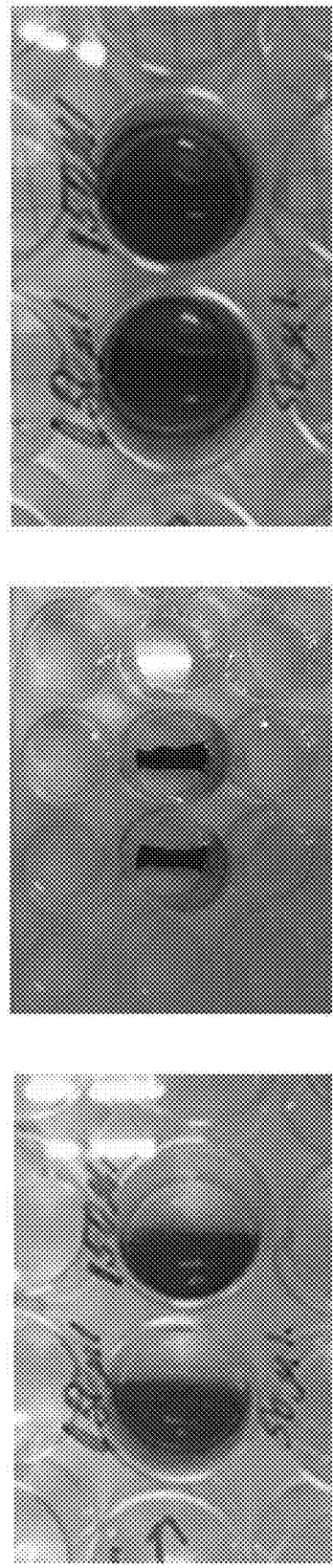
FIG. 3 shows the distribution of 0.2% Trypan Blue in the wells divided with GrowDex barriers.

After six hours the GrowDex barrier had absorbed most of the blue color. Next day the color was evenly distributed on the both sides of the barrier. FIG. 3 shows the distribution of 0.2% Trypan Blue in the wells divided with GrowDex barriers.

Fluorescein Permeability

Absorbance measurements showed that the fluorescein dosed to the left side of the barrier permeated the GrowDex barrier. After one hour 47% of the fluorescein was recovered in the left side, and ca 10% in the right side. Two hours later 52% was recovered in the left side and 35% in the right side. After three days 50% was recovered in the left side and 40% in the right side. The un-recovered. Fluorescein was probably in the GrowDex barrier. All in all, the results show that Fluorescein permeates the barrier within few hours after dosing.

Sodium Dodecyl Sulfate Permeability

SH-SY5Y-cells: 24 hours after SDS dosing all SH-SY5Y cells in the left side of the barrier were dead. In the right side cells were dead next to the barrier, but not all over the well. 48 hours after SDS dosing all cells were dead in both compartments. Similarly, 24 hours after dosing all HepG2 cells were dead inside the GrowDex circle, and also outside of the circle next to the GrowDex barrier. 48 hours later almost all HepG2 cells (about 95%) had died also outside of the circle.

This is an indirect proof that SDS can permeate the barrier.

Trial No 4: The Passage of NR8383 Macrophages Through the Barrier

GrowDex 1.5%, lot 11911, GrowDex 0.65% (anionic), lot 11782

Procedure

Figure 4:
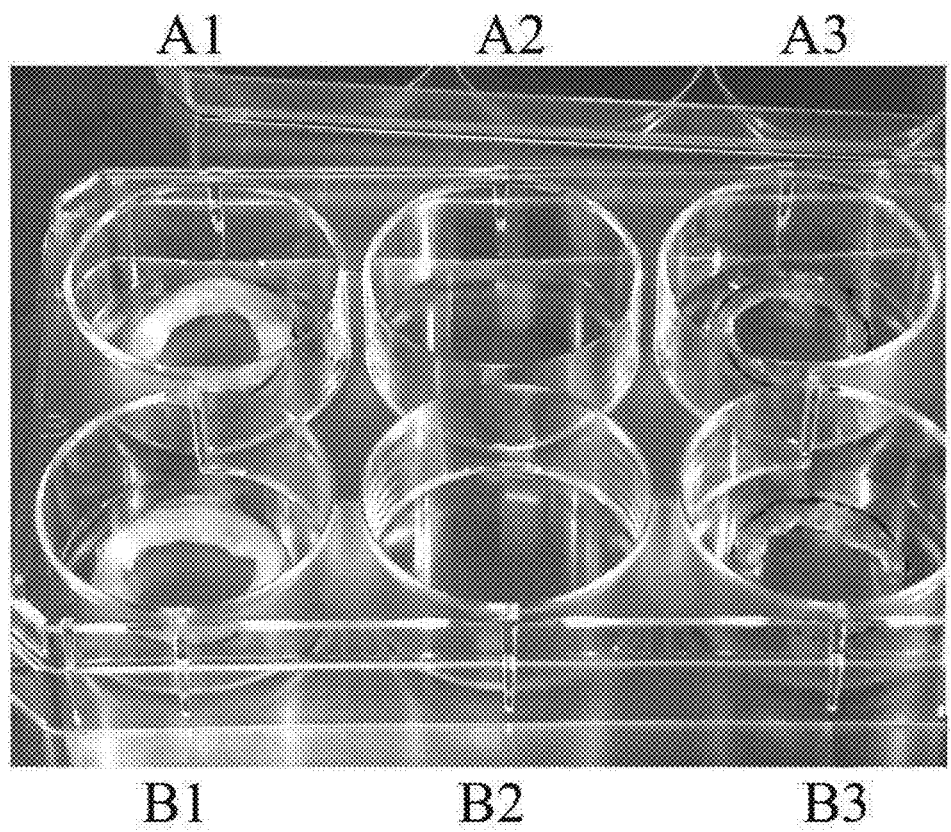
FIG. 4 shows 1.5% GrowDex barriers constructed to wells A1 and B1, 0.65% GrowDex barriers constructed to wells A3 and B3.
Figure 5:
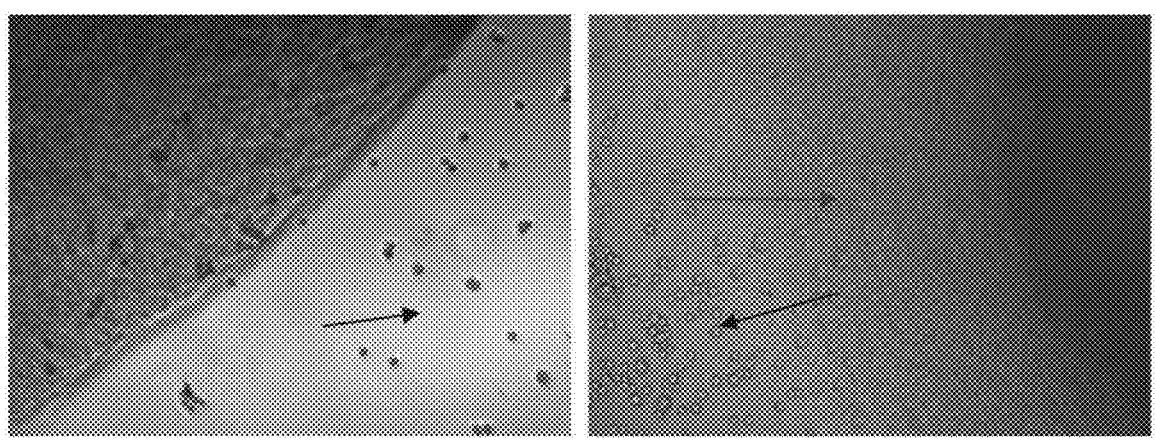
FIG. 5 shows 100× magnification of NR8383 cells migrating towards 1.5% GrowDex barrier. Red arrow points to the barrier. Black arrow points to the inner side of the barrier (no GrowDex) where cells were applied.

Circular shaped barriers were prepared on a 6-well plate as follows: In wells A 1 and B1 1.5% GrowDex (lot 11911) was used. In wells A3 and 83 0.65% GrowDex (lot 11782) was used (FIG. 4). Each barrier was constructed using 3×250 μl=750 μl GrowDex. Constructing the barrier was easier with 1.5% GD than with 0.65%. The latter tended to spread. After pipetting the barriers, they were allowed to dry in the laminar hood with the lid open.

30 000 NR8383 macrophages were added in 50 μl to the middle of the circle and allowed to attach for 30 minutes. Then 150 μl cell culture medium was added inside the circle and 300 μl outside the circle. The medium was added gradually to ensure that it did not go over the barrier. The cell-cultures were maintained and photographed for 3 days. Fresh medium was replaced every day both inside and outside of the barrier.

Results

The barrier construct seemed to attract the macrophages, as on day 2 after seeding of the cells, there were almost no cells in the middle of the circle (where the cells were seeded), and most of the cells were migrating towards the GrowDex barrier. On day 3 the cells were located on innermost zone of the barrier. The effect was the same with both barrier constructs (0.65% and 1.5%) (FIGS. 5-8).

Figure 6:
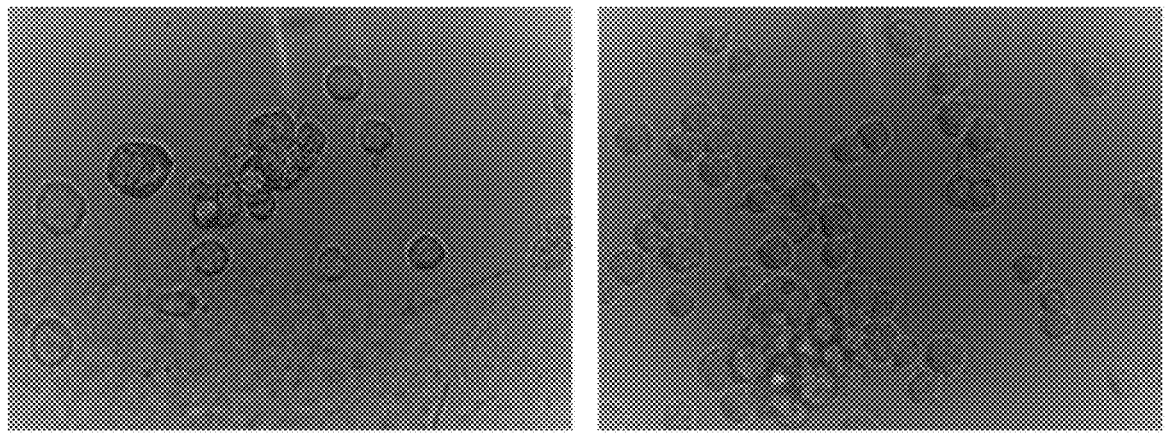
FIG. 6 shows 400× magnification. Left: NR8383 cells migrating towards the 1.5% GrowDex barrier. Right: NR8383 cells in the GrowDex barrier.
Figure 7:
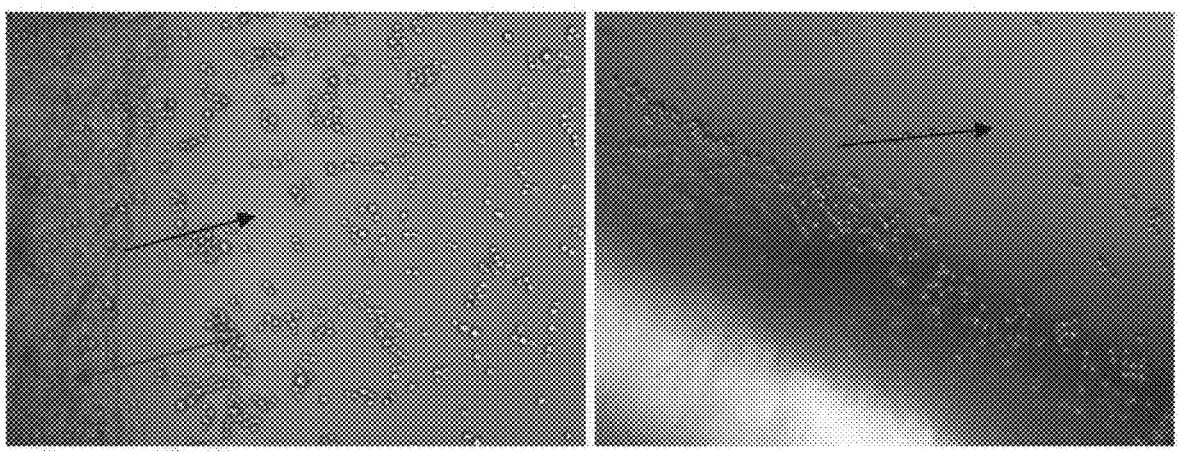
FIG. 7 shows NR8383 cells migrating towards the 0.65% GrowDex barrier. Black arrow points to inner side of the barrier (cells not attached to GrowDex) where cells were applied. Red arrow points to the barrier.
Figure 7:
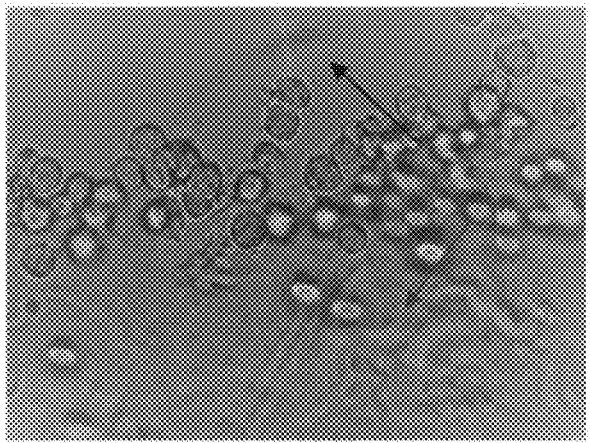
Figure 8:
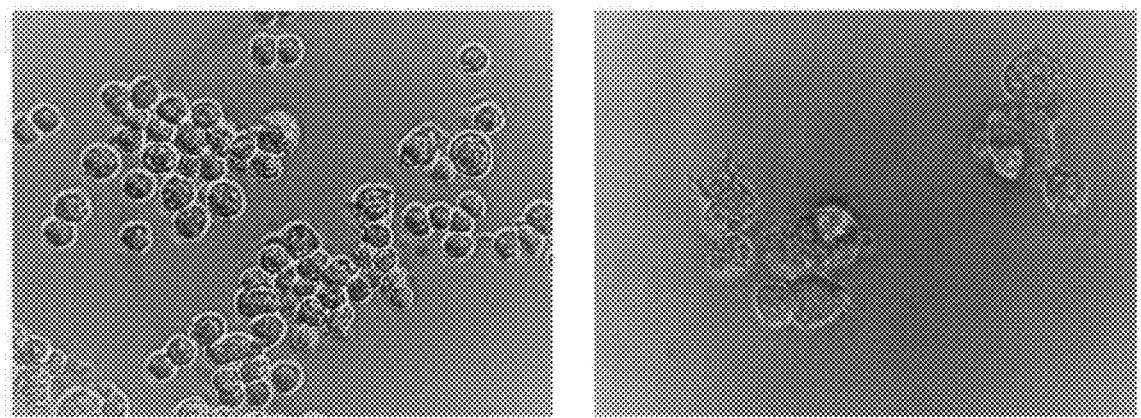
FIG. 8 shows 100× magnification. Left: NR8383 cells in the inner side of the 0.65% GrowDex barrier (cells not attached to GrowDex) where they were pipetted. Right: NR8383 cells in the 0.65% GrowDex barrier.

The cells did not cross the 1.5% GrowDex barrier, rather congregated along the boundary (inner side) (FIGS. 6 and 7).

Figure 9:
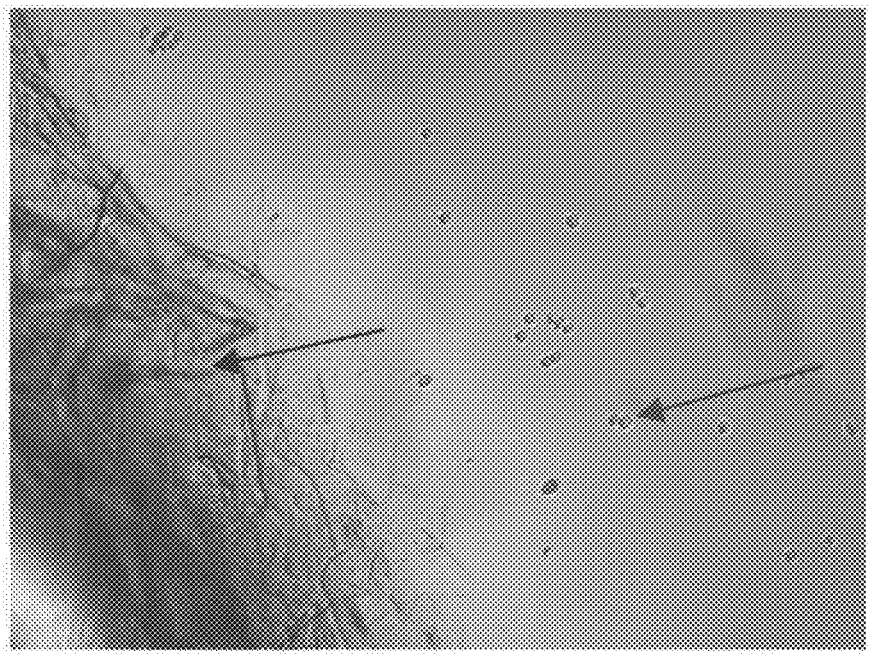
FIG. 9 shows 100× magnification of NR8383 cells in the outer side of the 0.65% GrowDex barrier (blue arrow). Red arrow points to the barrier.

0.65% GrowDex barrier seemed more accessible to the cells than the 1.5% GrowDex, and after three days cells were found to be outside of the 0.65% GrowDex barrier (FIG. 9). This may be due to physical breakdown of the barrier, and/or passage of cells and medium over the barrier, as the construct was quite diffuse as compared to the 1.5% GrowDex.

Trial No 5: Cellulase Treatment

Procedure

At the end of the experiments trials to remove the 1.5% GrowDex barriers with cellulase treatment were carried out. 10 mg/ml and 100 mg/ml cellulase solutions were prepared and the wells containing GrowDex barriers were filled with the cellulase solutions. The plates were incubated in cell culture incubator for 24 hours.

Results

The cellulase solutions did not break down the barriers within 24 hours.

Conclusions

Can biological barriers be constructed of GrowDex?
1.5% GrowDex, both lots 11878 and 11911, could be used to construct barriers. Instead, the composition of 0.65% GrowDex (both lots 11782 and 11898) was too diffuse to construct barriers that would remain intact and preserve the structure. The hydrogel tended to spread on the bottom of the wells.

Circular barriers worked best in 6-well plates, and straight wall shaped barriers worked best in 24- and 48-well plates. Circular barriers were easier to construct as there were no (potentially leaking) joints between the plastic wall and the GrowDex barrier.

Drying the barriers for 1 hour prior to cell seeding seemed to stabilize the barrier. If barriers were dried for a longer time, i.e., overnight, they had to be moisturized for 1 hour prior to use. Otherwise cell seeding was difficult because the barrier absorbed quickly all the medium from the cells.

Do the cells cross the barrier?

The barriers constructed of 1.5% GrowDex did not allow cells to pass: HepG2 and SH-SY5Y cells stayed and proliferated in the compartment where they were applied to. Macrophages did not cross the 1.5% Grow-Dex barrier either, but it seemed that they recognized the gel as a "foreign substance", moved towards it with amoeboid movements, and started to engulf it: The morphology changed from round distinct cells (in the middle of the circle) to cells with projections stretching out when they approached the GrowDex barrier, and when they had entered the GrowDex gel.

Cell seeding worked best when cells were first applied in a small volume of medium avoiding contact with the barrier, and after a 30 minutes attachment period more medium was added.

Do chemicals cross the barrier?

The barriers constructed of 1.5% GrowDex allowed chemicals to pass as shown both with direct and indirect methods.

Is barrier stabile and commercially viable?

The 1.5% GrowDex barriers that were prepared on uncoated multi-well plates were stabile for a week. Thereafter they started to detach. The barriers that were prepared on multi-well plates coated ("glued") with fibrinogen-based coating, were stabile for up to three weeks.

Additional Results

Trials to remove the 1.5% GrowDex barriers with cellulase treatment were not successful. However, the barriers could be removed completely with tweezers.

Example 2: Co-Culture of HepaRG Cells and BJ Fibroblasts Separated by Nanofibrillar Cellulose Barrier to Investigate Metabolism-Dependent Toxicity of Drugs Hepatocytes are the main metabolizing components in the body. Every in vitro test should include testing with and without hepatic metabolism in order to find out whether the substance itself is toxic (without metabolism) or whether the substance is metabolized to reactive and toxic intermediate(s). In order to study metabolism-induced toxicity, researchers often use "conditioned medium"; hepatocytes are first treated with chemicals and this "conditioned" medium is then transferred onto target cells. This is, however, laborious and does not mimic in vivo situation. Therefore, there is a need for simultaneous non-toxic coculturing of hepatocytes and target cells.

The aim of this study was to develop a test model, where drug-metabolism is included in cytotoxicity assessment: Drug-metabolizing component (hepatocytes) was separated from the target BJ cells by a barrier constructed of Grow-Dex. The barrier allow chemicals to pass, but not cells. (In our previous experiments, it was showed that 1.5% Grow-Dex can be used to construct barriers with such features.) Test compounds were dosed into hepatocyte compartment and viability of BJ cells and hepatocytes was measured after exposure.

Materials

Test Systems
  Human fibroblast BJ (Cat No. HB-8065) purchased from ATCC (FICAM's lot 1-BJ/13) and HepaRG cells (#HPRGC10, lot 1919332, see Appendix 1 for the certificate of Analysis) purchased from Thermo Fisher (Life Technologies) were used in this study.
GrowDex Hydrogel for Cell Culture
  GrowDex, 1.5% lot 119923917h
  GrowDex, 2.0% lot 119694117
Reagents
  BJ cell culture medium (MEM with 1% NEAA, 1% L-glutamine and 10% FBS), FICAM's lots BJ-test2/VM0013/MPE/1/080318, BJ-test2/VM0014/MPE/1/160418, BJ/CT0065/8/MPE/2/19032018, BJ/CT0065/8/MV/3/270318, BJ/CT0065/MPE/3/070618, BJ/CT0065/8/MH/4/280418, BJ/CT0092/MPE/2/030618, 5% FBS/BJ/CT0065/8/MV/1/270318, 5% FBS/BJ/CT0065/8/MH/2/290418, BJ/CT0065/9/MV/2/200518, BJ/CT0065/13/MV/1/110718
  BJ chemical dilution medium (MEM with 1% NEAA, 1% L-glutamine, 200 IU/ml penicillin, 200 µg/ml streptomycin) FICAM's lots aBJ/CT0065/8/MV/1/270318, aBJ/CT0065/8/MH/2/290418
  TrypleExpress (Gibco Invitrogen, #12604, lot 1897182)
  0.2% Trypan Blue in isotonic solution, FICAM's lot 0.2%TB/HMä/19/100418
  Williams E Medium with GlutaMAX™ (Invitrogen #32551, lot 1908835)
  HepaRG® Thawing/Plating/General Purpose Medium Supplement (Thermo Fisher Scientific, #HPRG670, lot 1919478)
  HepaRG TOX Medium supplement (Gibco #HPRG630, lot 1912376)
  WST-1 (Takara #MK400, lot AH8P001)
  24-well plates (no coating)
Test Items
  The test item are shown in Table 1. The supplier was Sigma Aldrich.

TABLE 1

The test items

| CHEMICAL | CAS | #CAT/lot | TOXIC METABOLITES | SOLVENT |
| --- | --- | --- | --- | --- |
| Selegiline hydrochloride | 14611-51-9 | 50360000/1.3 | L-metamphetamine, L-amphetamine | Chemical dilution medium |
| Paracetamol | 103-90-2 | A7085/SLBM5923V | N-acetyl-p-benzoquinone imine (NAPQI) | Chemical dilution medium |

Equipment
  Varioskan Flash Multimode Reader Thermo Scientific
  Positive displacement pipette

EXPERIMENTS

General
  The experiments performed are presented here as Experiment 1, 2, 3 and 4. In Experiment 1 the toxicities of paracetamol and selegiline to BJ fibroblasts as such, were investigated. In Experiments 2 and 3 BJ fibroblasts were exposed to paracetamol and selegiline via HepaRG cells Experiment 4 describes the assessment of the metabolic capacity of HepaRG cells.

Culturing Cells for Experiments

The culturing of human BJ fibroblasts started always 1-2 weeks before the experiments. BJ cell culture medium (routine cell culture medium) was prepared according to SOP/M/0001-2.2, and the cells were cultured according to SOP/M/0074-1.0. BJ cells were sub-cultured at least twice before seeding to the experiment. Preparation of HepaRG media and culturing of HepaRG cells were performed strictly according to manufacturer's instructions.

Cell Viability/Cytotoxicity Assay

Cell viability/cytotoxicity was always investigated using WST-1 assay. The assay principle is based on the conversion of the tetrazolium salt WST-1 into a colored dye by mitochondrial dehydrogenase enzymes. The soluble salt is released into the media. Within a given time period, the reaction produces a color change which is directly proportional to the amount of mitochondrial dehydrogenase in a given culture. As a result, the assay actually measures the net metabolic activity of cells. Theoretically, this is reflective of cell number the more cells, the more dehydrogenase available to reduce the reagent.

Experiment 1 (Toxicity of Selegiline and Paracetamol to BJ)

Aim

The aim of Experiment 1 was to investigate the toxicity of paracetamol and selegiline to BJ fibroblasts as such, without HepaRG-treatment.

Procedure

Seeding of BJ Cells

BJ cell suspension was prepared at a density of 40 000 cells/ml in BJ cell culture medium. 100 µl of this suspension was pipetted to a 96-well plate resulting in 4000 cells/well.

Preparation of Selegiline and Paracetamol Dilutions

Selegiline and paracetamol dilutions were prepared on the day of use. First, 1 mg/ml stocks were prepared from both drugs, then 200 and 20 µg/ml dilutions were prepared from paracetamol stock, and 200, 20, 10, 5 and 2 µg/ml dilutions from selegiline stock. The stocks and dilutions were prepared in BJ chemical dilution medium. Selegiline toxicity was studied more extensively than paracetamol, because there was no previous data of selegiline toxicity to BJ fibroblasts. Instead, paracetamol toxicity to human BJ fibroblasts has been extensively studied.

Exposure

BJ cell culture medium was removed from the cells by dumping and blotting the plate carefully on sterile towel. Immediately, 50 µl BJ cell culture medium was added to all wells, and then 50 µl test item dilutions (selegiline or paracetamol) or 50 µl vehicle control. Hence the final drug concentrations in the wells were 500, 100, 10, 2.5 and 1 µg/ml. BJ chemical dilution medium was used as vehicle control. Two similar 96-well plates were prepared for both drugs with six parallels of each concentration and vehicle control on each plate. One of the plates was incubated for 3 hrs and the other for 20 hrs.

Cytotoxicity/Viability Assay

After the 3-hours or 20 hrs incubation, 10 µl WST-1 reagent was added into the wells. The plate was incubated for 2 hrs, thereafter absorbance was read at 450 nm.

Data Handling

Blank values (contained all reagents, including drugs, but no cells) were subtracted from the absorbance data. The results were given as percentage of viable cells as compared to untreated (vehicle) control. The statistical difference between untreated control and treated cells was assessed using t-test (SigmaPlot).

Results

The effect of selegiline and paracetamol on the viability of human BJ fibroblasts is presented in FIG. 1. The highest selegiline concentration, 500 µg/ml, reduced BJ cell viability ~10% in both 3 and 20 hrs exposures. The lowest selegiline concentrations, in turn, increased BJ fibroblast viability ~10%. Paracetamol did not reduce the viability of BJ fibroblasts, but the highest paracetamol concentration, 500 µg/ml, increased BJ cell viability ~9% in the 3 hrs exposure.

Conclusions

Figure 10:
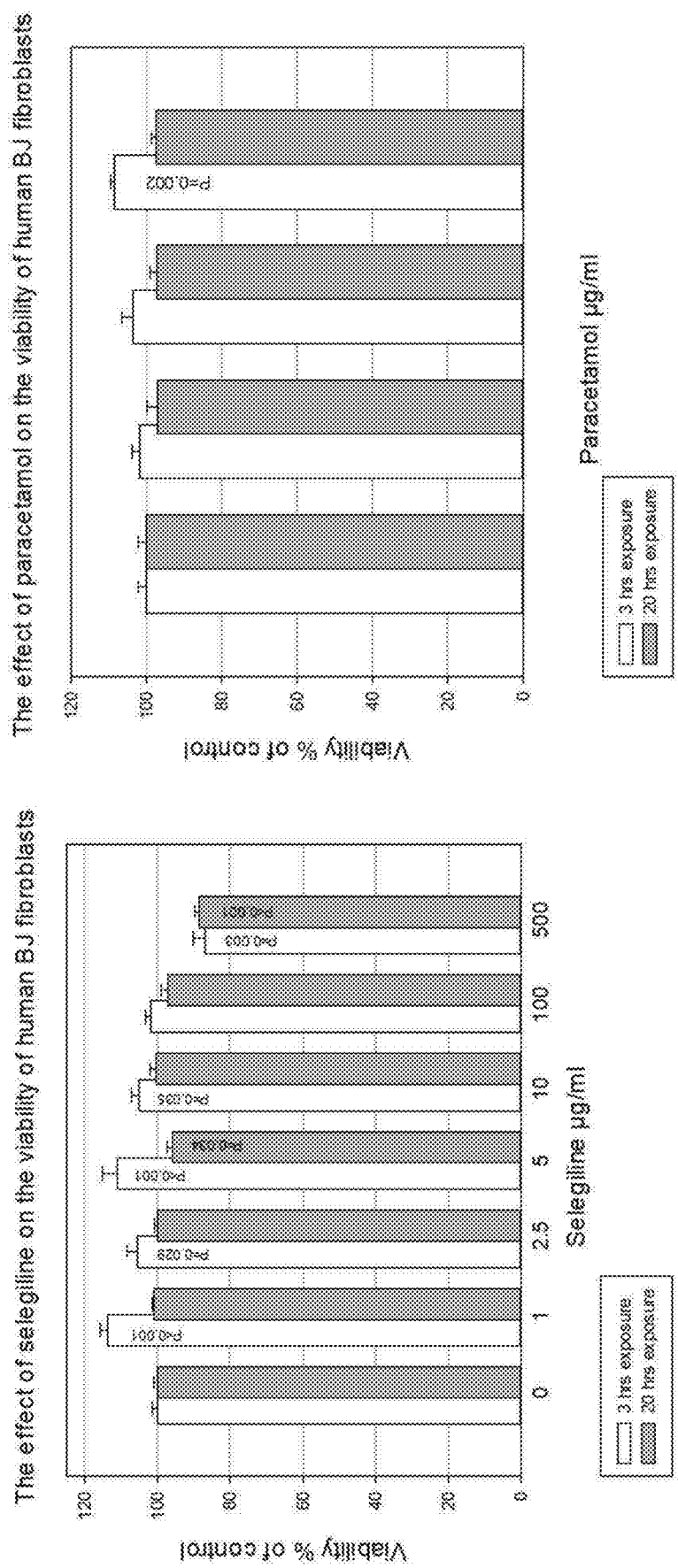
FIG. 10 shows the effect of selegiline and paracetamol on the viability of human BJ fibroblasts.

The exposure of BJ fibroblast monocultures to selegiline and paracetamol revealed that these drugs as such are not toxic to BJ fibroblasts. These results gave a base for further experiments where metabolism-dependent toxicity of selegiline and paracetamol using a co-culture of BJ fibroblasts and metabolizing hepatocytes separated by GrowDex barrier was to be investigated. The effect of selegiline and paracetamol on the viability of human BJ fibroblasts are shown in FIG. 10. Each bar represents MEAN±SEM, N=6-12. Statistical differences were investigated using t-test (Sigma Plot).

Experiment 2 (Toxicity of Selegiline to BJ when Exposed Via HepaRG Cells)

Aim

The aim of Experiment 2 was to investigate whether the proposed test method, i.e, co-culturing HepaRG cells (metabolizing component) and BJ fibroblasts (target cells) in wells of a 24-well plate separated by GrowDex barrier, can be used to recognize the metabolism-dependent toxicity of drugs. Selegiline, which is known to become more toxic via hepatic metabolism, was used as a test compound. It was dosed to the HepaRG cells, and viability of HepaRG and BJ cells was measured after 3 hours.

Procedure

Preparation of GrowDex Barriers 1.5% GrowDex

Figure 11:
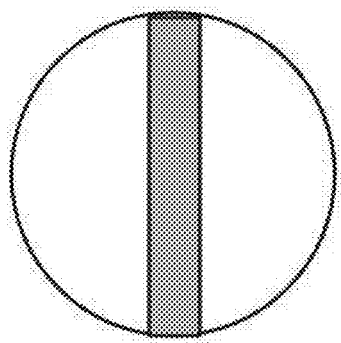
FIG. 11 shows a schematic example of a well divided into two equally sized compartments with a barrier of nanofibrillar cellulose.

GrowDex barriers were prepared to split the wells of a 24-well plate into two equally sized compartments (the grey area represents GrowDex barrier), as shown in FIG. 11.

Two different methods were used to prepare barriers.

1) 250 µl GrowDex was pipetted to the wells (using positive displacement pipette) to construct the first layer of the barrier, the barrier was allowed to dry with the lid closed for 1 hour at room temperature. Then a second layer of GrowDex was pipetted on the top of the first layer. Eight barriers were prepared using this method. 2) 250 µl+250 µl GrowDex was added to the wells (see picture above) without drying between layers. Four barriers were prepared using this method.

After constructing the barriers, they were allowed to dry for 1 hour with the lid off at room temperature in the laminar hood. Thereafter the plates were sealed with parafilm and transferred to the fridge (~+4° C.) to be used next day in the experiments.

2.0% GrowDex

Transparent 2.0% GrowDex was also used to construct barriers. The barriers were constructed as described above (1). At 2.0% this GrowDex was, however, so rigid that it was not possible to construct barriers without "boulders and bubbles". This composition allowed both medium and cells pass from one side to the other, and therefore did not serve the intended purpose. In order to reduce the rigidity, the 2.0% gel was diluted with water gradually as follows:

50 µl $H_2O$ was added per 1 ml 2.0% GrowDex—~1.9% GrowDex

+100 µl $H_2O$→~1.7% GrowDex

+200 µl $H_2O$→~1.5% GrowDex

Inbetween dilutions GrowDex was mixed with pipette tip.

Figure 12:
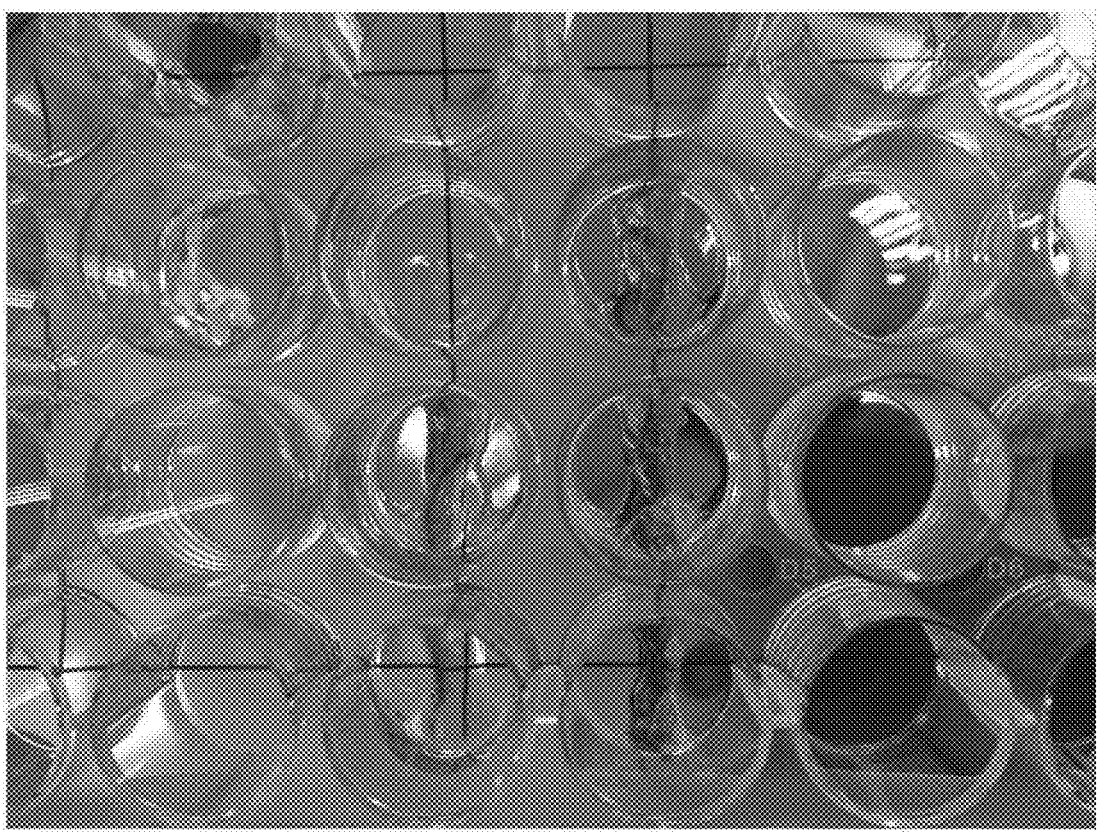
FIG. 12 shows barriers prepared using bright GrowDex. The three "pink" barriers in the column on right: 2.0% GrowDex. The two "pink" barriers on left: ~1.7-1.9% GrowDex. The two wells without pink medium (up left): ~1.5% GrowDex.

Diluting 2.0% GrowDex helped to construct barriers with a more homogenous structure. On the other hand the barriers were "loose", and seemed to dissolve when medium was added to the wells. Hence, these barriers could not be used in the experiments, and no further trials with the transparent 2.0% GrowDex were carried out. FIG. 12 shows barriers prepared using bright GrowDex. The three "pink" barriers in the column on right: 2.0% GrowDex. The two "pink" barriers on left: ~1.7-1.9% GrowDex. The two wells without pink medium (up left): ~1.5% GrowDex Seeding of BJ Cells Next day the barriers were moisturized for one hour before BJ cell seeding by adding 200 µl BJ cell culture medium to both sides of the barrier.

BJ cell suspension was prepared at a density of 40 000 cells/ml BJ cell culture medium. The medium was removed from the right side of the barrier, and replaced by 150 µl of BJ suspension resulting in 6000 BJ cells/well. The plate was gently swirled to distribute the cells evenly. Then 50 µl BJ cell culture medium was added on the top of the cells carefully making sure that there was no medium flow over the barrier.

Next day before seeding HepaRG cells, the medium of BJ cells was changed: The old medium was removed by careful pipetting and replaced by 200 µl BJ cell culture medium supplemented with 5% FBS.

Seeding of HepaRG Cells

Next day after seeding BJ cells, the wells were observed under microscope. It was noticed that 4 of the 12 barriers had leaked as BJ seeded to right side of the barrier were found also in left side of the barrier. The experiment went on, however, without rejecting any of the wells at this point.

HepaRG suspension was prepared at a density of 2 million HepaRG cells/ml HepaRG® Thawing/Plating/General Purpose Medium 670. Medium was removed from the left side of the barrier, and then 200 µl HepaRG suspension, i.e., 400 000 cells was added to each well.

Figure 13:
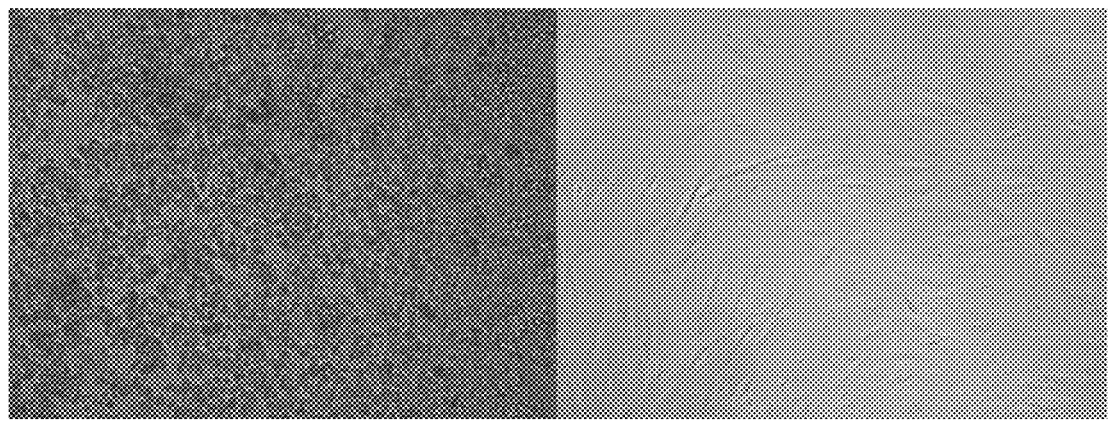
FIG. 13 shows HepaRG cells photographed in left side of the barrier (left) and BJ fibroblats photographed in the right side of the barrier (right).

The plate was gently swirled in back-and-forth and side-to-side manner and the homogeneity of the cell distribution was ensured visually (FIG. 13). The plate was placed back into cell culture incubator and the cells were let to recover for 4 hrs before exposure.

Preparation of Selegiline Dilutions

Selegiline dilutions were prepared on the day of use. First, 1 mg/ml selegiline stock was prepared in HepaRG TOX medium. Then 20 µg/ml, 10 µg/ml and 2 µg/ml selegiline dilutions were prepared using the stock and HepaRG TOX medium. HepaRG TOX Medium alone served as vehicle control.

Exposure

Medium was carefully removed from the HepaRG cells (left side of the barrier), and replaced with 100 µl/well HepaRG TOX Medium/well. This was performed one well at a time.

After changing the medium to all wells, 100 µl selegiline dilutions and vehicle control was added on the top of HepaRG cells. Final selegiline concentrations were hence 0.5× the concentrations of the dilution used, i.e. 10 µg/ml, 5 µg/ml and 1 µg/ml. The cells were incubated for 3 hrs before WST-1 assay.

Cytotoxicity/Viability Assay (WST-1)

Figure 14:
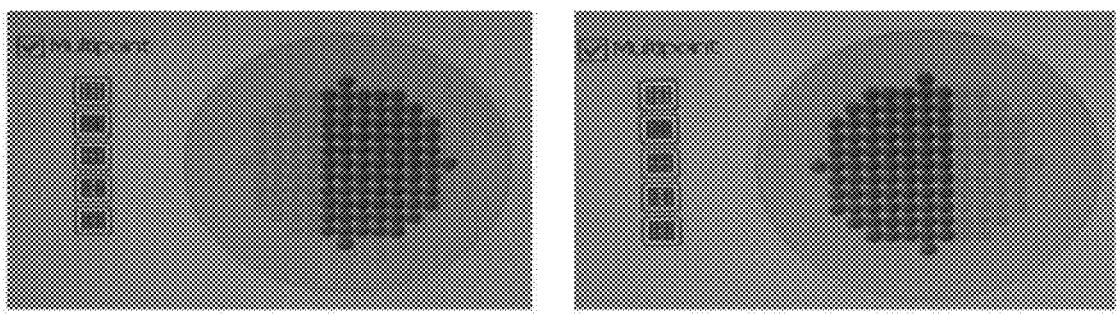
FIG. 14 shows multipoint absorbance measurement of the (24-well plate) wells divided into two compartments by GrowDex barrier. HepaRG cells are on the left and BJ fibroblasts on the right side of the barrier.

After the 3-hours incubation, 20 µl WST-1 reagent was added to both sides of the barrier. The plate was incubated for 1 hr. Absorbance was read using the Multipoint measurement program, which measured absorbance from 39 points from both sides of the barrier, see FIG. 14.

Data Handling

The mean absorbances were calculated separately for each well and both sides of the barrier. The decision on the acceptability of the data was made individually for each well. The data of the well was accepted provided that the barrier functioned properly, i.e. the ratio of HepaRG and BJ absorbances at 450 nm was >2.0.

Figure 15:
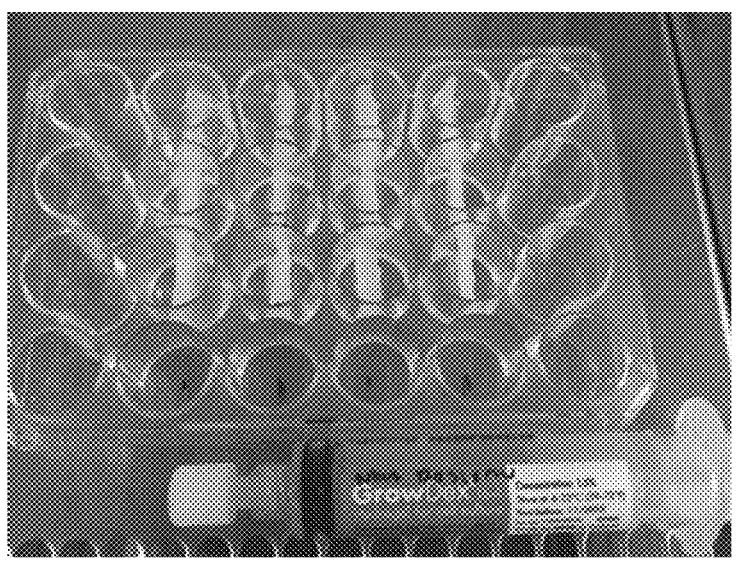
FIG. 15 shows freshly prepared GrowDex barriers in a 24-well plate.

Based on above, 6 of 12 wells were accepted, and the absorbance data of these six wells were used in the calculation of results. FIG. 15 shows the barriers immediately after their construction. Table 2 shows the 24-well plate configuration after seeding of cells and exposure to selegiline. The wells that were rejected from calculations are marked with an asterisk (*).

TABLE 2

| HepaRG VC | BJ | * | * | * | * | HepaRG 1 µg/ml seleg. | BJ |
|---|---|---|---|---|---|---|---|
| | | HepaRG 10 µg/ml seleg. | BJ | HepaRG 5 µg/ml seleg. | BJ | | |
| HepaRG VC | BJ | HepaRG 10 µg/ml seleg | BJ | * | * | * | * |
| | | | | HepaRG 5 µg/ml seleg | BJ | HepaRG 1 µg/ml seleg. | BJ |
| HepaRG VC | BJ | * | * | HepaRG 5 µg/ml seleg. | BJ | * | * |
| | | HepaRG 10 µg/ml seleg. | BJ | | | HepaRG 1 µg/ml seleg. | BJ |

Results

Table 3 summarizes the effect of selegiline on HepaRG and BJ cell viability when exposed to BJ cells via HepaRG cells for 3 hrs. The lowest concentrations of selegiline, i.e. 1 and 5 µg/ml, seemed to increase both HepaRG and BJ viability. The highest concentration, 10 µg/ml, decreased HepaRG and BJ viability, ~5% and ~25%, respectively.

Table 3. The effect of selegiline on BJ and HepaRG cell viability after 3 hrs exposure. The data represents absorbances at 450 nm. HepaRG and BJ cells were separated by GrowDex barrier. Selegiline dosing occurred always via HepaRG cells. The results are from 1-3 wells/treatment. Absorbance reading was performed using multipoint measurement, where 39 points were measured from both sides of the barrier.

TABLE 3

|  | No selegiline (control) | | 1 µg/ml selegiline | | 5 µg/ml selegiline | | 10 µg/ml selegiline | |
| --- | --- | --- | --- | --- | --- | --- | --- | --- |
|  | HepaRG | BJ cells | HepaRG | BJ cells | HepaRG | BJ cells | HepaRG | BJ cells |
| MEAN | 3.052 | 1.010 | 3.486 | 1.429 | 3.344 | 1.219 | 2.892 | 0.760 |
| MEDIAN | 3.165 | 0.963 | 3.794 | 1.539 | 3.588 | 1.243 | 3.078 | 0.676 |
| STDEV | 0.570 | 0.517 | 0.636 | 0.560 | 0.672 | 0.596 | 0.518 | 0.395 |
| STERR | 0.053 | 0.048 | 0.102 | 0.090 | 0.108 | 0.096 | 0.083 | 0.063 |
| MIN | 1.616 | 0.389 | 2.309 | 0.455 | 1.812 | 0.421 | 1.478 | 0.381 |
| MAX | 4.070 | 2.097 | 4.297 | 2.170 | 4.138 | 2.193 | 3.561 | 1.511 |
| % of control | 100.00 | 100.00 | 114.23 | 141.43 | 109.57 | 120.69 | 94.77 | 75.19 |
| N | 117 | 117 | 39 | 39 | 39 | 39 | 39 | 39 |

Conclusions

As WST-1 measures mitochondrial activity as an index of cell viability, it seems that the lowest selegiline concentrations caused hormesis, i.e., metabolic activation of both HepaRG and BJ cells. (The same was seen in Experiment 1 with BJ cells). The highest concentration, 10 µg/ml, however, reduced BJ viability 25%. This was probably due to toxic metabolites produced from selegiline by HepaRG cells. This gets support from Experiment 1 as selegiline without HepaRG treatment did not reduce BJ cell viability.

Experiment 3 (Toxicity of Paracetamol to BJ Cells when Exposed Via HepaRG Cells)

Aim

The aim of Experiment 3 was principally the same as in Experiment 2, i.e., to investigate whether the proposed test model, i.e, co-culturing HepaRG cells (metabolizing component) and BJ fibroblasts (target cells) in wells of a 24-well plate separated by GrowDex barrier, can be used to recognize the metabolism-dependent toxicity to target cells. The difference from Experiment 2 were that paracetamol was used as a test compound
lower GrowDex barriers were constructed to improve their stability, and the volume in each side of the barrier was reduced from 200 µl to 150 µl
the amount of BJ cells in the wells was bigger than in Experiment 2
the exposure times were 4 and 20 hrs Procedure Preparation of GrowDex Barriers GrowDex barriers were prepared to split the wells of a 24-well plate into two "equally sized" compartments as follows. 250 µl GrowDex was pipetted to the wells (using positive displacement pipette) to construct the first layer of the barrier. The barriers were left to dry in the laminar hood for 1 hr with the lid open. Then a second layer was pipetted on the top of the first layer. The composition of GrowDex (lot 11992) had become looser, and it was carefully mixed several time on a petri dish avoiding formation of air bubbles.

Altogether 20 barriers were prepared. After constructing the barriers, they were allowed to dry overnight at room temperature with the lid closed. (This was different from Experiment 2 where the plates were stored in the fridge overnight).

Seeding of BJ Cells

Next day 6 of 20 barriers had collapsed and were rejected. The 14 usable barriers were moisturized by adding 200 µl BJ cell culture to both sides of the barrier. The plates were incubated for 1 hr in the cell culture incubator.

BJ cell suspension was prepared at a density of 70 000 cells/ml BJ cell culture medium, and 150 µl of this suspension was pipetted to the right side of the barriers resulting in 10 500 cells/well.

Next day before seeding HepaRG cells, the medium of BJ cells was changed by removing carefully the old medium, and replacing it with 150 µl BJ cell culture medium supplemented with 5% FBS.

Seeding of HepaRG Cells

HepaRG suspension was prepared at a density of 2 million HepaRG cells/ml HepaRG® Thawing/Plating/General Purpose Medium 670. Medium was removed from the left side of the barrier. 150 µl HepaRG suspension, i.e., 300 000 cells was added to each well. The plate was gently agitated in back-and-forth and side-to-side manner, and the homogeneity of the cell distribution was ensured visually. The plate was placed back into cell culture incubator and the cells were let recover for 4 hrs before exposure.

Preparation of Paracetamol Dilutions

Paracetamol dilutions were prepared on the day of use. First, 1 mg/ml paracetamol stock was prepared in HepaRG TOX medium. Then 500 µg/ml dilution was prepared using the stock and HepaRG TOX medium. HepaRG TOX Medium alone served as vehicle control.

Exposure

Medium was carefully removed from the HepaRG cells (left side of the barrier), and replaced with 75 µl/well HepaRG TOX Medium/well. This was performed one well at a time. After changing the medium to all wells, 75 µl paracetamol dilutions and vehicle control was added on top of HepaRG cells. Final paracetamol concentrations were hence 0.5× the concentrations of the dilution used, i.e. 500 µg/ml and 100 µg/ml. The cells were incubated for 4 and 20 hrs before WST-1 assay.

Cytotoxicity/Viability Assay (WST-1)

After the incubation, 15 µl WST-1 reagent was added to both sides of the barrier. The plate was incubated for 1 hr in 4 hrs exposure, and for 2 hrs in 20 hrs exposure. Absorbance was read using the Multipoint measurement.

Data Handling

The results were calculated as described in Experiment 2. Four wells (barriers) of six passed the acceptance criterion in the 4 hrs exposure (FIG. 16), and four wells (barriers) of eight passed the acceptance criterion in the 20 hrs exposure (FIG. 17).

Figure 16:
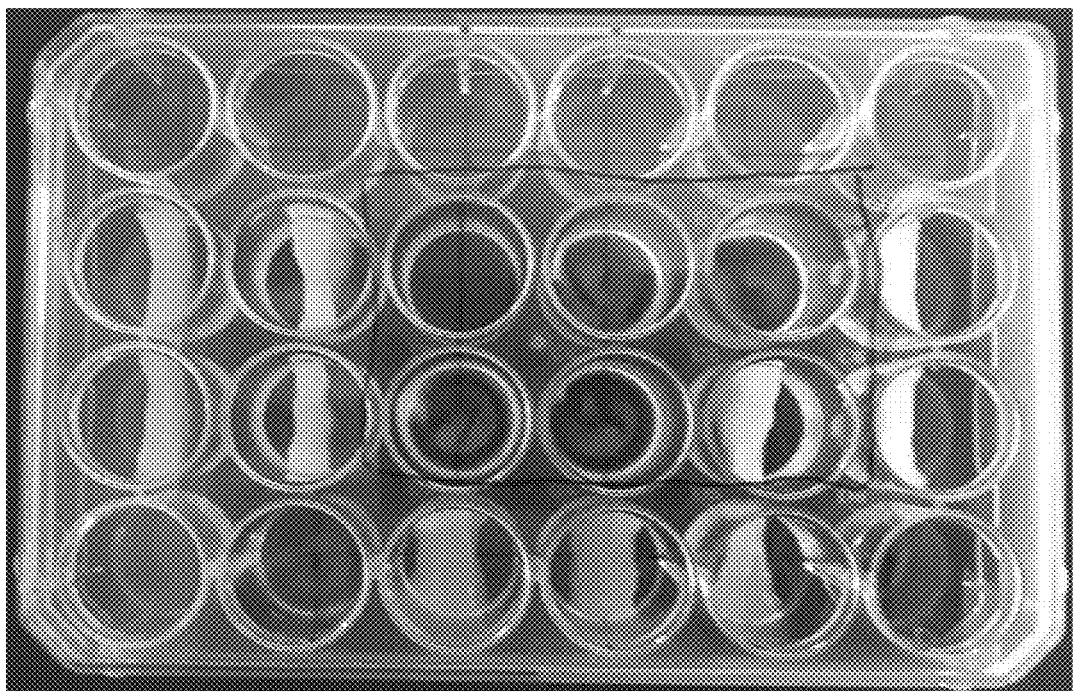
FIG. 16 shows freshly prepared GrowDex barriers in a 24-well plate.
Figure 17:
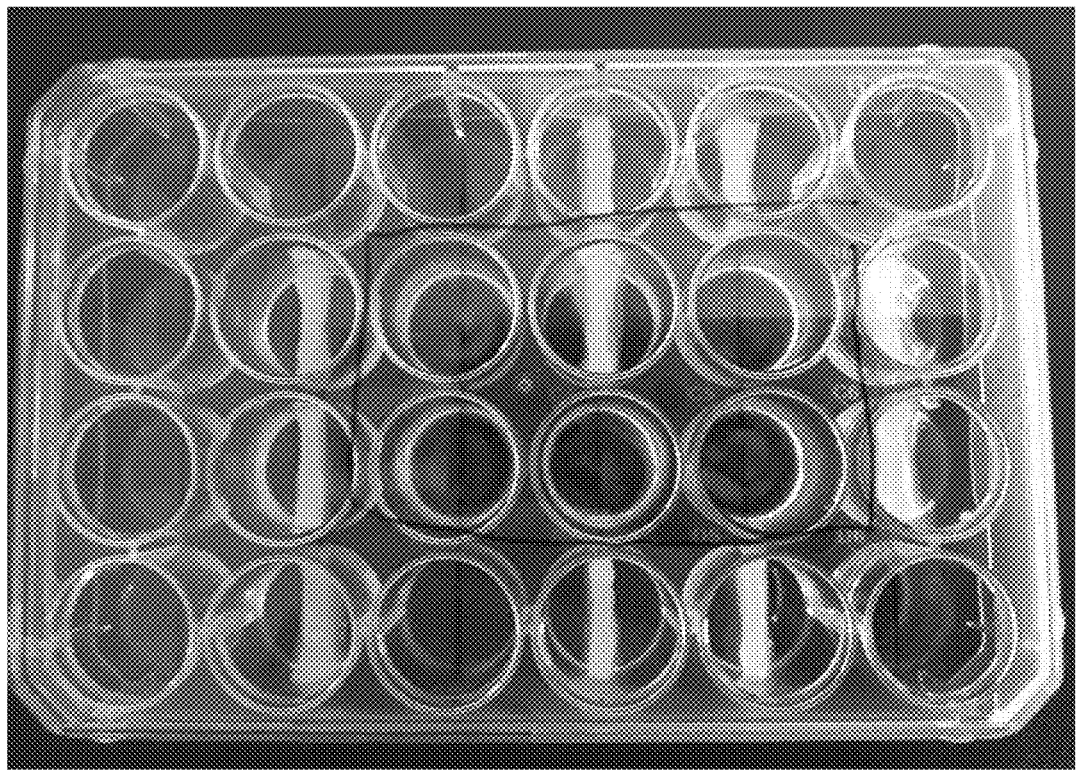
FIG. 17 shows freshly prepared GrowDex barriers in a 24-well plate.

Table 4 shows the 24-well plate configuration according to FIG. 16 after seeding of cells and exposure to paracetamol for 4 hrs. The wells that were rejected from calculations are marked with an asterisk (*).

TABLE 4

| | | | | | | | |
|---|---|---|---|---|---|---|---|
| HepaRG VC | BJ | * HepaRG 500 µg/ml parac. | * BJ | | | * HepaRG 250 µg/ml parac. | * BJ |
| HepaRG VC | BJ | HepaRG 500 µg/ml parac. | BJ | HepaRG 250 µg/ml parac. | BJ | HepaRG 250 µg/ml parac. | BJ |

Table 5 shows the 24-well plate configuration according to FIG. 17 after seeding of cells and exposure to paracetamol for 20 hrs. The wells that were rejected from calculations are marked with an asterisk (*).

TABLE 5

| | | | | | | | |
|---|---|---|---|---|---|---|---|
| | | * HepaRG 500 µg/ml parac. | * BJ | HepaRG 250 µg/ml parac. | BJ | | |
| HepaRG VC | BJ | * HepaRG 500 µg/ml parac. | * BJ | | | | |
| HepaRG VC | BJ | * HepaRG 500 µg/ml parac. | * BJ | HepaRG 500 µg/ml parac. | BJ | * HepaRG 250 µg/ml parac. | * BJ |

Results

Tables 6 and 7 summarize the effects of paracetamol on HepaRG and BJ cell viability when exposed to BJ cells via HepaRG cells for 4 hrs (Table 6), and for 20 hrs (Table 7). The short exposure did not affect cell viability at 500 µg/ml, but 250 µg/ml paracetamol seemed to decrease HepaRG viability ~15% and increase BJ cell viability ~40%. In the longer exposure paracetamol increased BJ viability at 250 µg/ml ~30%, and reduced HepaRG ~10% at the highest concentration.

Tables 6-7. The effect of paracetamol on BJ and HepaRG cell viability after 4 hrs exposure (Table 6), and 20 hrs exposure (Table IV). The data represents absorbances at 450 nm. HepaRG and BJ cells were separated by GrowDex barrier. Paracetamol dosing occurred always via HepaRG cells. The results are from 1-2 wells/treatment. Absorbance reading was performed using multipoint measurement, where 39 points were measured from both sides of the barrier.

TABLE 6

| | No paracetamol (control) | | 250 µg/ml paracetamol | | 500 µg/ml paracetamol | |
|---|---|---|---|---|---|---|
| | HepaRG | BJ cells | HepaRG | BJ cells | HepaRG | BJ cells |
| MEAN | 4.172 | 1.196 | 3.571 | 1.685 | 4.074 | 1.188 |
| MEDIAN | 4.327 | 1.074 | 3.513 | 1.777 | 4.134 | 1.164 |
| STDEV | 0.619 | 0.529 | 0.562 | 0.743 | 0.422 | 0.525 |
| STERR | 0.070 | 0.060 | 0.064 | 0.084 | 0.068 | 0.084 |
| MIN | 2.866 | 0.563 | 2.554 | 0.539 | 3.122 | 0.607 |
| MAX | 6.000 | 2.244 | 4.768 | 3.105 | 4.680 | 2.302 |
| % of control | 100.00 | 100.00 | 85.58 | 140.89 | 97.65 | 99.34 |
| N | 78 | 78 | 78 | 78 | 39 | 39 |

TABLE 7

| | No paracetamol (control) | | 250 µg/ml paracetamol | | 500 µg/ml paracetamol | |
|---|---|---|---|---|---|---|
| | HepaRG | BJ cells | HepaRG | BJ cells | HepaRG | BJ cells |
| MEAN | 3.966 | 1.386 | 4.196 | 1.777 | 3.606 | 1.356 |
| MEDIAN | 3.928 | 1.293 | 4.239 | 1.801 | 3.771 | 1.325 |
| STDEV | 0.496 | 0.599 | 0.494 | 0.706 | 0.563 | 0.619 |
| STERR | 0.056 | 0.068 | 0.079 | 0.113 | 0.090 | 0.099 |
| MIN | 3.009 | 0.687 | 3.355 | 0.865 | 2.801 | 0.632 |
| MAX | 4.941 | 2.496 | 5.149 | 2.959 | 4.483 | 2.268 |
| % of control | 100.00 | 100.00 | 105.78 | 128.23 | 90.91 | 97.89 |
| N | 78 | 78 | 39 | 39 | 39 | 39 |

Experiment 4 (Metabolic Activity of HepaRG Cells)

Aim

Even if HepaRG cells are considered a good model for studying CYP induction and drug metabolism (EURL ECVAM 2012), after Experiment 3 the metabolic activity of HepaRG cells was doubted because of a failure to demonstrate the expected metabolism-dependent toxicity of paracetamol. Therefore an experiment was made using a method previously developed for investigating metabolism dependent toxicity, both hepatocyte-conditioned exposure medium and non-conditioned medium were used to treat the BJ cells.

Procedure

Seeding of BJ Fibroblasts

BJ cell suspension was prepared at a density of 40 000 cells/ml in BJ cell culture medium. 100 µl of this suspension was pipetted to a 96-well plate resulting in 4000 cells/well.

Seeding of HepaRG Cells

The HepaRG cells that were left from Experiment 3 were seeded to a 25 $cm^2$ cell culture flask, and cultured for 1 week. Medium (HepaRG induction medium) was renewed twice during the week.

Conditioning of Paracetamol with HepaRG Cells

The medium was removed from HepaRG cells (grown in a 25 $cm^2$ flask), and replaced by 2.5 ml of HepaRG TOX medium. Then 2.5 ml of 1 mg/ml paracetamol prepared in HepaRG TOX medium was added to the flask (final paracetamol concentration 500 µg/ml). HepaRG cells were incubated with paracetamol for 20 hrs.

Exposure of BJ Cells to Paracetamol as Such and to HepaRG-Treated Paracetamol

The medium was removed from BJ cells, and replaced by 500 µg/ml paracetamol in BJ chemical dilution medium or 500 µg/ml HepaRG-conditioned-paracetamol in HepaRG TOX-medium. BJ chemical dilution medium and HepaRG TOX medium served as vehicle controls. All treatments were tested in 16 parallel wells. The exposure time was 24 hrs.

Cytotoxicity/Viability Assay

After the exposure, 10 µl WST-1 reagent was added to the wells. The plate was incubated for 2 hrs, and the absorbance was read at 450 nm.

Data Handling

Blank values (contained all reagents, including drugs, but no cells) were subtracted from the absorbance data. The results were given as percentage of viable cells as compared to untreated (vehicle) control. The statistical difference between untreated control and treated cells was assessed using t-test (SigmaPiot).

Results

Figure 18:
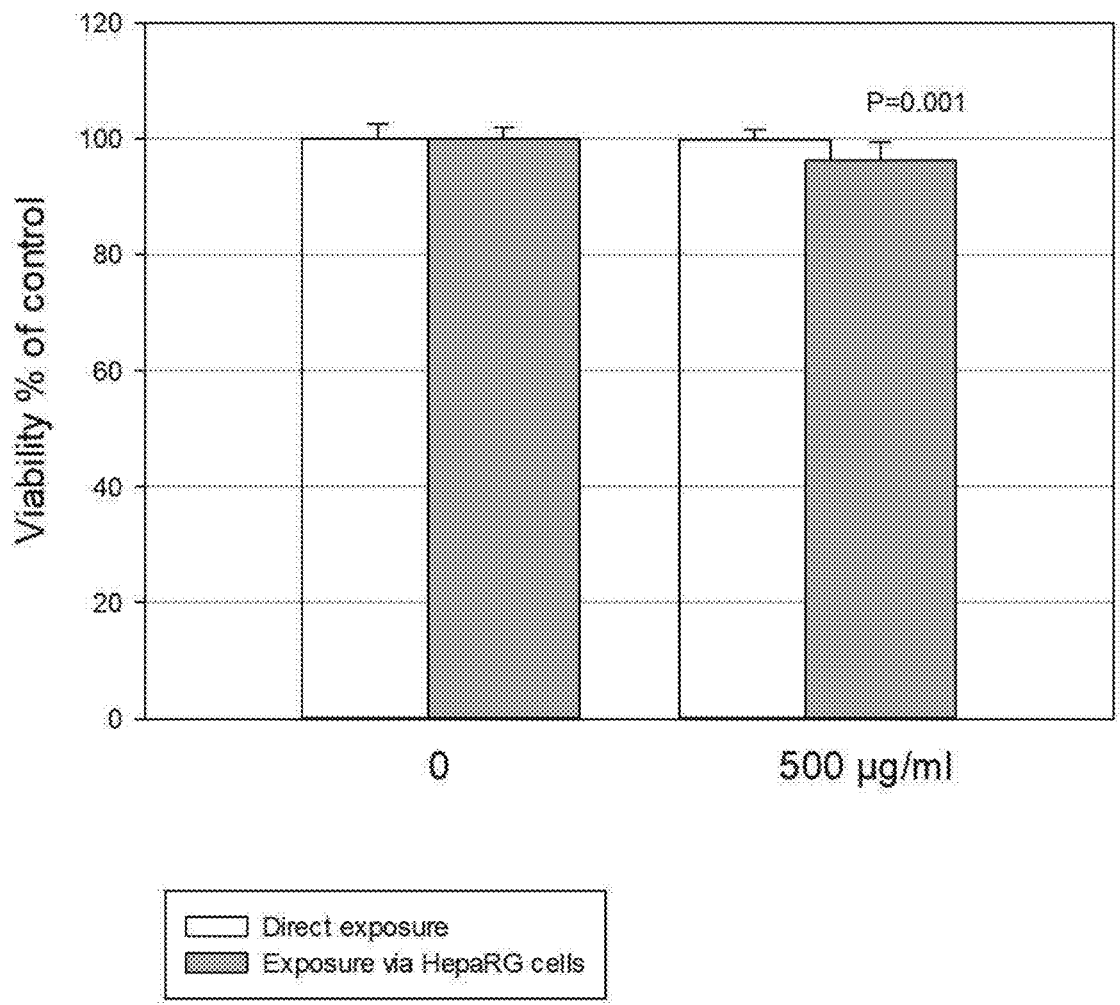
FIG. 18 shows the effect of direct paracetamol, or HepaRG-conditioned paracetamol exposure on the viability of human BJ fibroblasts. Each bar represents MEAN±SEM, N=12 (control), N=18 (500 µg/ml paracetamol). Statistical differences were investigated using t-test (SigmaPlot).

HepaRG-treatment had a minor effect on BJ fibroblast viability. FIG. 18 shows the effect of direct paracetamol or HepaRG-conditioned paracetamol exposure on the viability of human BJ fibroblasts.

Conclusions

HepaRG cells did not convert paracetamol to metabolites that would have been toxic to BJ cells. Hence, it was concluded that paracetamol was not metabolized by HepaRG cells.

Discussion

Barrier Constructs

There were several attempts to construct GrowDex barriers. Based on all successful and less successful efforts, the following was concluded.

The following observations were made which may help constructing durable barriers:

Use 1.5% GrowDex. Do not use the bright GrowDex.

Do not pipette GrowDex directly from the tube or syringe. Instead transfer the gel to a petri dish and mix carefully avoiding the formation of air bubbles. It is very important that the composition is very homogenous when pipetting the barriers.

Prepare the barrier from two layers (2×250 µl in a 24-well plate), let the first layer dry for 0.5-1.0 hr with the lid open in the laminar hood (RT) before adding the second layer. (If the whole barrier is constructed at one time, it collapses within the next 24 hrs).

Let the second layer dry 0.5-1.0 hr with the lid open in the laminar hood (RT).

Low and wide barriers are more durable than high and narrow barriers. It is possible to prepare both, but narrow barriers tend to collapse within the next 24 hrs.

Do not try to fix the barrier mechanically, e.g. using spatel. It is tempting, but reduces the adhesion of the barrier to the well and increases the risk of cell leakage.

Store the barriers overnight at room temperature with the lid closed

Moisturize 1 hr before use with the same medium that will be used in cell seeding.

As about 50% of the barrier leaked (based on the criterion on HepaRG:BJ absorbance ratio), there should be a better way to glue the GrowDex barrier to the surface of the well. Collagen-coating was not tried yet, nor other treatments of the surface of the well.

Metabolic Activity of HepaRG Cells

According to the manufacturer (Thermo Fisher Scientific), cryopreserved HepaRG™ cells retain a high level of CYP activities during the first 24 hours following thaw and plating, and these activities then decrease while the cells reconstitute the monolayer, then the activities return during the fourth day in culture, peaking at Day 7-10. Hence, as the experiments were performed during the first 24 hours, proper metabolic activity of HepaRG cells was expected. Even if selegiline toxicity to BJ cells increased after HepaRG treatment, paracetamol was not metabolized to more toxic compounds. They showed that the metabolic activity of cryopreserved HepaRG cells indeed peaks after 10 days in culture, but within the first 24 hrs, the activity of most CYP enzymes are low, with the exception of CYP3A4. The role of CYP3A4 in paracetamol metabolism is controversial, with findings ranging from no significant contribution to the primary role of CYP3A4 in paracetamol metabolism. Instead CYP2B6 plays the major role in selegiline metabolism, while CYP3A4 is less important.

It would be challenging to maintain the HepaRG culture behind the barrier for 10 days. Therefore, currently the best choice to be used in this model would be human cryopreserved hepatocytes or primary hepatocytes, which can and should be used immediately. If separately agreed FICAM is willing to perform those tests.

Exposure Time 3-4 hrs exposure times were used for selegiline and paracetamol, and also 20 hrs exposure for paracetamol. Drug metabolism occurs within hours, and three hours was indeed long enough to convert selegiline to toxic metabolites. Longer incubation time is not needed, and should not be used to measure metabolism dependent toxicity to the target cells.

Conclusions

A preliminary test method protocol, i.e. co-culturing HepaRG cells (metabolizing component) and BJ fibroblasts (target cells) in wells of a 24-well plate separated by GrowDex barrier, and dosing test compound via HepaRG, was developed.

Using the test method it was possible to demonstrate metabolism-dependent toxicity of selegiline. However it was not possible to demonstrate metabolism-dependent toxicity of paracetamol.

HepaRG is not the best metabolizing component to be used in this test model as its enzyme activity seems not to be high enough shortly after thawing. On the other hand, only one lot was used in this study, and there may be lot-to-lot variation.

The success rate of barriers was ~50%.

Example 3: Construction of Nanofibrillar Cellulose Barriers with 3D Printer

The aim of this study was to investigate whether 3D printer can be used to construct nanofibrillar cellulose barriers. A secondary goal was to investigate barrier properties: do barriers keep cells separated in different compartments, but still allow nutrients and chemicals to pass from one cell compartment to the other. GrowDex™ was used as nanofibrillar cellulose.

In the previous experiments, it was shown that 1.5% GrowDex can be used to construct barriers manually. However, the success rate of these barriers, (in terms of barrier leakage/tightness) was about 50%. Utilization of 3D printer would bring the benefit of automation and production of more uniform barriers compared to manual application.

Materials
Test System
  Human fibroblast BJ (Cat No. HB-8065) purchased from ATCC (FICAM's lot 1-BJ/13) were used in this study.
GrowDex Hydrogel for Cell Culture
  GrowDexT, 1.0% (anionic)
  GrowDex, 1.5% (chemically unmodified)
  GrowDexT, 2.0% (anionic)
  GrowDex was obtained from UPM packed in syringes. For details, lots etc. see Appendix 1.
Reagents, Solutions and Materials
  Gelatin (Sigma #G1890, lot SLBX2973), FICAM's lot 2%Gelatin/MPE/1/110319
  0.1 mg/ml Poly-D-Lysine (Sigma, #P6407, lot 090M8707V)
  Fibronectin (Promocell #C-43050, lot 439P121)
  dH2O (Gibco #15230, lots 1641929, 1814133, 1895791)
  PBS (Lonza #17-516F, lot 708833)
  $CaCl_2$ (Sigma, #793639, lot MKCG4711
  MEM (Gibco #21090, lot 1944344)
  BJ cell culture medium, FICAM's lots BJ/CT0097/MPE/1/201118, BJ/CT0097/MPE/2/301118, BJ/CT0097/MPE/3/040119, BJ/CT0097/MPE/4/130119, BJ/CT0097/3/MPE/1/130319
  0.2% Trypan Blue, FICAM's lot 0.2% TB/HM/20/100419
  Amitriptyline hydrochloride (CAS 151-21-3) (Sigma #A8404, lot BCBN3158V)
  SDS (CAS 549-18-8) (Sigma #L6026, lot SLBV9880)
  WST-1 (Takara #MK400, lot AHXP001)
  24-well plates
  12-well plates
  16G metal needles, BD PrecisionGlide, REF 301692
  Plastic Luer tips (Adhesive Dispensing Ltd: 25G #AD25TT lot 4502063-30; 22G #AD22TT lot 4502004-46; 18G #AD18TT lot 4502335-9)
Equipment
  Fab@home v1 3D printer
  Inverted light microscope (Zeiss Primovert+Axiocam ERc 5s)+digital camera
  Plate reader

Experimental Procedure

This study was divided into two parts:
1) In the first part a protocol was created and optimized for 3D-printing of GrowDex barriers. The effect of coating beneath the barriers, and the stability of barriers were tested.
2) In the second part a preliminary investigation of barrier properties was performed using BJ cells and Sodium Dodecyl Sulfate (SDS) and Amitriptyline hydrochloride as reference chemicals to find out whether barriers keep cells separated in different compartments, but still allow nutrients and chemicals to pass from one compartment to the other. Amitriptyline is a tricyclic compound, specifically a dibenzocycloheptadiene 3-(10,11-dihydro-5H-dibenzo[a,d]cycloheptene-5-ylidene)-N,N-dimethylpropan-1-amine, and possesses three rings fused together with a side chain attached in its chemical structure Construction of Circular Barriers to 12 and 24 Well Plates Using a 3D Printer
Creating Protocol for 3D-Printing
Aim The aim of the first part of this study was to optimize the 3D printer for printing of GrowDex on the wells of multi-well plates. Following issues were considered:
  1. Applying GrowDex syringes for the 3D-Printer
  2. Finding optimal printer parameters for each GrowDex concentration
  3. Optimal GrowDex concentration
  4. Applicability to 12 and 24-well formats Applying GrowDex Syringes for the 3D-Printer Feasibility of 5-10 ml GrowDex syringes directly for 3D printing was investigated. The syringe in which GrowDex is supplied, Braun Omnifix, had to be modified to fit in the holder of the 3D printer. To do so, the plunger at its extended position was pulled up a couple of millimeters, then it was cut with a knife align the top part of the syringe. Then the plunger was pushed down until gel started to flow through the tip. After this, the printer was set to push the plunger with its own mechanism.

Secondly, different syringe tips and needles were tested. One essential issue became apparent; there was severe leaking between the syringe head and tips without a firm locking mechanism. The solution was acquiring tips with Luer locking mechanism. Different needle gauge sizes (metal 16G, plastic 25, 22, 18 G) were also tested. Metallic 16G seemed to be the best choice for applying both 1.5% GrowDex and 2.0% GrowDexT. Plastic gauges did not work as well as metallic gauges, since the gel came out from the tip unevenly.

Figure 19:
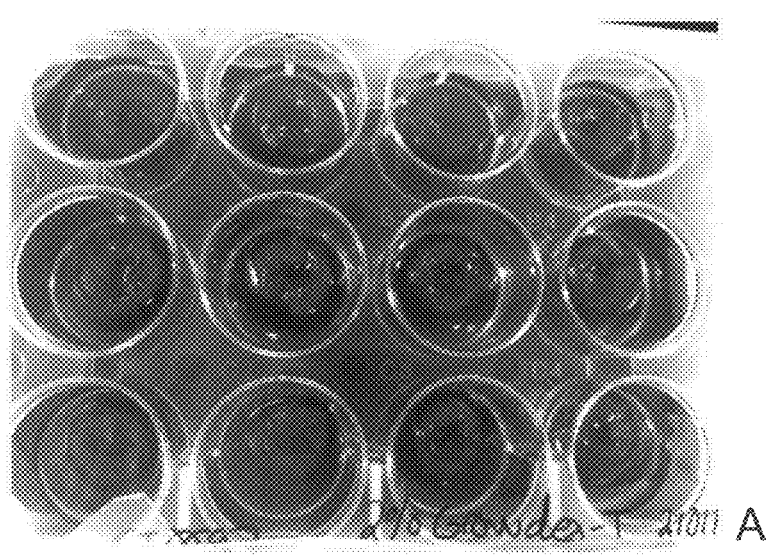
FIG. 19 shows uneven barrier constructs printed using 1.5% GrowDex (A, B) and 2.0% GrowDexT (C).
Figure 19:
Figure 19:
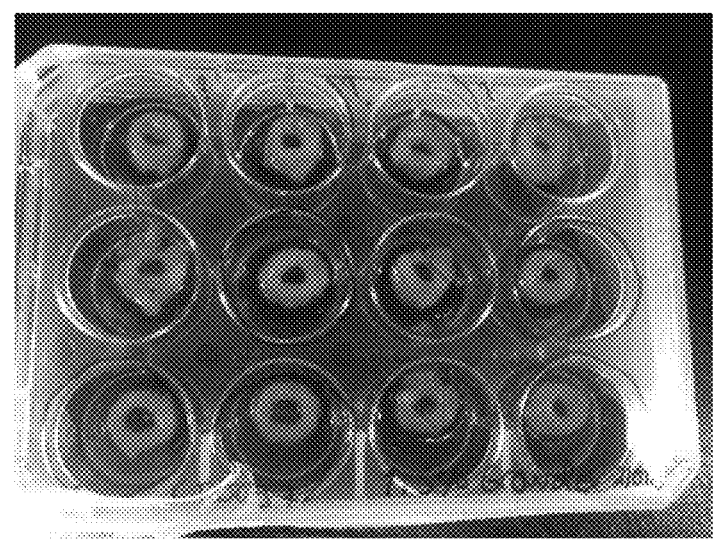

Clogging and air bubbles in the hydrogel or rigidity of the syringe plunger caused uneven printing and barriers of poor quality (FIG. 19). To overcome these problems the hydrogel was transferred into new syringes, if the syringe had been opened already before. This helped, but then it appeared that sometimes the plunges of even un-opened syringes were rigid. Hence, the hydrogel should be transferred into a new syringe whether or not the syringe has been opened before. FIGS. 19A-C show uneven barrier constructs printed using 1.5% GrowDex (A, B) and 2.0% GrowDexT (C).

Finding Optimal Printer Parameters for Each Concentration

Figure 20:
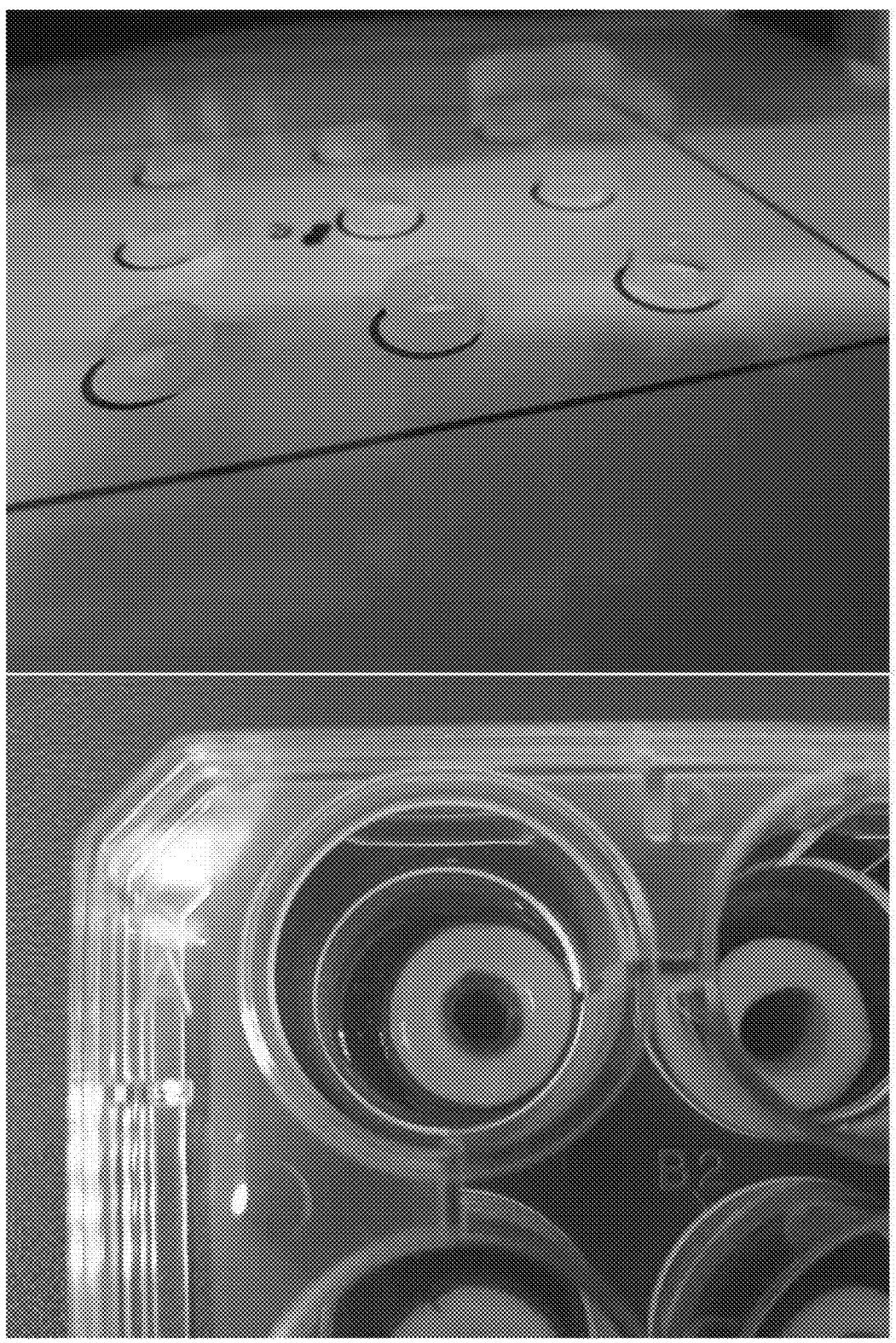
FIG. 20 shows the first 3D-printings were made on films (upper figure) before moving to multi-well plates (lower figure).

The printing protocol was optimized before starting printing on multi well plate (FIG. 20). For different well plates and hydrogel concentrations, optimal parameters were slightly different, see Table 8

TABLE 8

Optimal printer parameters

| | 1.5% GrowDex in 12-well plate | 2.0% GrowDexT in 12-well plate | 1.0% GrowDexT in 12-well plate | 1.5% GrowDex in 24-well plate | 2.0% GrowDexT in 24-well plate |
|---|---|---|---|---|---|
| Pathwidth mm | 1.0 | 1.0 | 1.0 | 1.0 | 1 |
| Path height mm | 1.0 | 1.0 | 1.0 | 1.1 | 1.1 |
| Pushout s | 0.050 | 0.050 | 0.200 | 0.050 | 0.05 |
| Suckback s | 0.080 | 0.080 | 0.080 | 0.080 | 0.08 |
| Deposition rate mm | 0.019 | 0.015 | 0.017 | 0.019 | 0.015 |
| Increment mm | 0.500 | 0.500 | 0.500 | 0.500 | 0.500 |
| Pathspeed mm/s | 2 | 2 | 2 | 2 | 2 |

For printing of barriers, a stereolithography (stl) image of the wells was prepared using a CAD program. For 12-well plates, circular barriers with 11 mm cross section, 1.5 mm wall thickness and 5 mm height were drawn, and for 24-well plates 9 mm cross section, 0.5 mm wall thickness and 5 mm height were drawn, respectively. In each printing round, two hydrogel rings were printed side by side (without drying inbetween). In the next round two rings were printed on top of the first two rings etc. Altogether 4 rounds and 8 rings were printed to construct one barrier ring. The whole plate was first printed with the first layer, then the printing started again from the first well adding the second layer and so on. The layer increment during the printing was set so that the tip touched the previous layer. It made the barrier more even (it smoothed the possible imperfections, e.g. gaps, in the wall), and it also made the barrier walls somewhat wider/thicker. Wall thickness had an effect on how stable the wall is, very thin walls tend to collapse more easily.

Also other stabilization measures were taken, as well as coating to prevent the barrier from detaching from the substratum, as discussed in previous. FIG. 20 shows the first 3D-printings were made on films (upper figure) before moving to multi-well plates (lower figure).

Optimal Hydrogel Concentration

Circular barriers were printed using both 1.5% and 2.0% GrowDexT. Attempts to print 1.0% GrowDexT were made, but that was not successful. 1.0% GrowDex was too lose for the printing and the resulting barriers were not well shaped. After the first unsuccessful trials (5 Dec. 2018) 1.0% GrowDexT was no longer used in 3D printing. As a conclusion, bot 1.5% GrowDex and 2.0% GrowDexT can be used to construct barriers with a 3D-printer.

Applicability to 12 and 24-Well Formats

Printing onto both 12 and 24 well plates was possible, and both well plate types can be used in cell applications (there is open space for cells inside and outside of barriers). Technical details are summarized in Table 9. An optimized protocol for 3D printing is attached as Appendix 2.

TABLE 9

Summary of the technical details of 3D printing of GrowDex barriers

| | 1.5% GrowDex | | 2.0% GrowDexT | |
|---|---|---|---|---|
| Multi-well plate | 12 | 24 | 12 | 24 |
| Consumption (ml) of hydrogel/plate | 5 | 10 | 5 | 10 |
| Volume (µl) of hydrogel/ring | 417 | 417 | 417 | 417 |
| Layers/barrier | | 4 × 2* | | |
| Drying time (min) inbetween layers | | 15 min | | |
| Duration of printing/plate | 1 h | 1.5 h | 1 h | 1.5 h |
| Height (mm) of Barrier | | 5 | | |
| Drying after construction | | 1 h | | |
| Storage vehicle and temperature | | PBS or MEM, 4° C., sealed with parafilm | | |
| Stability | | at least 2 weeks when stored as described above | | |
| Working volume (inside) µl | 100 | 50 | 100 | 50 |
| Working volume (outside) µl | 400 | 200 | 400 | 200 |
| Needle | | 16 G metallic | | |

*In each round, two hydrogel rings were printed side by side (without drying in-between). In the next round two rings were printed on top of the first two rings etc. Altogether 4 rounds and 8 rings were printed.

Stabilization of Barriers

The aim of this part of the study was to investigate what is the best way to stabilize, i.e., to maintain the shape of the barriers.

Procedure

Different vehicles (storage fluids) were tested to stabilize the 1.5% GrowDex barriers printed to 12-well plate (Picture 3):

1 hr in 1% CaCl$_2$, 2 ml/well, then dry overnight.
Overnight in 1% CaCl$_2$, 2 ml/well
Overnight in MEM, 2 ml/well
Dry overnight, then in 2% CaCl$_2$, 2 ml/well The overnight incubation occurred at 4° C. Table 10 presents 12-well plate lay-out: Stabilization of 1.5% GrowDex barriers in different vehicles.

TABLE 10

| 1% CaCl$_2$ 1 hr | 1% CaCl$_2$ overnight | MEM | First dry, then 2% CaCl$_2$ |
| --- | --- | --- | --- |

Results and Conclusion

Barrier structures remained intact in all tested vehicles, i.e., 1% CaCl$_2$ and MEM, but the barriers were moving, i.e, they were not attached onto the bottoms of wells.

Figure 21:
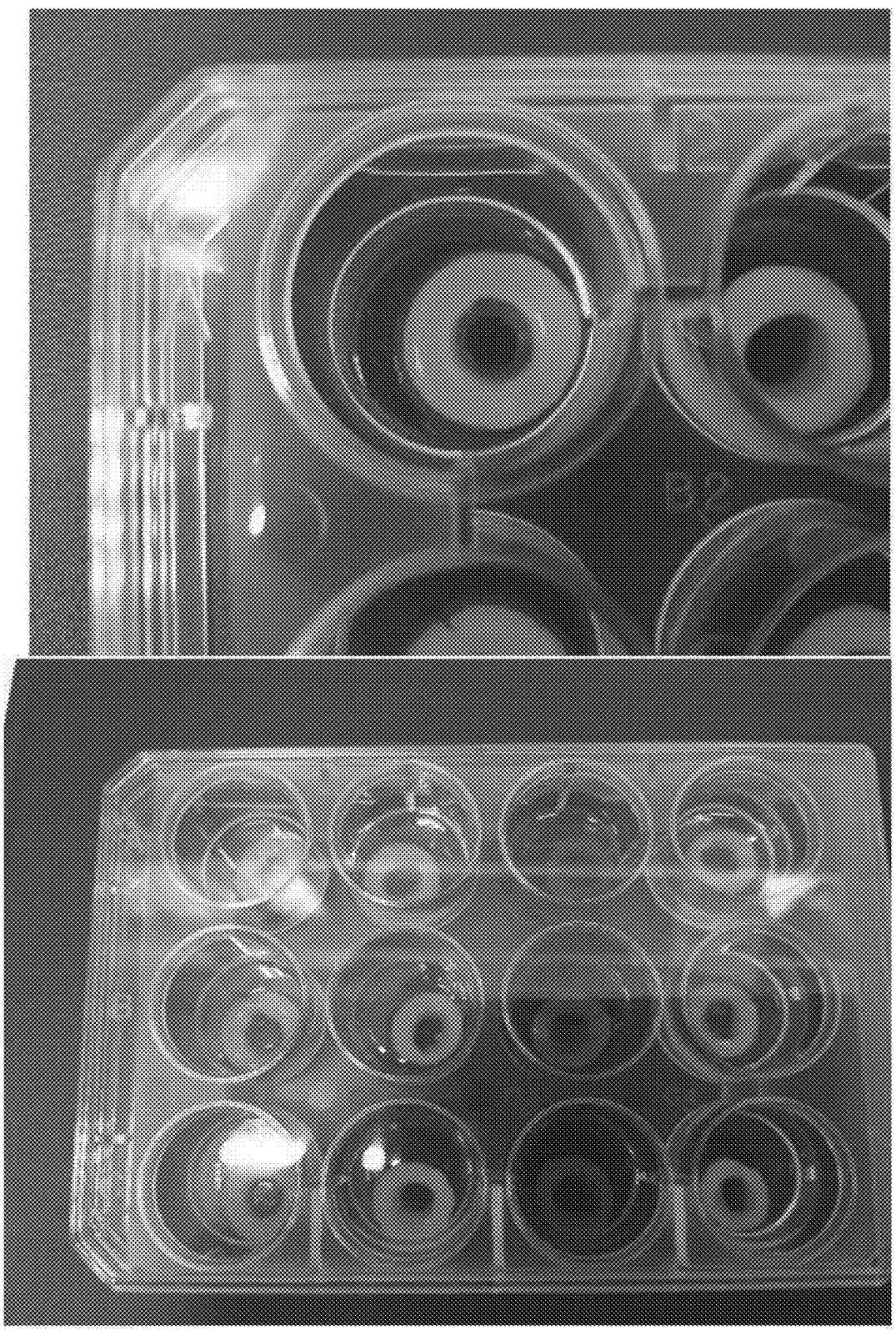
FIG. 21 shows stabilization of barrier constructs in different vehicles; (from left to right): 1% $CaCl_2$ 1 hr, 1% $CaCl_2$ overnight, MEM overnight, and dry treatment overnight and then addition of 2% $CaCl_2$.

FIG. 21 shows stabilization of barrier constructs in different vehicles; (from left to right): 1% CaCl$_2$ 1 hr, 1% CaCl$_2$ overnight, MEM overnight, and dry treatment overnight and then addition of 2% CaCl$_2$.

Coating

The aim of this part of the study was to find conditions where the barriers (1.5% and 2.0%) would stay attached on the bottom of the wells.

Procedure and Results

In order to attach the barriers onto the bottoms of the wells, the wells were coated before the 3D printing. Poly-D-Lysine, gelatin and fibronectin were used as coating materials as follows:

Poly-D-Lysine

300 µl 0.1 mg/ml Poly-D-Lysine (in PBS) was pipetted/well (12-well plate). The plate was incubated for 5 minutes at room temperature. The remaining poly-D-lysine solution was removed from the wells, the wells were rinsed with distilled water, and left to dry for 2 hrs.

Gelatin

300 µl 0.2% gelatin (prepared in distilled water) was pipetted/well (12-well plate). The wells were left to dry for 2 hrs at room temperature. The remaining gelatin solution was removed.

Fibronectin:

1 ml 10 µg/ml Fibronectin was pipetted/well (12-well plate), and left to dry for 2 hrs. The remaining Fibronectin solution was removed.

1.5% GrowDex 1.5% GrowDex barriers were printed onto the bottoms of 12-well plate with different coatings (Poly-D-Lysine, gelatin or fibronectin, and no coating). 1 hr after finishing the printing, 2 ml/well 1% CaCl$_2$ or MEM was added to the wells. The lowest row was left dry.

Figure 22:
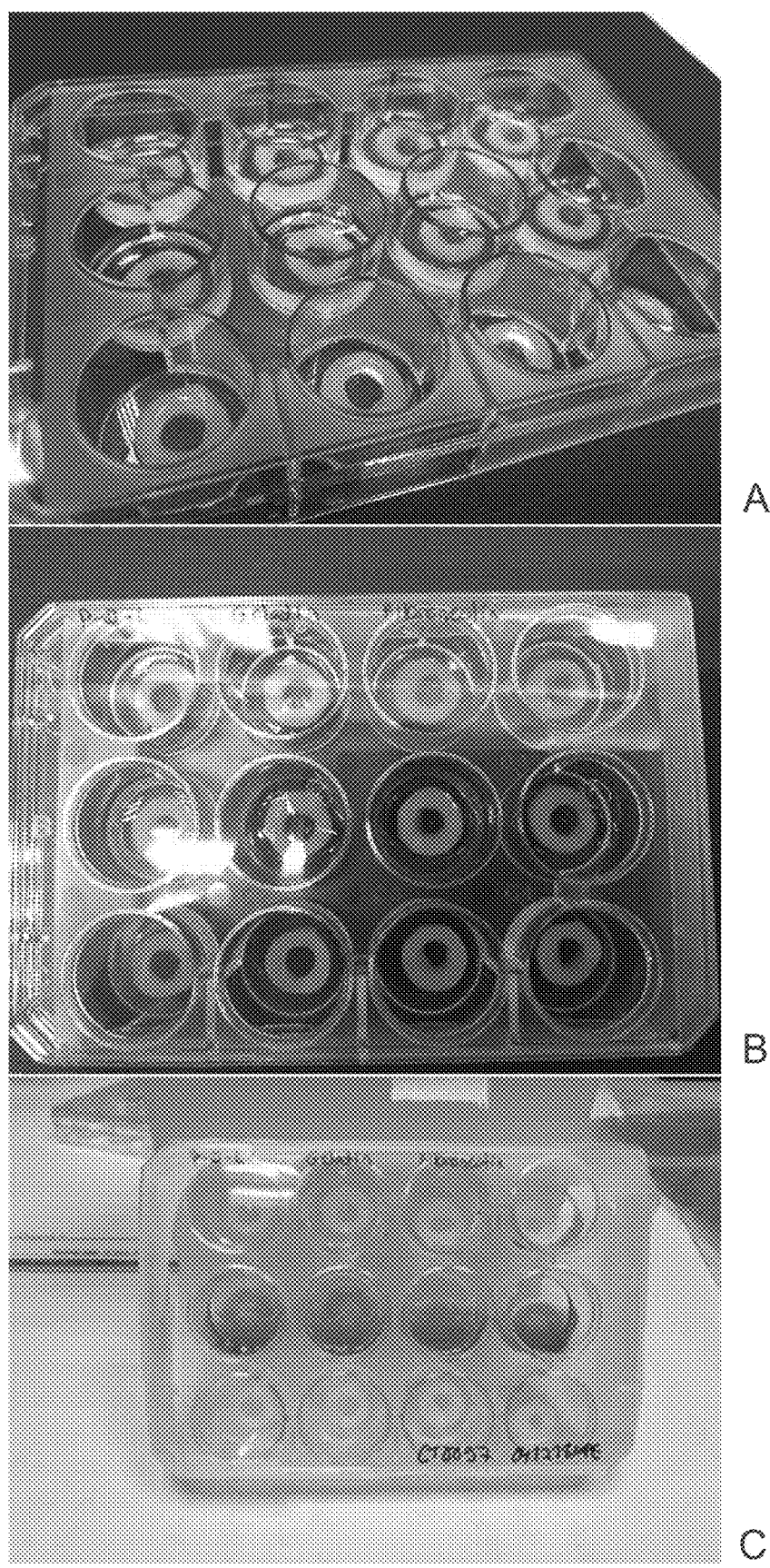
FIG. 22 shows 1.5% GrowDex barriers on wells with different coatings (and no coating), and maintained in different vehicles (A, B). The barriers constructed on Fibronectin-coated and non-coated wells slid down, when the plate was turned 45 degrees. The barriers on poly-D-lysine and gelatin stayed attached to their places (C).

Next day all barriers had maintained their shape, but only barriers on poly-D-lysine and gelatin coatings were attached to the bottom. FIG. 22 shows 1.5% GrowDex barriers on wells with different coatings (and no coating), and maintained in different vehicles (A, B). The barriers constructed on Fibronectin-coated and non-coated wells slid down, when the plate was turned 45 degrees. The barriers on Poly-D-Lysine and Gelatin stayed attached to their places (C).

2.0% GrowDexT

As 0.1 mg/ml poly-D-Lysine and gelatin were the coatings that worked best for 1.5% GrowDex (see previous chapter), these coatings (and no fibronectin) were used for 2.0% GrowDexT.

Figure 23:
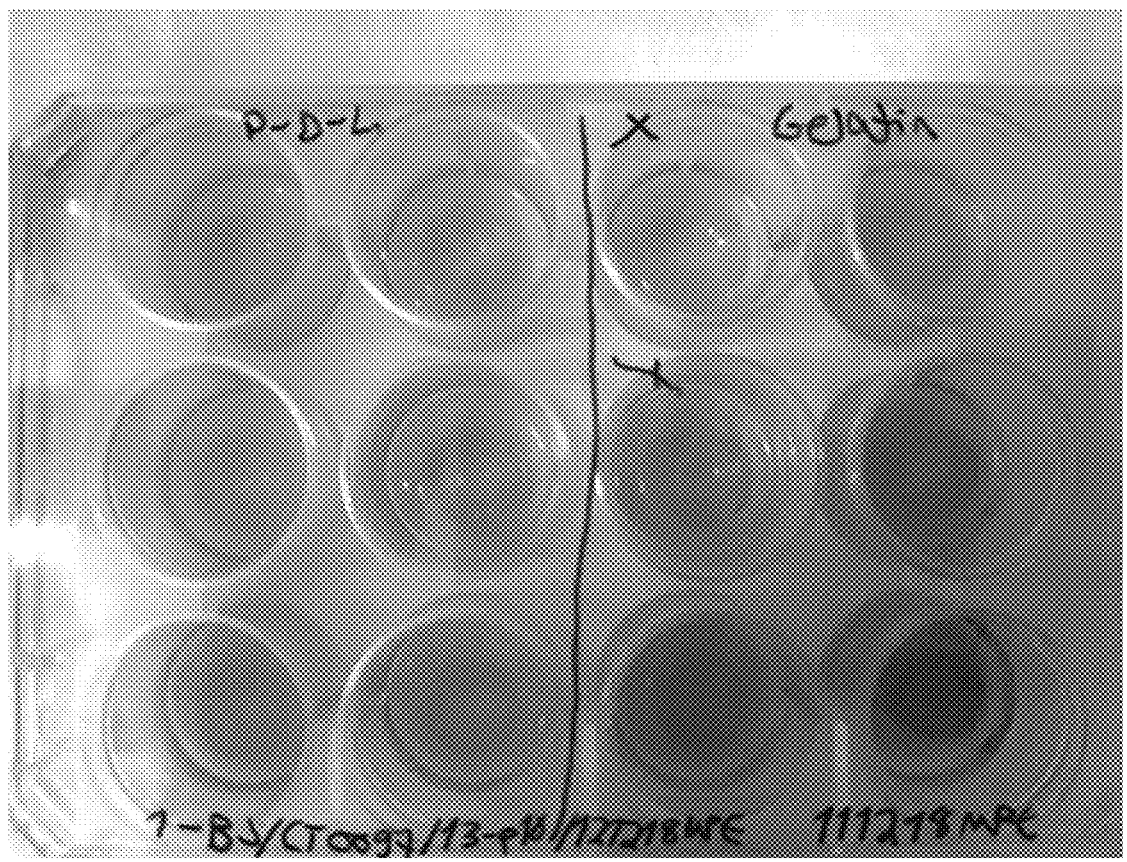
FIG. 23 shows 2.0% GrowDexT barriers constructed on different coatings, and maintained in different vehicles.

Next day all barriers had maintained their shape, and were attached on the bottom of poly-D-lysine and gelatin-coated wells. FIG. 23 shows 2.0% GrowDexT barriers constructed on different coatings, and maintained in different vehicles.

Conclusions

Poly-D-lysine worked as a best coating material to attach the barriers onto the bottoms of the wells. It was therefore selected for future experiments. Gelatin coating also attached the barriers onto the bottom, but according to our previous experiments (not reported here), cells may move along the gelatin coating, which would then diminish the idea of the barrier (to prevent the movement of cells across it).

Barrier properties: Leakage tests using BJ cells and different reference chemicals Test 1

It was investigated whether the 3D-printed GrowDex barriers are suitable for their intended use, i.e. to prevent the movement of cells across the barrier but allow the passage of chemicals. In order to test this, BJ cells were seeded outside of the barrier, and chemicals (SDS and Amitriptyline hydrochloride), which are known to be toxic to BJ cells, were applied inside of the barrier. After 24 hrs incubation it was evaluated microscopically whether cells had stayed outside of the barriers and whether the chemical dosed in the middle of the barrier killed the cells outside of the barrier. For quantification of cell viability, WST-1 assay was used. WST-1 assay was selected as it was used previously successfully with manually constructed barriers.

Procedure

Coating

Two 12-well plates and two 24-well plates were coated with 0.1 mg/ml Poly-D-Lysine; 0.3 ml/well into 12-well plates, and 0.15 ml/well into 24-well plates. The plates were incubated for 5 minutes at room temperature. Then poly-D-lysine solution was removed, the plates were rinsed with sterile distilled water, and left to dry for 2 hours at room temperature.

Construction of Barriers

A 12-well plate with 2.0% GrowDexT (lot 120664618t) was prepared 1 Feb. 2019, and a 12-well plate with 1.5% GrowDex (lot 120074418g) on 5 Feb. 2019.

24-well plates with 1.5% GrowDex (lot 1200615189), and 2.0% GrowDexT (lot 120664618T) barriers were prepared on 5 Feb. 2019. Each barrier consisted of four printed GrowDex layers. For more details on 3D-printing, see Appendix 1.

Figure 24:
FIG. 24 shows barriers constructed on 12-well plate from 2.0% GrowDexT (upper image) and 1.5% GrowDex (lower image). The printing protocol and printing itself were successful.

Printing of 12-well plates was successful as judged visually. FIG. 24 shows barriers constructed on 12-well plate from 2.0% GrowDexT (upper image) and 1.5% GrowDex (lower image). The printing protocol and printing itself were successful.

Figure 25:
FIG. 25 shows barriers constructed on 24-well plate from 2.0% GrowDexT (upper image) and 1.5% GrowDex (lower image).

When printing 24-well plates the syringe plungers of hydrogel syringes (both 1.5% and 2.0%) became rigid (even if neither of the syringes had been opened before), and the hydrogel was transferred to new syringes in the middle of the printing. This impaired the quality of the barriers on 24-well plate. Many of the barriers collapsed and leaked and were not used in the test (FIG. 25). Based on this finding it was concluded that it is necessary to always transfer GrowDex to a new well-working syringe, whether or not the syringe was opened before.

FIG. 25 shows barriers constructed on 24-well plate from 2.0% GrowDexT (upper image) and 1.5% GrowDex (lower image). During 3D-printing both 1.5% GrowDex and 2.0% GrowDexT syringe plungers became rigid and hydrogels had to be transferred to new syringes in the middle of the printing. As a result, many of the barriers collapsed and/or leaked.

After construction, the barriers were left to dry for 1 hr at room temperature, after which they were covered with MEM. The plates was sealed with parafilm and stored at 4° C. until used.

Seeding of Cells (13 Feb. 2019)

12-Well Plates: 400 µl BJ suspension (100 000 cells/ml) was seeded outside of the barriers (→altogether 40 000 BJ cells), and 100 µl BJ cell culture medium was pipetted inside of the barriers.

24-Well Plates: 200 µl of BJ suspension (100 000 cells/ml) was seeded outside of the barriers (→altogether 20 000 BJ cells), and 50 µl BJ cell culture medium was pipetted inside of the barriers.

BJ cell density was selected to match the BJ cell density used in the routine cytotoxicity testing in FICAM (without barriers).

Exposure

Preparation of Chemical Dilutions

SDS: A 0.8 mg/ml SDS stock was prepared in BJ cell culture medium with 5% FBS. The stock was diluted 1:10 to produce 80 µg/ml SDS dilution. The 80 µg/ml SDS dilution was further diluted 1:2 to produce 40 µg/ml dilution. These SDS-dilutions, i.e. 80 µg/ml (C1) and 40 µg/ml (C2) were used in the exposure.

Amitriptyline: A 2 mg/ml stock was prepared in BJ cell culture medium with 5% FBS. The stock was diluted 1:100 to produce 20 µg/ml dilution. The 20 µg/ml dilution was further diluted 1:2 to produce 10 µg/ml dilution. These Amitriptyline dilutions, i.e., 20 µg/ml (C1) and 10 µg/ml (C2), were used in the exposure.

Chemical concentrations were selected based on the previous cytotoxicity data (obtained without barriers), where IC50 for amitriptyline hydrochloride was 12 µg/ml, and for SDS 47 µg/ml. The aim was to detect dose-dependent effect by using a concentration that was expected to kill about half of the cells and a concentration two times bigger than that.

Dosing

12-Well Plates: The medium was removed carefully from both inside and outside of the barriers. 400 µl BJ cell culture medium with 5% FBS was pipetted outside of the barrier (where the cells had been seeded on previous day). 100 µl chemical dilution (SDS or Amitriptyline) was pipetted inside of the barriers.

24-Well Plates: The medium was removed carefully from both inside and outside of the barriers. 200 µl BJ cell culture medium with 5% FBS was pipetted outside of the barrier (where the cells had been seeded on previous day). 50 µl chemical dilution (SDS or Amitriptyline) was pipetted inside of the barriers. The exposure time was 24 hrs.

WST-1 assay

After the 24 hrs exposure, WST-1 assay was performed.

12-Well Plates: 10 µl WST-1 reagent was pipetted inside of the barriers, and 100 µl outside of the barriers.

24-Well Plate: 5 µl WST-1 reagent was added inside of the barriers and 20 µl outside of the barriers.

The plates were incubated for 2.5 hrs before absorbance measurement at 450 nm. The absorbance was measured using multipoint measurement with 49 reads/well in 24-well plates and 81 reads/well in 12-well plates.

Results

According to microscopical evaluation, cells had stayed outside of the barriers as expected. (Note! The failed barriers were rejected already in the beginning, and cells were not seeded to them).

Amitriptyline hydrochloride and SDS were not toxic to the cells: morphological differences were not detected (by visual inspection) nor differences in cell viability (according to WST-assay) between chemical treated cells and untreated cells. This was unexpected as in the previous experiments using manually-prepared GrowDex barriers, chemicals caused toxicity when cells were seeded and chemicals dosed to different sides of the barrier (FICAM 2018). It appears, that the 3D-printed barrier prevents the passage of chemicals across, and is hence different from that prepared manually.

Figure 26:
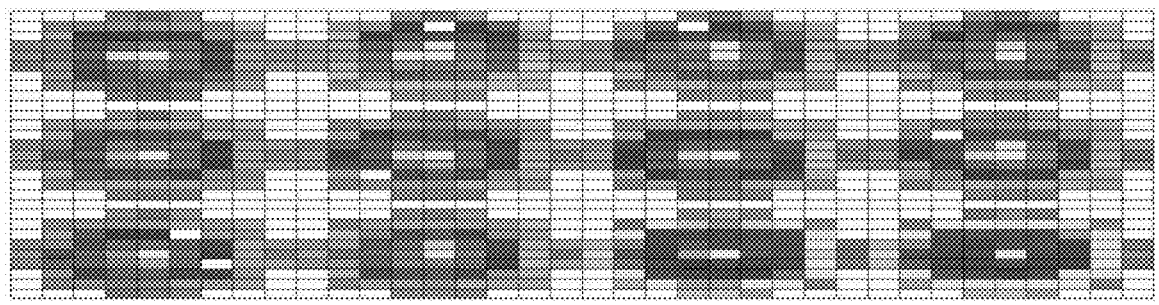
FIG. 26A shows absorbance measurement of the 12-well plates at 450 nm after 24 hrs exposure to chemicals and 2.5 hrs WST-1 incubation with 1.5% GrowDex barriers.
FIG. 26B shows absorbance measurement of the 12-well plates at 450 nm after 24 hrs exposure to chemicals and 2.5 hrs WST-1 incubation with 2.0%
Figure 26:
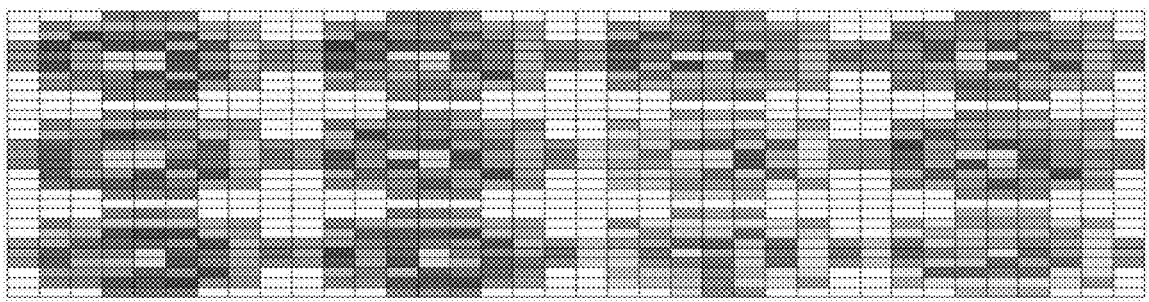

The results indicate that barrier itself absorbs light at 450 nm as seen in the "heatmap" visualization (FIGS. 26, 27 and 28).

The barriers on 12-well plates, that were prepared two weeks before their use, worked properly. In other words, the barriers remain usable at least for two weeks when stored at 4° C. in appropriate vehicle and sealed with parafilm.

Table 11 presents the lay-out of 12-well plates after seeding of cells and exposure to Amitriptyline (Ami) and SDS. Two VC wells are in parenthesis as the cell number in these wells was (by mistake) smaller than in the other wells.

TABLE 11

| 12-well plate lay-out | | | |
| --- | --- | --- | --- |
| SDS C1 | SDS C2 | Ami C1 | Ami C2 |
| SDS C1 | SDS C2 | Ami C1 | Ami C2 |
| VC | VC | (VC) | (VC) |

FIG. 26 shows absorbance measurement of the 12-well plates at 450 nm after 24 hrs exposure to chemicals and 2.5 hrs WST-1 incubation. The absorbances are visualized as a "heatmap" where the dark color intensity is directly proportional to the absorbance. FIG. 26A represents 1.5% GrowDex barriers and FIG. 26B represents 2.0% GrowDex barriers.

Table 12 present the lay-out of 24-well plate with 1.5% GrowDex barriers after seeding of cells and exposure to Amitriptyline and SDS. Only barriers of good quality were used, the strikethroughs represent failed barriers.

TABLE 12

| Failed | Failed | Failed | Failed | Failed | Failed |
| --- | --- | --- | --- | --- | --- |
| Failed | SDS C2 | Ami C1 | Ami C2 | VC | Failed |
| Failed | SDS C2 | Ami C1 | Failed | Failed | Failed |
| Failed | Failed | Failed | Failed | Failed | Failed |

FIG. 27 shows absorbance measurement of the 24-well plate at 450 nm after 24 hrs exposure to chemicals and 2.5 hrs WST-1 incubation. The absorbances are visualized as a "heatmap" where the red color intensity is directly proportional to the absorbance.

Table 13 present the lay-out of 24-well plate with 2.0% GrowDexT barriers after seeding of cells and exposure to Amitriptyline and SDS. Only barriers of good quality were used, the strikethroughs represent failed barriers.

TABLE 13

| 24-well plate lay-out (2.0% GrowDexT) | | | | | |
| --- | --- | --- | --- | --- | --- |
| Failed | Failed | Failed | Failed | Failed | Failed |
| SDS C1 | SDS C2 | Ami C1 | Ami C2 | VC | Failed |
| Failed | Failed | Ami C1 | Failed | VC | Failed |
| SDS C1b | SDS C2b | Ami C1b | Ami C2b | VCb | Failed |

FIG. 28 shows absorbance measurement of the 24-well plate at 450 nm after 24 hrs exposure to chemicals and 2.5 hrs WST-1 incubation. The absorbances are visualized as a "heatmap" where the red color intensity is directly proportional to the absorbance.

Test 2

The aim of Test 2 was to
1) confirm that the cells do not cross the GrowDex barrier
2) find out whether the drugs really do not pass through the GrowDex barrier
3) to find a reason for the high absorbances observed in the barrier For this purpose, we
decreased the cell number from the 40 000 cells/well that was used in Test 1, to 20 000 cells/well
increased the Amitriptyline concentrations from 10 and 20 µg/ml used in Test 1 to 100 and 200 µg/ml, and the SDS concentrations from 40 and 80 µg/ml used in Test 1 to 100 and 200 µg/ml. [By decreasing cell number and increasing chemical concentration it was aimed to increase the sensitivity of the test, and expect to obtain more (measurable/visible) impacts on cells].
included following blanks:
 1.5% GrowDex barrier on poly-D-lysine coated wells in BJ cell culture medium and WST-1, but no cells
 1.5% GrowDex barrier in MEM, no coating, no cells
 1.5% GrowDex barrier in PBS, no coating, no cells
In addition, the number of measurements/well in the multipoint absorbance reading was increased from 81 to 225 reads/well in order to get denser coverage of the well.

One 12-well plate with 1.5% GrowDex barriers was prepared.

Procedure

Construction of Barriers (19 Feb. 2019, Lot 11952)

1.5% GrowDex barriers consisting of four layers, were printed on a 12-well plate. For more details on 3D-printing, see Appendix 1. After construction, the barriers were left to dry for 1 hr at room temperature, after which they were covered with MEM. The plate was sealed with parafilm and stored at 4° C. until used.

Seeding of Cells

The next day after construction of the barriers, BJ fibroblasts were seeded: 400 µl BJ suspension (50 000 cells/ml) was seeded outside of the barriers (→altogether 20 000 BJ cells), and 100 µl BJ cell culture medium was pipetted inside of the barriers. The cells were let to grow for 24 hrs before exposure.

Exposure

Preparation of Chemical Dilutions 2.0 mg/ml stocks were prepared from both Amitriptyline and SDS in BJ cell culture medium with 5% FBS. The stocks were first diluted 1:10 to obtain 200 µl/ml chemical dilution. And the 200 µg/ml chemical dilution was further diluted 1:2 to obtain 100 µg/ml chemical dilution. These dilutions, i.e. 200 and 100 µg/ml were used in the exposure.

Dosing

The medium was removed carefully from both inside and outside of the barriers. 400 µl BJ cell culture medium with 5% FBS was pipetted outside of the barrier (where the cells had been seeded on previous day). 100 µl chemical dilution (SDS or Amitriptyline) was pipetted inside of the barriers. The exposure time was 24 hrs.

Blanks

GrowDex barrier in BJ cell culture medium and WST-1, but no cells, Poly-D-Lysine coated wells (Table 15 and FIG. 30)

GrowDex barrier in MEM, no coating, no cells (FIG. 31)

GrowDex barrier in PBS, no coating, no cells (FIG. 31)

WST-1 Assay

After 24 hrs chemical exposure, 10 µl WST-1 reagent was pipetted inside of the barriers, and 100 µl outside of the barriers. The plate was incubated for 30 min, 1.5 hrs and 2.0 hrs before absorbance measurement at 450 nm. The absorbance was measured using multipoint measurement with 225 reads/well.

Data Handling

In an attempt to quantify the cell viability after different treatments, the mean±STDEV absorbances were calculated using two rows of absorbances that were measured next to the outer edges of the wells. This area was assumed to be outside of the barrier.

Results

Microscopical evaluation revealed that BJ fibroblasts did not pass through the GrowDex barriers, but stayed outside where they were seeded.

Amitriptyline, whose IC50 when dosed to BJ cells without barriers, is 12 µg/ml, caused a dose-dependent reduction in BJ viability (Table 14), i.e., 16% reduction at 200 µg/ml exposure, and a 10% reduction at 100 µg/ml exposure This was a proof of Amitriptyline being able to penetrate the barrier, as cells and Amitriptyline were applied onto different sides of the barrier. However, it is not known whether the 24 hrs exposure was enough for all amitriptyline to "equilibrate" between the two compartments, or whether more time would have been required. It is also not known whether the barrier itself binds Amitriptyline and hence reduces its toxicity.

TABLE 14

The viability of BJ fibroblasts after 24 exposure to amitriptyline or SDS dosed into the other side of the barrier.

|  | Control | 200 µg/ml Amitriptyline hydrochloride | 100 µg/ml Amitriptyline hydrochloride | 200 µg/ml Sodium Dodecyl Sulphate | 100 µg/ml Sodium Dodecyl Sulphate |
|---|---|---|---|---|---|
| Mean absorbance, stdev | 1.007 ± 0.423 | 0.844 ± 0.318 | 0.911 ± 0.283 | 1.189 ± 0.406 | 1.072 ± 0.322 |
| N | 144 | 144 | 144 | 144 | 144 |
| Viability % of Control | 100% | 84% | 90% | 118% | 106% |

Similarly to Test 1, the highest absorbances were measured in barrier regions (FIG. 30). First it was assumed that this was caused by cells or formazan (WST-1 metabolite) accumulating in the barrier as it was expected that the absorbance of GrowDex would be negligible. (In the previous experiments with manually prepared barriers this was a case.) It was, however, not logical that the number of cells in Test 2 were half of the number of cells in Test 1, and still the absorbances were higher in Test 2 than in Test 1.

Measurements of blanks; a GrowDex barrier in BJ cell culture medium+WST-1, but no cells (Table 15, FIGS. 29-30) and a GrowDex barrier in MEM or PBS, no cells, no WST-1 (FIG. 31) gave all high absorbances, which means that BJ cells nor WST-1 metabolites are a reason for these absorbances, instead, they are caused by the barrier structure itself. This absorbance must be due to unspecific scattering, i.e., optical density, OD, induced because the gel is comprised of particles. Therefore the absorbance is high at all wavelengths. One way to overcome the disturbance in WST-1 measurement, is to use reference measurement at wavelength where WST-1 does not absorb (>550 nm). By mapping every spot it is possible to see where the absorbance is actually from WST-1.

TABLE 15

The lay-out of 12-well plate with 1.5% GrowDex barriers after seeding of cells and exposure to Amitriptyline and SDS.

| SDS C1 | SDS C2 | Ami C1 | Ami C2 |
| SDS C1 | SDS C2 | Ami C1 | Ami C2 |
| VC     | VC     | VCb    | VCb    |

FIG. 29 shows 1.5% GrowDex barriers before seeding of BJ cells and exposure (upper image), and after exposure and addition of WST-1 reagent (lower image).

FIG. 30 shows absorbance measurement of the 12-well plate at 450 nm after 24 hrs exposure to chemicals and 2 hrs WST-1 incubation. The absorbances are visualized as a "heatmap" where the red color intensity is directly proportional to the absorbance.

FIG. 31 shows blanks: 1.5% GrowDex barrier in PBS (left), and 1.5% GrowDex barrier in MEM (right), absorbance at 450 nm. The absorbances are visualized as a "heatmap" where the red color intensity is directly proportional to the absorbance.

CONCLUSIONS

The outcome of this study was that
3D printer can be used to construct circular barriers of both 1.5% GrowDex and 2.0% GrowDexT, and to both 12- and 24-well plates. Following issues should be considered:
  It is important that the hydrogel is homogenous. Heterogeneous gel results in uneven and useless barriers. Heterogeneity may result from partial drying of the hydrogel e.g. due defective sealing, opening and re-using of the same syringe, mixing that produces air bubbles etc. One uneven hydrogel layer ruins the whole barrier.
  In order to keep the barriers attached on the bottom of the wells, the wells must be coated ahead. Poly-D-Lysine worked best among the coating materials that were tried.
  After construction, the barriers could be stored at least for two weeks in the fridge covered by e.g. Minimum Essential Medium or PBS, and sealed with parafilm.
A protocol for printing GrowDex is attached as Appendix 2. The protocol should be adjusted for each 3D-printer type.
Barrier properties
  Barriers kept cells in their original compartments, there was no leaking below the barrier nor passage through the barrier
  To what extent and in what time line the chemicals pass through the barrier remained unclear. 3D-printed barriers are constructed differently from the hand-made barriers (see Appendix 3), therefore, it was assumed that their structures are different, and the time lines optimized for hand-made barriers (mainly exposure time) may not be optimal for the 3D-printed barriers, and should be optimized for the 3D-printed barriers separately.
The barrier constructs alone gave high background absorbance, which should be dealt with. This absorbance must be due to unspecific scattering, i.e., optical density, OD, induced because the gel is comprised of particles. Therefore the absorbance is high at all wavelengths (400-600 nm). One way to overcome the disturbance in WST-1 measurement, is to use reference measurement at wavelength where WST-1 does not absorb (>550 nm). By mapping every spot it is possible to see where the absorbance actually comes from WST-1.

APPENDICES

Appendix 1: 3D Printing of GrowDex

TABLE 16

| Date | GrowDex type | Lot # | Syringe details (lose/tight cap. manufacturer) | Storage temp. | Printing protocol (tool file and geometry) | Other remarks/ experiment | Results |
| --- | --- | --- | --- | --- | --- | --- | --- |
| Nov. 29, 2018 | 1.5% | 11952 | Braun Omnifix | +4° C. | 5 ml syringe 16 G 12-well | 1% CaCl2 + medium stability tests | Barriers were not attached to the well bottom |

TABLE 16-continued

| Date | GrowDex type | Lot # | Syringe details (lose/tight cap. manufacturer) | Storage temp. | Printing protocol (tool file and geometry) | Other remarks/ experiment | Results |
|---|---|---|---|---|---|---|---|
| Dec. 4, 2018 | 1.5% | 11952 | Braun Omnifix | +4° C. | 5 ml syringe 16 G 12-well | Poly-D-Lysine. fibronectin & Gelatin coating and stability tests | Poly-D-Lysine and gelatin coated barriers were attached. |
| Dec. 5, 2018 | 2.0% not sterile | 119694117t | Braun Omnifix | +4° C. | 5 ml syringe 16 G 2% 12-well | Printing optimization | Printing OK |
| Dec. 5, 2018 | 1% sterile | 119673917t | Braun Omnifix | +4° C. | 5 ml syringe 16 G 1% 12-well | Printing optimization | Uneven printing |
| Dec. 11, 2018- Dec. 14, 2018 | 2% sterile | 119693318t | Braun Omnifix | +4° C. | 5 ml syringe 16 G 2% 12-well | Cell seeding and leakage test (PDL. Gelatin). WST | Both coating materials leak |
| Dec. 14, 2018 | 1.5% | 119921918g | Braun Omnifix | +4° C. | 5 ml syringe 16 G 12-well | Cell seeding and leakage test (PDL. Gelatin). WST | Gelatin coating leaked. PDL keeps barriers attached and cells outside the barriers |
| Jan. 17, 2019 | 1.5% | 119921918g | Braun Omnifix | +4° C. | 5 ml syringe 16 G. 5 ml syringe 0.41 mm 5 ml syringe 0.8 mm 5 ml syringe 1.2 mm 12-well 24-well | PDL coating | previous protocols no longer work. |
| Jan. 21, 2019 | 2% 1.5% | 2%: 119693318t 1.5:% 119921918g | Braun Omnifix | +4° C. | 5 ml syringe 16 G 2% V2 12-well | PDL coating/ Protocol tests | Raising pushout value has no effect. |
| Jan. 23, 2019 | 1.5% | 11952 119921918g | Braun Omnifix | +4° C. | 5 ml syringe 16 G 12-well | Protocol tests | Original protocol works on lot. 11952. lot 1199219189 doesn't work |
| Jan. 28, 2019 | 1.5% | 11952 | Braun Omnifix | +4° C. | 5 ml syringe 16 G 12-well | Printing optimization | |
| Feb. 1, 2019 | 1.5% | 120061518g | Braun Omnifix Cap OK | RT | 5 ml syringe 16 G 12-well | Barrier printing | Printing doesn't work (clogging) |
| Feb. 1, 2019 | 2.0% | 120664618t | Braun Omnifix Cap OK | RT | 5 ml syringe 16 G 2.0% 12-well | Barrier printing Used in Exposure Test 1 | Protocol and printing OK |

TABLE 16-continued

| Date | GrowDex type | Lot # | Syringe details (lose/tight cap. manufacturer) | Storage temp. | Printing protocol (tool file and geometry) | Other remarks/ experiment | Results |
|---|---|---|---|---|---|---|---|
| Feb. 1, 2019 | 1.5% | 119921918g | Braun Omnifix loose cap | +4° C. | 5 ml syringe 16 G 12-well | Barrier printing | Printing doesn't work (clogging) |
| Feb. 1, 2019 | 1.5% | 120074418g | Braun Omnifix Cap loose | RT | 5 ml syringe 16 G 12-well | Barrier printing | Printing doesn't work (clogging) |
| Feb. 4, 2019 | 1.5% | 120061518g | Braun Omnifix | RT | 5 ml syringe 16 G | Mixing test | Mixing doesn't work (bubbles and clogging) |
| Feb. 4, 2019 | 2.0% | 119693318t | Dried gel on cap | +4 C. | 5 ml syringe 16 G 2% 12 & 24- well | Mixing test | Mixing doesn't work (bubbles and clogging) |
| Feb. 5, 2019 | 1.5% | 120074418g | loose cap | RT | 5 ml syringe 16 G 12-well | Transfer test: changing gel to new syringe. no mixing Used in Exposure. Test 1 | Protocol and printing OK |
| Feb. 5, 2019 | 1.5% | 120074418g | loose cap | RT | 5 ml syringe 16 G 5 ml syringe 0.254 mm 24-well | Optimization | Thick barriers → protocol does not work |
| Feb. 6, 2019 | 1.5% | 11952 | loose cap | +4 C. | 5 ml syringe 16 G 5 ml syringe 0.254 mm 24-well (pienem pi reuna) | Optimization | Thick barriers → protocol does not work |
| Feb. 6, 2019 | 2.0% | 119693318t | dried gel on cap | +4 C. | 5 ml syringe 16 G 2% 24-well (paksum pi reuna) | Optimization | Thick barriers → protocol does not work |
| Feb. 7, 2019 | 2.0% | 119693318t | Transfer to new syringe | +4 C. | 5 ml syringe 16 G 2% V2 24-well (thin wall) | Optimization (only few barriers printed. not the whole plate) | Protocol and printing OK |
| Feb. 7, 2019 | 1.5% | 11952 | Transfer to new syringe | +4 C. | 5 ml syringe 16 G 1.5% V2 24-well (thin wall) | Optimization (only few barriers printed. not the whole plate) | Protocol and printing OK |

TABLE 16-continued

| Date | GrowDex type | Lot # | Syringe details (lose/tight cap. manufacturer) | Storage temp. | Printing protocol (tool file and geometry) | Other remarks/ experiment | Results |
|---|---|---|---|---|---|---|---|
| Feb. 11, 2019 | 1.5% | 120061518g | Cap OK | RT | 5 ml syringe 16 G 1.5% V2 24-well V2 | | Print origin placement issues→ pause& resume after placing plate |
| Feb. 12, 2019 | 1.5%; 2.0% | 120061518g 120664618T | Syringe change in the middle because the syringe was stiff. but even the new syringe was stiff-> variation between syringes | RT | 5 ml syringe 16 G 1.5% V2 5 ml syringe 16 G 2.0% V2 24-well-plates | Used in exposure. Test 1 | Uneven barriers-> Many barriers leaked Test 1 |
| Feb. 19, 2019 | 1.5% | 11952 | Syringe ok | +4 C. | 5 ml syringe 16 G 12-well plate | Used in exposure. Test 2 | Barriers OK |

Appendix 2: 3D Printing Protocol (Optimized for Fab@Home 3D Printer)

1. Transfer GrowDex to a new syringe (test that the plunger moves freely)
2. Pull the plunger up a few mm and then cut the plunger align the top part of the syringe
3. Attach 16G metallic needle with Luer lock to the syringe
4. Push the plunger down until gel starts to flow freely
5. Attach the syringe to the printer holder
6. Perform printer's initialization protocol (set home, start and safe positions)
7. Set printers parameters according to well plate size and GrowDex concentration:

TABLE 17

| | 1.5% GrowDex in 12-well plate | 2.0% GrowDexT in 12-well plate | 1.0% GrowDex in 12-well plate | 1.5% GrowDex in 24-well plate | 2.0% GrowDexT in 24-well plate |
|---|---|---|---|---|---|
| Pathwidth | 1.0 | 1.0 | 1.0 | 1.0 | 1 |
| Pathheight | 1.0 | 1.0 | 1.0 | 1.1 | 1.1 |
| Pushout | 0.050 | 0.050 | 0.200 | 0.050 | 0.05 |
| Suckback | 0.080 | 0.080 | 0.080 | 0.080 | 0.08 |
| Deposition rate | 0.019 | 0.015 | 0.017 | 0.019 | 0.015 |
| Increment | 0.500 | 0.500 | 0.500 | 0.500 | 0.500 |

8. Place appropriate sterile multi well plate coated with poly-D-lysine on stand of the printer
9. Move the syringe tip to the set start position
10. Load stl image of the barriers to be printed to the printer software. Any 3d imaging software capable of saving the image as stl (stereolithography) file can be used.
11. Start printing, monitor the process (movement marginals are close, especially in 24 well plates)
12. After printing has finished, let the barrier dry for 1 h.
13. Add PBS or MEM to the wells. The barriers can be kept in PBS or MEM at 4° C. at least two weeks.

Appendix 3: Differences Between Hand-Made and 3D-Printed 1.5% GrowDex Barriers

TABLE 18

| | Manual barriers* | 3D printed barriers |
|---|---|---|
| Hydrogel | 1.5% GrowDex | 1.5% GrowDex |
| Plate format | 24-well plate | 24-well plate |
| Barrier shape | Straight wall dividing the well into 2 equal-sized compartments | Ring in the middle of the well |
| Coating | No coating | 0.1 mg/ml Poly-D-Lysine |
| μl hydrogel/ring or wall | 500 μl | 417 μl |

TABLE 18-continued

|  | Manual barriers* | 3D printed barriers |
|---|---|---|
| Number of layers | 2 × 250 μl | 4 × (52.125 + 52.125) μl |
| Drying between layers | 30-60 min | 15 min |
| Height (mm) | not available | 5 mm |
| Working volume | 200 μl in both sides | 50 μl inside, 200 μl outside |

*Data from FICAM CT0065/8-12

The invention claimed is:

1. A cell culture plate comprising one or more cell culture well(s) comprising at least one barrier for dividing the well into at least two compartments, wherein the barrier comprises nanofibrillar cellulose hydrogel, wherein the nanofibrillar cellulose has an average fibril diameter of less than 200 nanometers, wherein the nanofibrillar cellulose hydrogel comprises 0.8-2.5% (w/w) of nanofibrillar cellulose, wherein the wall thickness of the barrier is in the range of 0.5-2 mm, wherein cells cannot penetrate the barrier, and wherein the barrier has a height of 1 to 6 mm.

2. The cell culture plate of claim 1, wherein the nanofibrillar cellulose hydrogel comprises 1.0-2.1% (w/w) of nanofibrillar cellulose.

3. The cell culture plate of claim 1, comprising a collagen-based adhesive agent, a fibrinogen-based adhesive agent, a gelatin-based adhesive agent or a lysine-based adhesive agent comprising poly-D-lysine or gelatin between the cell culture plate and the nanofibrillar cellulose hydrogel.

4. The cell culture plate of claim 1, wherein the at least one barrier circumscribes at least one area on the cell culture well.

5. The cell culture plate of claim 1, wherein the nanofibrillar cellulose, when dispersed in water, provides a zero shear viscosity in the range of 1000-100000 Pa·s, and a yield stress in the range of 1-50 Pa, determined by rotational rheometer at a consistency of 0.5% (w/w) by weight in aqueous medium at 22° C.±1° C.

6. The cell culture plate of claim 1, wherein the nanofibrillar cellulose is selected from unmodified nanofibrillar cellulose, anionically modified nanofibrillar cellulose, and oxidized nanofibrillar cellulose.

7. The cell culture plate of claim 1, wherein at least one of the compartment(s) comprise(s) a nanofibrillar cellulose hydrogel having a lower concentration of nanofibrillar cellulose compared to the barrier.

8. The cell culture plate of claim 1, wherein the well contains one type of cells in one compartment and optionally the same and/or other type(s) of cell(s) in at least one other compartment.

9. The cell culture plate of claim 1, wherein the nanofibrillar cellulose, when dispersed in water, provides a zero shear viscosity in the range of 5000-50000 Pa·s, and a yield stress in the range of 3-15 Pa, determined by rotational rheometer at a consistency of 0.5% (w/w) by weight in aqueous medium at 22° C.±1° C.

10. The cell culture plate of claim 1, wherein the nanofibrillar cellulose is TEMPO oxidized nanofibrillar cellulose.

11. The cell culture plate of claim 1, wherein at least one of the compartment(s) comprise(s) a nanofibrillar cellulose hydrogel having a concentration of 0.7% (w/w) or less.

12. The cell culture plate of claim 1, wherein the well contains one type of cells in one compartment and optionally the same and/or other type(s) of cell(s) in at least one other compartment, wherein the cells are selected from liver cells, endothelial cells, adipose cells, cardiomyocytes, kidney cells, immune cells, nerve cells and stem cells.

13. A method for preparing a cell culture plate of claim 1, the method comprising
providing a cell culture plate comprising one or more cell culture well(s),
providing an aqueous dispersion comprising nanofibrillar cellulose wherein the nanofibrillar cellulose has an average fibril diameter of less than 200 nanometers, and wherein the nanofibrillar cellulose is present in an amount of 0.8-2.5% (w/w),
forming at least one barrier from the nanofibrillar cellulose into at least one cell culture well for dividing the well into at least two compartments;
wherein the thickness of the barrier is in the range of 0.5-2 mm;
wherein cells cannot penetrate the barrier; and
wherein the barrier has a height of 1 to 6 mm.

14. The method of claim 13, wherein the forming the at least on barrier comprises preparing the barrier by additive manufacturing.

15. The method of claim 13, comprising coating the one or more cell culture well with an adhesive agent before providing the at least one barrier.

16. A method for detecting a substance, the method comprising
providing the cell culture plate of claim 1 comprising a first cell in a first compartment, and
detecting from another compartment at least one substance.

17. The method of claim 16, comprising
applying a substance of interest to a compartment,
incubating the cell for a time sufficient to allow the cell to respond to the substance of interest,
detecting from another compartment at least one substance.

18. The method of claim 17, the method comprising
further providing a second cell in a second compartment,
detecting from the second compartment at least one substance secreted by the second cell and/or the reaction of the second cell, and
based on the detected substance(s) secreted by the second cell and/or the reaction of the second cell evaluating the effect of the substance of interest to the first cell and/or to the second cell.

19. The method of claim 16, wherein the first cells are selected from liver cells, endothelial cells, adipose cells, cardiomyocytes, kidney cells, immune cells, nerve cells, and stem cells.

20. The method of claim 14, wherein the first cells and/or the second cells are selected from liver cells, endothelial cells, adipose cells, cardiomyocytes, kidney cells, immune cells, nerve cells, and stem cells.

* * * * *